United States Patent
Yang et al.

(10) Patent No.: US 12,428,428 B2
(45) Date of Patent: Sep. 30, 2025

(54) TRICYCLIC TETRAHYDROISOQUINOLINE DERIVATIVE, PREPARATION METHOD THEREFOR AND APPLICATION THEREOF IN MEDICINE

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Fanglong Yang, Shanghai (CN); Xing Fan, Shanghai (CN); Jingjing Yan, Shanghai (CN); Xiqian Zhang, Shanghai (CN); Feng He, Shanghai (CN); Weikang Tao, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

(*) Notice: Subject to any disclaimer, the term of this patent is extended or adjusted under 35 U.S.C. 154(b) by 733 days.

(21) Appl. No.: 17/790,110

(22) PCT Filed: Jan. 8, 2021

(86) PCT No.: PCT/CN2021/070826
§ 371 (c)(1),
(2) Date: Jun. 29, 2022

(87) PCT Pub. No.: WO2021/139756
PCT Pub. Date: Jul. 15, 2021

(65) Prior Publication Data
US 2023/0140679 A1    May 4, 2023

(30) Foreign Application Priority Data

Jan. 10, 2020  (CN) .......................... 202010025118.5
Jan. 14, 2020  (CN) .......................... 202010036802.3
Apr. 9, 2020   (CN) .......................... 202010273891.3
Jul. 15, 2020  (CN) .......................... 202010680491.4
Aug. 14, 2020  (CN) .......................... 202010819555.4
Sep. 16, 2020  (CN) .......................... 202010971693.4

(51) Int. Cl.
C07D 491/06    (2006.01)

(52) U.S. Cl.
CPC ................................... C07D 491/06 (2013.01)

(58) Field of Classification Search
CPC .................................................... C07D 491/06
See application file for complete search history.

(56) References Cited

U.S. PATENT DOCUMENTS

2014/0249162 A1    9/2014  Son et al.
2017/0320871 A1*  11/2017  Labadie .................. A61P 35/00

FOREIGN PATENT DOCUMENTS

| CN | 109219604 A  | 1/2019 |
| CN | 109776523 A  | 5/2019 |
| EP |   1113007 A1 | 7/2001 |
| WO | 2008080001 A2| 7/2008 |
| WO | 2014106848 A1| 7/2014 |
| WO | 2014135834 A1| 9/2014 |
| WO | 2014141292 A2| 9/2014 |

(Continued)

OTHER PUBLICATIONS

Salomé Llabrés et al., Molecular basis of the selective binding of MDMA enantiomers to the alpha4beta2 nicotinic receptor subtype: Synthesis, pharmacological evaluation and mechanistic studies, European Journal of Medicinal Chemistry (2014), vol. 81, pp. 35-46, http://dx.doi.org/10.1016/j.ejmech.2014.04.044 (12 pages).

(Continued)

*Primary Examiner* — Timothy R Rozof
(74) *Attorney, Agent, or Firm* — Morgan, Lewis & Bockius LLP

(57) ABSTRACT

The present disclosure relates to a tricyclic tetrahydroisoquinoline derivative, a preparation method therefor and an application thereof in medicine. In particular, the present disclosure relates to a tricyclic tetrahydroisoquinoline derivative represented by general formula (I), a preparation method therefor and a pharmaceutical composition comprising said derivative, a use thereof as an estrogen receptor modulator, and a use thereof in preparing a drug for treating estrogen receptor-mediated or dependent diseases or disorders. The substituents in general formula (I) are the same as those defined in the description.

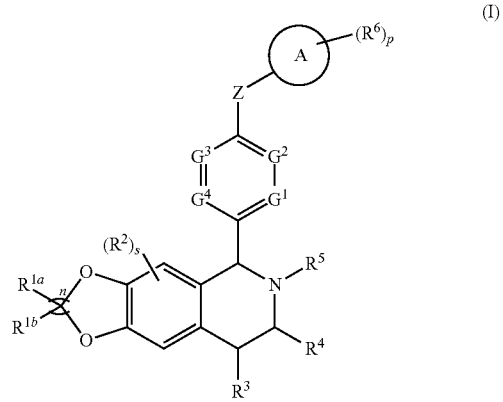

20 Claims, No Drawings
Specification includes a Sequence Listing.

(56) References Cited

FOREIGN PATENT DOCUMENTS

| WO | 2014151899 A1 | 9/2014 |
| WO | 2014165723 A2 | 10/2014 |
| WO | 2014191726 A1 | 12/2014 |
| WO | 2015092634 A1 | 6/2015 |
| WO | 2016202161 A1 | 12/2016 |
| WO | 2019002442 A1 | 1/2019 |
| WO | 2019192533 A1 | 10/2019 |
| WO | 2019228443 A1 | 12/2019 |

OTHER PUBLICATIONS

Tetsuya Toba et al., Synthesis and evaluation of N-(4-benzylphenyl)piperazines as VGF inducers, Bioorganic & Medicinal Chemistry Letters (2018), vol. 28, pp. 2528-2532, https://doi.org/10.1016/j.bmcl.2018.05.047 (5 pages).

* cited by examiner

TRICYCLIC TETRAHYDROISOQUINOLINE DERIVATIVE, PREPARATION METHOD THEREFOR AND APPLICATION THEREOF IN MEDICINE

CROSS-REFERENCE TO RELATED APPLICATIONS

The present application is a national stage application of International Patent Application No. PCT/CN2021/070826, filed Jan. 8, 2021, which claims the benefit of and priority to the Chinese Patent Application No. 202010025118.5 filed Jan. 10, 2020, Chinese Patent Application No. 202010036802.3 filed Jan. 14, 2020, Chinese Patent Application No. 202010273891.3 filed Apr. 9, 2020, Chinese Patent Application No. 202010680491.4 filed Jul. 15, 2020, Chinese Patent Application No. 202010819555.4 filed Aug. 14, 2020, and Chinese Patent Application No. 202010971693.4 filed Sep. 16, 2020, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 29, 2022 is named "702149CPUS_126268-5035-US_ST25_Sequence_Listing. TXT" and is approximately 2 kilobytes in size.

TECHNICAL FIELD

The present disclosure belongs to the field of pharmaceutics, and relates to a tricyclic tetrahydroisoquinoline derivatives, a preparation method therefor and use thereof in pharmaceutics. In particular, the present disclosure relates to a tricyclic tetrahydroisoquinoline derivative of general formula (I), a preparation method therefor, a pharmaceutical composition comprising the derivative, and use thereof as an estrogen receptor modulator for treating an estrogen receptor-mediated or -dependent disease or condition, wherein the disease is particularly preferably breast cancer.

BACKGROUND

After long-term basic research and clinical monitoring, it is found that diseases such as breast cancer, ovarian cancer, osteoporosis, schizophrenia, senile dementia, etc. are closely associated with the abnormality of the estrogen signaling pathway. Estrogen is a steroid hormone secreted by the endocrine system. It plays an important role in the reproductive system, bone tissue, cardiovascular system, immune system and central nervous system. The estrogen signaling system plays an important role in regulating cell growth, differentiation and apoptosis. The development and progression of estrogen-dependent tumors such as breast cancer, ovarian cancer, endometrial cancer, etc. are closely associated with estrogen. Currently, the main chemotherapy for breast cancer is the use of antiestrogens such as tamoxifen; however, tamoxifen acts as an estrogen agonist in the uterus, having a stimulatory effect on cancer cells in the uterus. Because of these serious side effects, it is imperative to find new safe and effective treatments.

An important protein in the estrogen signaling pathway is estrogen receptor (ER). ER is a steroid hormone receptor and is a ligand-activated transcription factor that belongs to the nuclear receptor superfamily. It includes two subtypes: ERα (found in 1950) and ERβ (found in 1996), each encoded by a different gene. ERα and ERβ are highly similar at the amino acid level: they are up to 97% similar in the DNA-binding domain and up to 56% similar in the ligand-binding domain. However, they are only 24% homologous at the N-terminus, which is considered low. ER comprises 6 domains (A-F), which form 4 main functional regions. The functional region of the N-terminal A/B domain includes a ligand-independent transcriptional activation functional region AF-1, which has constitutive activation activity and activates the transcription of a target gene by acting with basal transcription factors, reactivating factors and other transcription factors. The region has a plurality of phosphorylation sites. It is reported that the action of AF-1 is dependent on protein phosphorylation. The DNA-binding domain (DBD) formed from the C domain is highly conserved and comprises two zinc-finger domains capable of specifically binding to target DNA. The domain also plays an important role in receptor dimerization. The D domain is a hinge region, linking the DBD and the ligand-binding domain (LBD). It is lowly conserved (two subtypes are only 30% homologous). The C-terminal E domain forms the ligand-binding domain (LBD), which determines the specific binding of ER to ligands such as estrogen, SERM (selective estrogen receptor modulator), SERD (selective estrogen receptor degrader), and the like. The LBD includes a ligand-dependent transcriptional activation functional region AF-2, which acts synergistically with AF-1 to enable ER to activate the transcription of the target gene. Also, the LBD has a powerful dimerization interface, and can still function without a ligand; therefore, the LBD is a critical site for receptor dimerization.

ERα is distributed primarily in the uterus, ovary, testis, pituitary, kidney, epididymis and adrenal gland, while ERβ is distributed primarily in the prostate, ovary, lung, bladder, brain and blood vessels. Since full agonists or full antagonists all have serious side effects, effort is being put into research on SERMs. By "selective" is meant that SERMs act as agonists in certain tissues such as the bones, liver, and ERβ-concentrated region of the cardiovascular system, while as antagonists in some other tissues such as the mammary gland. They may act as agonists or antagonists in the uterus (a region where ERα is more predominant). Currently available SERMs on the market include tamoxifen, raloxifene, bazedoxifene, toremifene, etc. However, it has been shown that currently available SERMs on the market still have serious side effects; for example, the long-term use of tamoxifen and toremifene can cause endometrial hyperplasia, polyps, endometrial carcinoma, etc., and raloxifene has common side effects including hot flashes, leg pain, breast swelling and pain, venous embolism, etc. Therefore, the research and development of novel compounds is still a problem to be solved.

Tamoxifen belongs to a class of compounds called selective estrogen receptor modulators (SERMs). It can stabilize ERα and up-regulate somewhat the level of ERα receptors. In contrast, fulvestrant can cause fast degradation of ERα and escalated blocking of the ER signaling pathways; such compounds are referred to as selective estrogen receptor degraders (SERDs). The differences in the mechanisms of action of these SERMs and SERDs also appear to be the mechanism responsible for the resistance to these compounds. Many tumors that are tamoxifen-resistant but remain ER-positive remain sensitive to fulvestrant. It has been clinically found that SERDs such as fulvestrant are effective in treating some ERα-positive, tamoxifen-resistant breast cancer. Thus, compounds that cause degradation of ERα can be used to extend the time span within which the anti-estrogen therapy (different SERMs, aromatase inhibitors and SERDs may be used in sequence) is effective in treating breast cancer patients.

Disclosed patent applications regarding selective estrogen receptor-mediated modulators include WO2014165723, WO2014151899, WO2014141292, WO2014191726, WO2015092634, WO2014135834, WO2014106848 and EP1113007.

SUMMARY

The present disclosure is intended to provide a compound of general formula (I) or a tautomer, mesomer, racemate, enantiomer, or diastereomer thereof or a mixture thereof, or a pharmaceutically acceptable salt thereof, wherein the compound of general formula (I) has a structure as shown below:

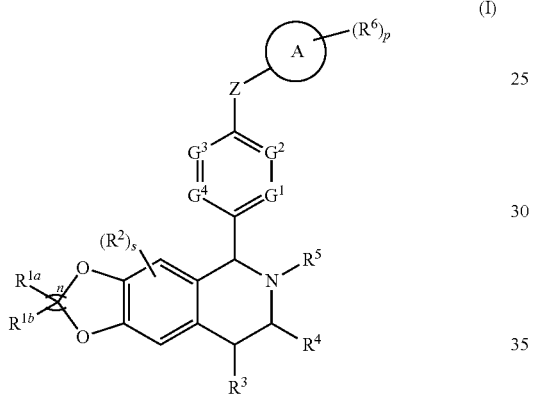

(I)

wherein:
ring A is heterocyclyl;
Z is selected from the group consisting of O atom, S atom, $NR^7$ and $CR^9R^{10}$;
$G^1$, $G^2$, $G^3$ and $G^4$ are identical or different and are each independently $CR^8$ or a N atom;
$R^{1a}$ and $R^{1b}$ are identical or different and are each independently selected from the group consisting of hydrogen atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
$R^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
$R^3$ is selected from the group consisting of hydrogen atom, alkyl and cycloalkyl, wherein the alkyl and cycloalkyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
$R^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
$R^5$ is selected from the group consisting of hydrogen atom, alkyl, haloalkyl and cycloalkyl, wherein the alkyl and cycloalkyl are each independently optionally substituted with one or more substituents selected from the group consisting of halogen, alkyl, alkoxy, cyano, amino, nitro, carboxyl, hydroxy, hydroxyalkyl, cycloalkyl, heterocyclyl, aryl and heteroaryl;
$R^6$ are identical or different and are each independently selected from the group consisting of hydrogen atom, alkyl, deuterated alkyl, haloalkyl, alkoxy, cyano, amino, nitro, halogen, carboxyl, aldehyde, hydroxy, hydroxyalkyl, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
$R^7$ is selected from the group consisting of hydrogen atom, alkyl, haloalkyl, alkenyl, propargyl, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
$R^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
$R^9$ and $R^{10}$ are identical or different and are each independently selected from the group consisting of hydrogen atom, halogen, alkyl, alkoxy, hydroxy, hydroxyalkyl, haloalkyl, alkenyl, alkynyl, cyano, cycloalkyl and heterocyclyl;
n is 1, 2 or 3;
s is 0, 1 or 2; and
p is 0, 1, 2 or 3.

In some embodiments of the present disclosure, in a compound of general formula (I) or a tautomer, mesomer, racemate, enantiomer or diastereomer thereof or a mixture thereof, or a pharmaceutically acceptable salt thereof,

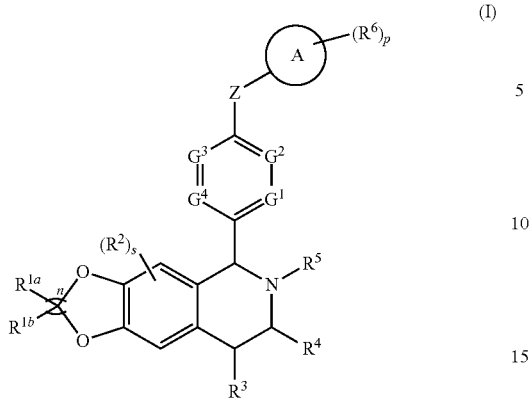

wherein:
- $R^{1a}$ and $R^{1b}$ are identical or different and are each independently selected from the group consisting of H atom, deuterium atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
- ring A is heterocyclyl;
- Z is selected from the group consisting of O atom, S atom, $NR^7$ and $CR^9R^{10}$;
- $G^1$, $G^2$, $G^3$ and $G^4$ are identical or different and are each independently $CR^8$ or a N atom;
- $R^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
- $R^3$ is selected from the group consisting of hydrogen atom, alkyl and cycloalkyl, wherein the alkyl and cycloalkyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
- $R^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
- $R^5$ is selected from the group consisting of hydrogen atom, alkyl, haloalkyl and cycloalkyl, wherein the alkyl and cycloalkyl are each independently optionally substituted with one or more substituents selected from the group consisting of halogen, alkyl, alkoxy, cyano, amino, nitro, carboxyl, hydroxy, hydroxyalkyl, cycloalkyl, heterocyclyl, aryl and heteroaryl;
- $R^6$ are identical or different and are each independently selected from the group consisting of hydrogen atom, alkyl, deuterated alkyl, haloalkyl, alkoxy, cyano, amino, nitro, halogen, carboxyl, aldehyde, hydroxy, hydroxyalkyl, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
- $R^7$ is selected from the group consisting of hydrogen atom, alkyl, haloalkyl, alkenyl, propargyl, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
- $R^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
- $R^9$ and $R^{10}$ are identical or different and are each independently selected from the group consisting of hydrogen atom, halogen, alkyl, alkoxy, hydroxy, hydroxyalkyl, haloalkyl, alkenyl, alkynyl, cyano, cycloalkyl and heterocyclyl;
- n is 1, 2 or 3;
- s is 0, 1 or 2; and
- p is 0, 1, 2 or 3.

In some embodiments of the present disclosure, in a compound of general formula (I) or a tautomer, mesomer, racemate, enantiomer or diastereomer thereof or a mixture thereof, or a pharmaceutically acceptable salt thereof, ring A is 3- to 6-membered heterocyclyl containing 1 to 3 heteroatoms selected from the group consisting of N atom, O atom and S atom, and is preferably selected from the group consisting of azetidinyl, pyrrolidinyl and piperidinyl, and is more preferably pyrrolidinyl or piperidinyl.

In other embodiments of the present disclosure, in a compound of general formula (I) or a tautomer, mesomer, racemate, enantiomer, diastereomer or a mixture thereof, or a pharmaceutically acceptable salt thereof, $G^1$, $G^2$, $G^3$ and $G^4$ are all $CR^8$, or one of $G^1$, $G^2$, $G^3$ and $G^4$ is a N atom, and the others are $CR^8$; preferably, $G^1$, $G^2$, $G^3$ and $G^4$ are all $CR^8$, or $G^1$ is N, and $G^2$, $G^3$ and $G^4$ are $CR^8$; $R^8$ are as defined in general formula (I); preferably, $R^8$ are identical or different and are each independently a hydrogen atom or halogen.

In some embodiments of the present disclosure, a compound of general formula (I) or a tautomer, mesomer, racemate, enantiomer or diastereomer thereof or a mixture thereof, or a pharmaceutically acceptable salt thereof, is a compound of general formula (II):

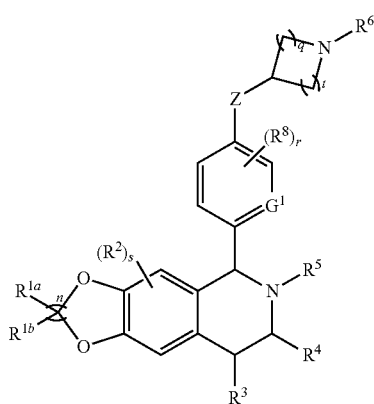

(II)

wherein:
r is 0, 1, 2 or 3;
q is 1, 2 or 3;
t is 1 or 2;
Z, $G^1$, $R^{1a}$, $R^{1b}$, $R^2$-$R^6$, $R^8$, n and s are as defined in the general formula (I).

In some embodiments of the present disclosure, a compound of general formula (I) or a tautomer, mesomer, racemate, enantiomer or diastereomer thereof or a mixture thereof, or a pharmaceutically acceptable salt thereof, is a compound of general formula (IIG) or (IIGa):

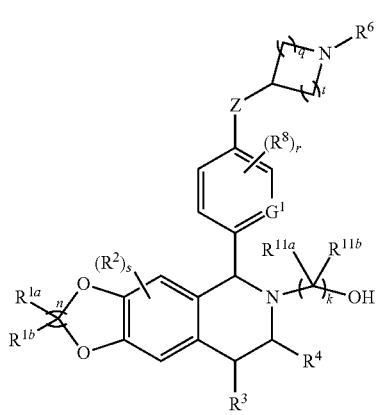

(IIG)

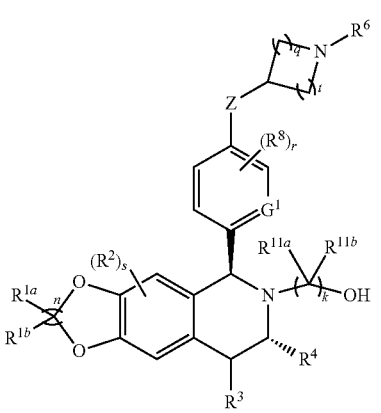

(IIGa)

wherein:
$R^{11a}$ and $R^{11b}$ are identical or different and are each independently selected from the group consisting of hydrogen atom, halogen, alkyl, haloalkyl, hydroxyalkyl, alkoxy, cyano, amino, nitro, carboxyl, hydroxy, cycloalkyl, heterocyclyl, aryl and heteroaryl;
k is an integer from 1 to 6;
q is 1, 2 or 3;
t is 1 or 2;
r is 0, 1, 2 or 3;
$G^1$, Z, $R^{1a}$, $R^{1b}$, $R^2$-$R^4$, $R^6$, $R^8$, n and s are as defined in general formula (I).

In some other embodiments of the present disclosure, in compounds of general formulas (I), (II), (IIG) and (IIGa) or tautomers, mesomers, racemates, enantiomers or diastereomers thereof or mixtures thereof, or pharmaceutically acceptable salts thereof, Z is $NR^7$ or an O atom; $R^7$ is as defined in general formula (I).

In some other embodiments of the present disclosure, in compounds of general formulas (I), (II), (IIG) and (IIGa) or tautomers, mesomers, racemates, enantiomers or diastereomers thereof or mixtures thereof, or pharmaceutically acceptable salts thereof, Z is $NR^7$; $R^7$ is as defined in general formula (I).

In some other embodiments of the present disclosure, in compounds of general formulas (II), (IIG) and (IIGa) or tautomers, mesomers, racemates, enantiomers or diastereomers thereof or mixtures thereof, or pharmaceutically acceptable salts thereof, q is 2, and t is 1; or q is 2, and t is 2.

In some other embodiments of the present disclosure, in compounds of general formulas (I), (II), (IIG) and (IIGa) or tautomers, mesomers, racemates, enantiomers or diastereomers thereof or mixtures thereof, or pharmaceutically acceptable salts thereof, n is 1.

In some embodiments of the present disclosure, a compound of general formula (I) or a tautomer, mesomer, racemate, enantiomer or diastereomer thereof or a mixture thereof, or a pharmaceutically acceptable salt thereof, is a compound of general formula (III) or (IIIa):

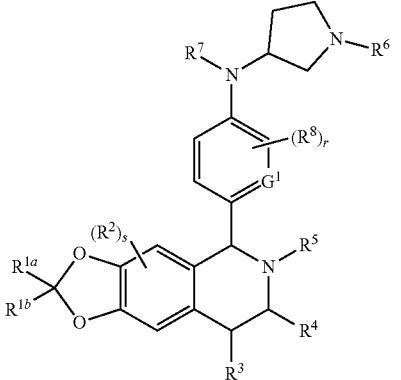

(III)

-continued (IIIa)

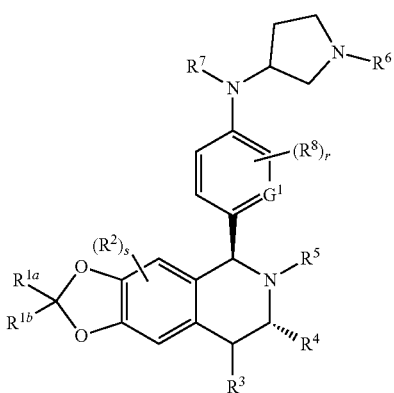

wherein:
r is 0, 1, 2 or 3;
$G^1$, $R^{1a}$, $R^{1b}$, $R^2$-$R^8$ and s are as defined in general formula (I).

In some embodiments of the present disclosure, a compound of general formula (I) or a tautomer, mesomer, racemate, enantiomer or diastereomer thereof or a mixture thereof, or a pharmaceutically acceptable salt thereof, is a compound of general formula (IV) or (IVa):

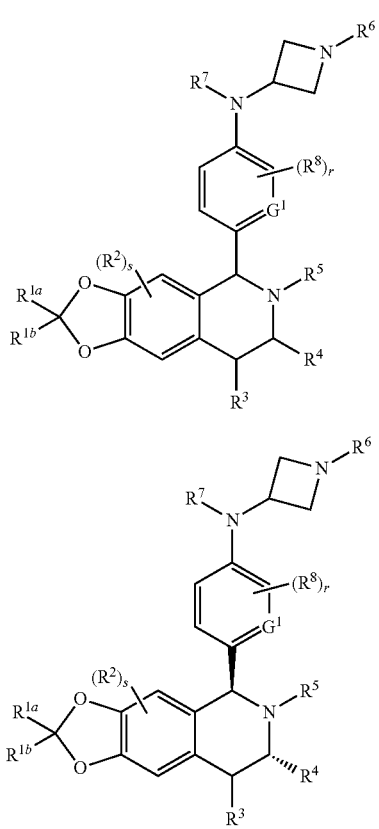

wherein:
r is 0, 1, 2 or 3;
$G^1$, $R^{1a}$, $R^{1b}$, $R^2$-$R^8$ and s are as defined in general formula (I).

In some other embodiments of the present disclosure, in the above compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $G^1$ is $CR^8$; $R^8$ is as defined in general formula (I). In some other embodiments of the present disclosure, in the above compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $G^1$ is N.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^7$ is a hydrogen atom.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^{1a}$ and $R^{1b}$ are identical or different and are each independently selected from the group consisting of hydrogen atom, halogen, alkyl, deuterated alkyl and haloalkyl.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^{1a}$ and $R^{1b}$ are identical or different and are each independently selected from the group consisting of H atom, deuterium atom, fluorine atom and $C_{1-6}$ alkyl; preferably, $R^{1a}$ and $R^{1b}$ are deuterium atoms.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^{1a}$ and $R^{1b}$ are identical or different and are each independently selected from the group consisting of hydrogen atom, halogen, alkyl, deuterated alkyl and haloalkyl; preferably, $R^{1a}$ and $R^{1b}$ are identical or different and are each independently selected from the group consisting of hydrogen atom, fluorine atom and $C_{1-6}$ alkyl.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^2$ is a hydrogen atom.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^3$ is a hydrogen atom.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^4$ is a hydrogen atom or alkyl, preferably $C_{1-6}$ alkyl, and more preferably methyl.

In some other embodiments of the present disclosure, in compounds of general formulas (I), (II), (III), (IIIa), (IV) and (IVa) or tautomers, mesomers, racemates, enantiomers or diastereomers thereof or mixtures thereof, or pharmaceutically acceptable salts thereof, $R^5$ is alkyl optionally further substituted with one or more substituents selected from the group consisting of halogen, amino, cyano, hydroxy, alkoxy, carboxyl and cycloalkyl; $R^5$ is preferably alkyl optionally substituted with one or more substituents selected from the group consisting of halogen and hydroxy, more preferably —$CH_2$—$CF_3$, —$CH_2$—$CHF_2$, —$CH_2$—$CF_2$—$CH_2OH$, —$CH_2$—$CF_2$—$CH_3$ or —$CH_2$—$CF(CH_3)_2$, and most preferably —$CH_2$—$CF_3$ or —$CH_2$—$CF_2$—$CH_2OH$.

In some other embodiments of the present disclosure, in compounds of general formulas (I), (II), (III), (IIIa), (IV) and (IVa) or tautomers, mesomers, racemates, enantiomers or diastereomers thereof or mixtures thereof, or pharmaceutically acceptable salts thereof, $R^5$ is alkyl or haloalkyl, wherein the alkyl is optionally further substituted with one or more substituents selected from the group consisting of halogen, amino, cyano, hydroxy, alkoxy, carboxyl and cycloalkyl, and is preferably alkyl or haloalkyl, more preferably —$CH_2$—$CF_3$, —$CH_2$—$CHF_2$, —$CH_2$—$CF_2$—$CH_3$ or —$CH_2$—$CF(CH_3)_2$, and most preferably —$CH_2$—$CF_3$.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^6$ is a hydrogen atom or haloalkyl.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^6$ is haloalkyl, preferably $C_{1-6}$ haloalkyl, more preferably —$CH_2$—$CH_2$—$CH_2F$, —$CH_2$—$CH_2$—$CF_3$ or —$CH_2$—$CH_2$—$CH_2$—$CF_3$, and most preferably —$CH_2$—$CH_2$—$CH_2F$.

In some other embodiments of the present disclosure, in compounds of general formulas (I), (II), (IIG), (IIGa), (III), (IIIa), (IV) and (IVa) or tautomers, mesomers, racemates, enantiomers or diastereomers thereof or mixtures thereof, or pharmaceutically acceptable salts thereof, $R^8$ are identical or different and are each independently selected from the group consisting of hydrogen atom, halogen, alkyl, alkoxy, haloalkyl and cyano, and are preferably hydrogen atoms or halogens.

In some other embodiments of the present disclosure, in a compound of general formula (II) or a tautomer, mesomer, racemate, enantiomer or diastereomer thereof or a mixture thereof, or a pharmaceutically acceptable salt thereof, $G^1$ is $CR^8$ or a N atom, preferably a N atom; Z is $NR^7$ or an O atom; $R^{1a}$ and $R^{1b}$ are identical or different and are each independently selected from the group consisting of H atom and deuterium atom; $R^2$ is a hydrogen atom; $R^3$ is a hydrogen atom; $R^4$ is methyl; $R^5$ is $C_{1-6}$ alkyl optionally substituted with one or more substituents selected from the group consisting of halogen and hydroxy; $R^6$ is $C_{1-6}$ haloalkyl; $R^7$ is a hydrogen atom; $R^8$ are identical or different and are each independently a hydrogen atom or a halogen; r is 0, 1 or 2; n is 1; q is 1 or 2; and t is 1.

In some other embodiments of the present disclosure, in compounds of general formulas (III), (IIIa), (IV) and (IVa) or tautomers, mesomers, racemates, enantiomers or diastereomers thereof or mixtures thereof, or pharmaceutically acceptable salts thereof, $G^1$ is $CR^8$ or a N atom, preferably a N atom; $R^{1a}$ and $R^{1b}$ are identical or different and are each independently selected from the group consisting of H atom and deuterium atom; $R^2$ is a hydrogen atom; $R^3$ is a hydrogen atom; $R^4$ is methyl; $R^5$ is $C_{1-6}$ alkyl optionally substituted with one or more substituents selected from the group consisting of halogen and hydroxy; $R^6$ is $C_{1-6}$ haloalkyl; $R^7$ is a hydrogen atom; $R^8$ are identical or different and are each independently a hydrogen atom or a halogen; and r is 0, 1 or 2.

Typical compounds disclosed herein include, but are not limited to:

| Example | Structure and name of compound |
|---|---|
| 1 | (S)-1-(3-fluoropropyl)-N-(4-((5R,7R)-7-methyl-6-(2,2,2-trifluoroethyl)-5,6,7,8-tetrahydro-[1,3]dioxo[4,5-g]isoquinolin-5-yl)phenyl)pyrrolidin-3-amine 1 |
| 2 | (S)-N-(3,5-difluoro-4-((5S,7R)-7-methyl-6-(2,2,2-trifluoroethyl)-5,6,7,8-tetrahydro-[1,3]dioxo[4,5-g]isoquinolin-5-yl)phenyl)-1-(3-fluoropropyl)pyrrolidin-3-amine 2 |

| Example | Structure and name of compound |
|---|---|
| 3 | 2,2-Difluoro-3-((5R,7R)-5-(4-(((S)-1-(3-fluoropropyl)pyrrolidin-3-yl)amino)phenyl)-7-methyl-7,8-dihydro-[1,3]dioxolo[4,5-g]isoquinolin-6(5H)-yl)propan-1-ol 3 |
| 4 | 2,2-Difluoro-3-((5S,7R)-5-(5-(((S)-1-(3-fluoropropyl)pyrrolidin-3-yl)amino)pyridin-2-yl)-7-methyl-7,8-dihydro-[1,3]dioxolo[4,5-g]isoquinolin-6(5H)-yl)propan-1-ol 4 |
| 5 | 3-((5S,7R)-5-(2,6-difluoro-4-(((S)-1-(3-fluoropropyl)pyrrolidin-3-yl)amino)phenyl)-7-methyl-7,8-dihydro-[1,3]dioxolo[4,5-g]isoquinolin-6(5H)-yl)-2,2-difluoropropan-1-ol 5 |
| 6 | N-((S)-1-(3-fluoropropyl)pyrrolidin-3-yl)-6-((5S,7R)-7-methyl-6-(2,2,2-trifluoroethyl)-5,6,7,8-tetrahydro[1,3]dioxolo[4,5-g]isoquinolin-5-yl)pyridin-3-amine 6 |
| 7 | (S)-N-(4-((5S,7R)-2,2-difluoro-7-methyl-6-(2,2,2-trifluoroethyl)-5,6,7,8-tetrahydro-[1,3]dioxolo[4,5-g]isoquinolin-5-yl)-3,5-difluorophenyl)-1-(3-fluoropropyl)pyrrolidin-3-amine 7 |
| 8 | 6-((5S,7R)-2,2-difluoro-7-methyl-6-(2,2,2-trifluoroethyl)-5,6,7,8-tetrahydro-[1,3]dioxolo[4,5-g]isoquinolin-5-yl)-N-((S)-1-(3-fluoropropyl)pyrrolidin-3-yl)pyridin-3-amine 8 |

| Example | Structure and name of compound |
|---|---|
| 9 | 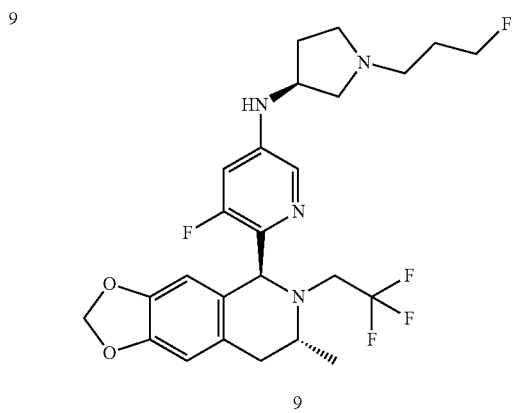

5-Fluoro-N-((S)-1-(3-fluoropropyl)pyrrolidin-3-yl)-6-((5S,7R)-7-methyl-6-(2,2,2-trifluoroethyl)-5,6,7,8-tetrahydro-[1,3]dioxolo[4,5-g]isoquinolin-5-yl)pyridin-3-amine 9 |
| 10 | 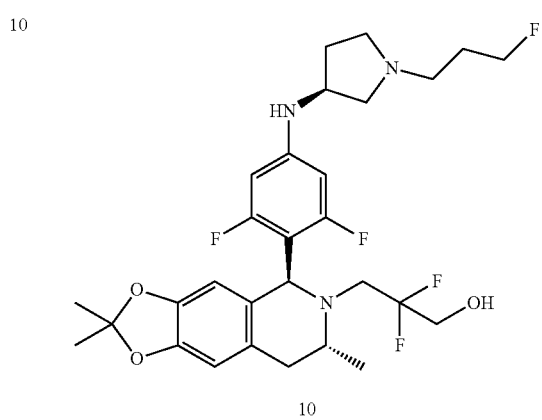

3-((5S,7R)-5-(2,6-difluoro-4-(((S)-1-(3-fluoropropyl)pyrrolidin-3-yl)amino)phenyl)-2,2,7-trimethyl-7,8-dihydro-[1,3]dioxolo[4,5-g]isoquinolin-6(5H)-yl)-2,2-difluoropropan-1-ol 10 |
| 11 | 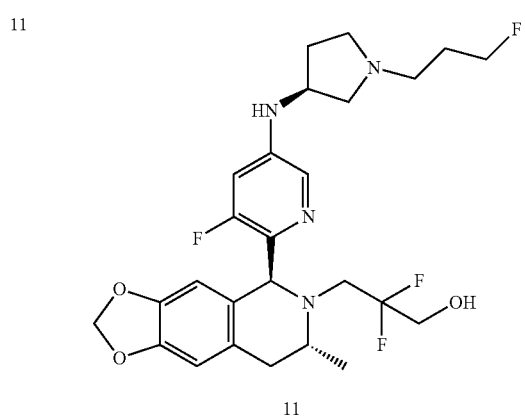

2,2-Difluoro-3-((5S,7R)-5-(3-fluoro-5-(((S)-1-(3-fluoropropyl)pyrrolidin-3-yl)amino)pyridin-2-yl)-7-methyl-7,8-dihydro-[1,3]dioxolo[4,5-g]isoquinolin-5(5H)-yl)propan-1-ol 11 |
| 12 | 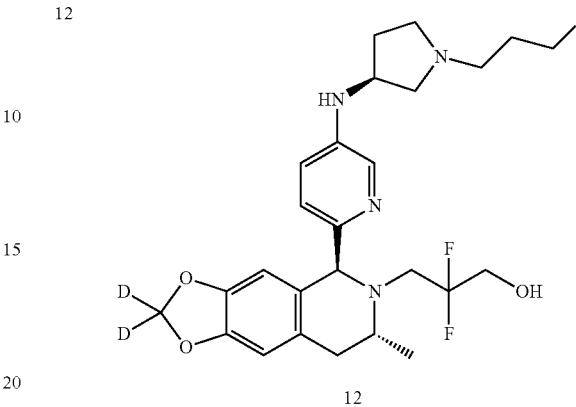

2,2-Difluoro-3-((5S,7R)-5-(5-(((S)-1-(3-fluoropropyl)pyrrolidin-3-yl)amino)pyridin-2-yl)-7-methyl-7,8-dihydro-[1,3]dioxolo[4,5-g]isoquinolin-6(5H)-yl-2,2-$d_2$)propan-1-ol 12 |
| 13 | 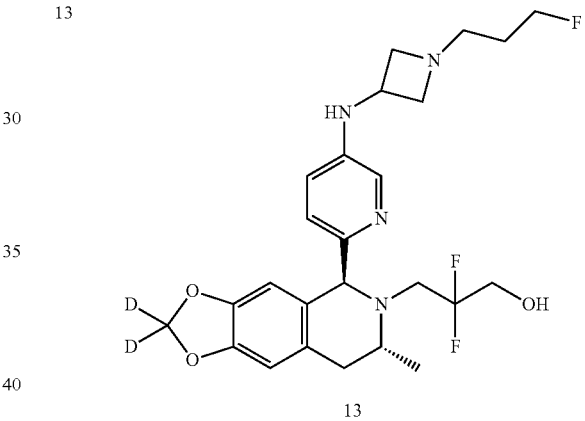

2,2-Difluoro-3-((5S,7R)-5-(5-((1-(3-fluoropropyl)azetidin-3-yl)amino)pyridin-2-yl)-7-methyl-7,8-dihydro-[1,3]dioxolo[4,5-g]isoquinolin-6(5H)-yl-2,2-$d_2$)propan-1-ol 13 |
| 14 | 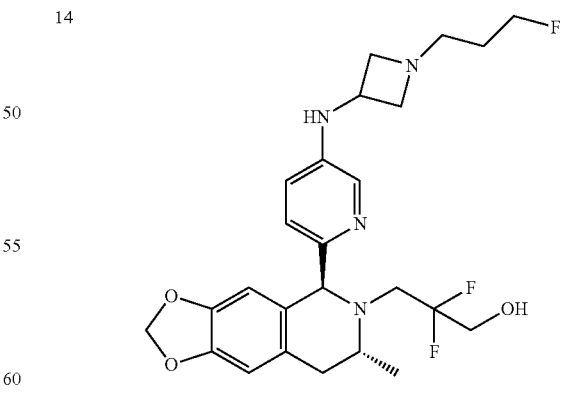

2,2-Difluoro-3-((5S,7R)-5-(5-((1-(3-fluoropropyl)azetidin-3-yl)amino)pyridin-2-yl)-7-methyl-7,8-dihydro-[1,3]dioxolo[4,5-g]isoquinolin-6(5H)-yl)propan-1-ol 14 |

| Example | Structure and name of compound |
|---|---|
| 15e | 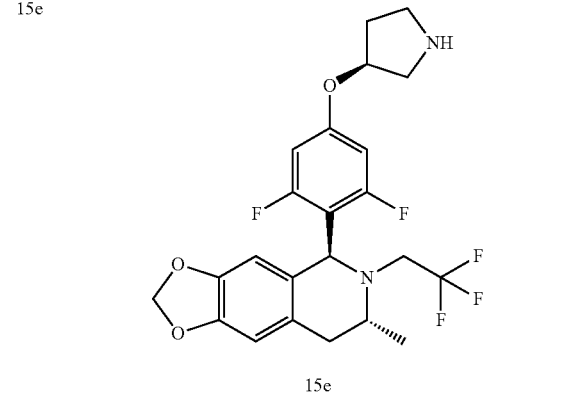<br>(5S,7R)-5-(2,6-difluoro-4-(((S)-pyrrolidin-3-yl)oxy)phenyl)-7-methyl-6-(2,2,2-trifluoroethyl)-5,6,7,8-tetrahydro-[1,3]dioxolo[4,5-g]isoquinoline 15e |
| 15 | 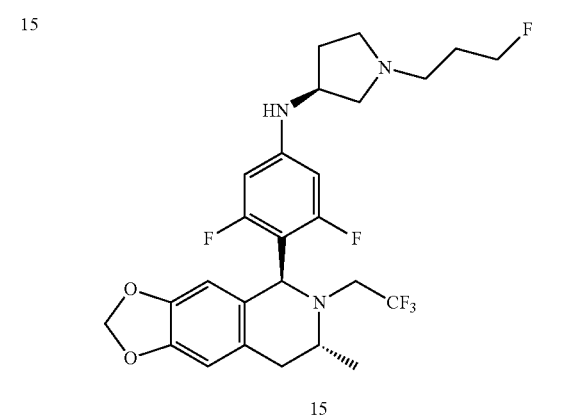<br>(5S,7R)-5-(2,6-difluoro-4-(((S)-1-(3-fluoropropyl)pyrrolidin-3-yl)oxy)phenyl)-7-methyl-6-(2,2,2-trifluoroethyl)-5,6,7,8-tetrahydro-[1,3]dioxolo[4,5-g]isoquinoline 15 |
| 16 | 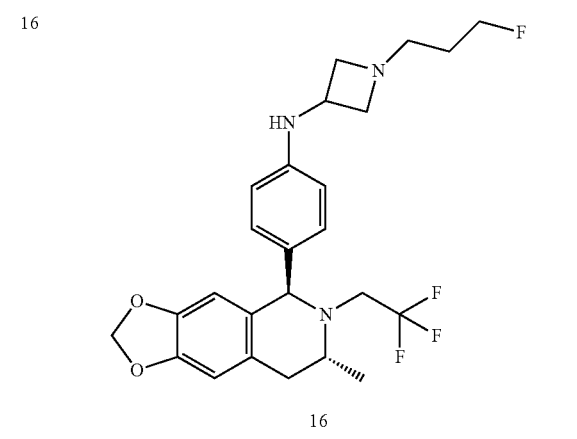<br>1-(3-Fluoropropyl)-N-(4-((5R,7R)-7-methyl-6-(2,2,2-trifluoroethyl)-5,6,7,8-tetrahydro-[1,3]dioxolo[4,5-g]isoquinolin-5-yl)phenyl)azetidin-3-amine 16 |
| 17 | 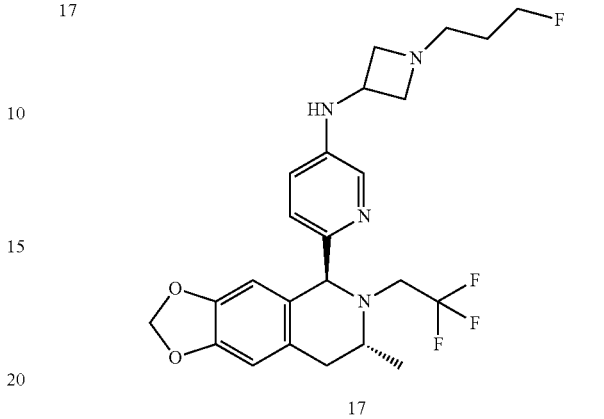<br>N-(1-(3-fluoropropyl)azetidin-3-yl)-6-((5S,7R)-7-methyl-6-(2,2,2-trifluoroethyl)-5,6,7,8-tetrahydro-[1,3]dioxolo[4,5-g]isoquinolin-5-yl)pyridin-3-amine 17 |
| 18 | 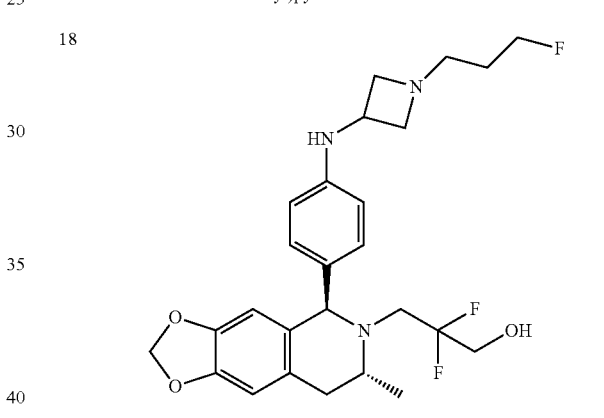<br>2,2-Difluoro-3-((5R,7R)-5-(4-((1-(3-fluoropropyl)azetidin-3-yl)amino)phenyl)-7-methyl-7,8-dihydro-[1,3]dioxolo[4,5-g]isoquinolin-6(5H)-yl)propan-1-ol 18 |
| 19 | 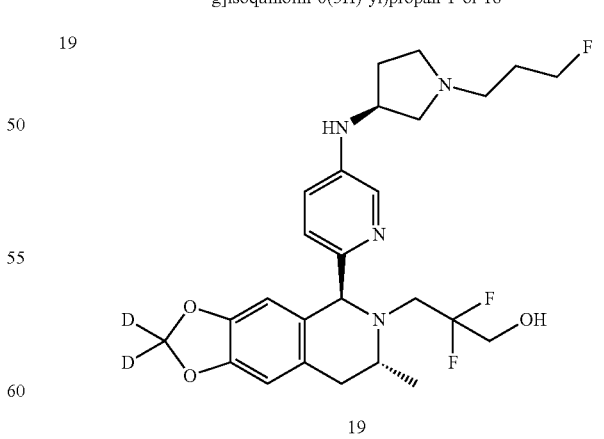<br>2,2-Difluoro-3-((5R,7R)-5-(4-(((S)-1-(3-fluoropropyl)pyrrolidin-3-yl)amino)phenyl)-7-methyl-7,8-dihydro-[1,3]dioxolo[4,5-g]isoquinolin-6(5H)-yl-2,2-d$_2$)propan-1-ol 19 |

Another aspect of the present disclosure provides a compound of general formula (IA) or a tautomer, mesomer, racemate, enantiomer or diastereomer thereof or a mixture thereof, or a pharmaceutically acceptable salt thereof,

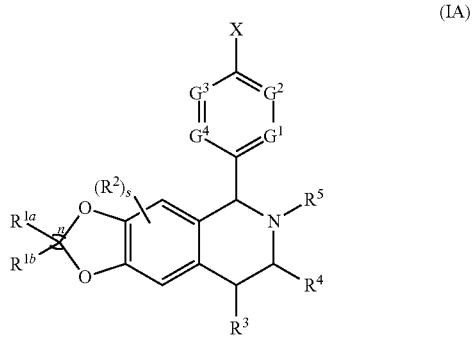

(IA)

wherein:
X is Br;
$G^1$, $G^2$, $G^3$ and $G^4$ are identical or different and are each independently $CR^8$ or a N atom;
$R^{1a}$ and $R^{1b}$ are identical or different and are each independently selected from the group consisting of hydrogen atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
$R^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
$R^3$ is selected from the group consisting of hydrogen atom, alkyl and cycloalkyl, wherein the alkyl and cycloalkyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
$R^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
$R^5$ is selected from the group consisting of alkyl, haloalkyl and cycloalkyl, wherein the alkyl and cycloalkyl are each independently optionally substituted with one or more substituents selected from the group consisting of halogen, alkyl, alkoxy, cyano, amino, nitro, carboxyl, hydroxy, hydroxyalkyl, cycloalkyl, heterocyclyl, aryl and heteroaryl;
$R^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;
n is 1, 2 or 3; and
s is 0, 1 or 2. The compound of general formula (IA) is an intermediate for the preparation of the compound of general formula (I).

Another aspect of the present disclosure provides a compound of general formula (IA) or a tautomer, mesomer, racemate, enantiomer or diastereomer thereof or a mixture thereof, or a pharmaceutically acceptable salt thereof,

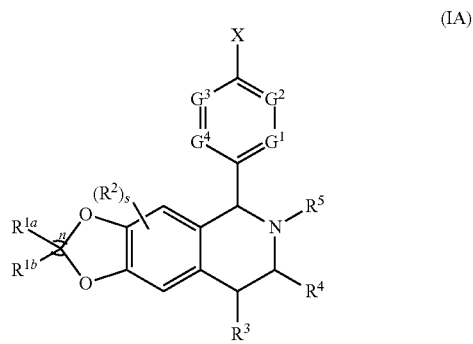

(IA)

wherein:
$R^{1a}$ and $R^{1b}$ are identical or different and are each independently selected from the group consisting of H atom, deuterium atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
X is Br;
$G^1$, $G^2$, $G^3$ and $G^4$ are identical or different and are each independently $CR^8$ or a N atom;
$R^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;
$R^3$ is selected from the group consisting of hydrogen atom, alkyl and cycloalkyl, wherein the alkyl and cycloalkyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

$R^5$ is selected from the group consisting of alkyl, haloalkyl and cycloalkyl, wherein the alkyl and cycloalkyl are each independently optionally substituted with one or more substituents selected from the group consisting of halogen, alkyl, alkoxy, cyano, amino, nitro, carboxyl, hydroxy, hydroxyalkyl, cycloalkyl, heterocyclyl, aryl and heteroaryl;

$R^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

n is 1, 2 or 3; and s is 0, 1 or 2. The compound of general formula (IA) is an intermediate for the preparation of the compound of general formula (I).

Another aspect of the present disclosure provides a compound of general formula (IA) or a tautomer, mesomer, racemate, enantiomer or diastereomer thereof or a mixture thereof, or a pharmaceutically acceptable salt thereof, which is a compound of general formula (IIA) or a tautomer, mesomer, racemate, enantiomer or diastereomer thereof or a mixture thereof, or a pharmaceutically acceptable salt thereof,

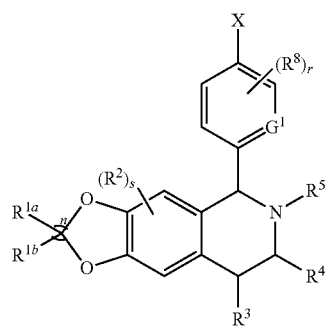

(IIA)

wherein:
X is Br;
r is 0, 1, 2 or 3;
$G^1$, $R^{1a}$, $R^{1b}$, $R^2$-$R^5$, $R^8$, n and s are as defined in the general formula (IA). The compound of general formula (IIA) is an intermediate for the preparation of the compound of general formula (II).

Another aspect of the present disclosure provides a compound of general formula (IA) or a tautomer, mesomer, racemate, enantiomer or diastereomer thereof or a mixture thereof, or a pharmaceutically acceptable salt thereof, which is a compound of general formula (IIIA) or a tautomer, mesomer, racemate, enantiomer or diastereomer thereof or a mixture thereof, or a pharmaceutically acceptable salt thereof,

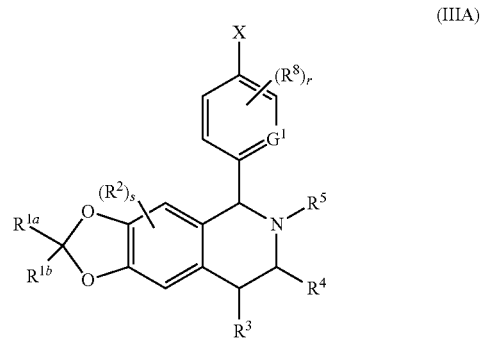

(IIIA)

wherein:
X is Br;
r is 0, 1, 2 or 3;
$G^1$, $R^{1a}$, $R^{1b}$, $R^2$-$R^5$, $R^8$ and s are as defined in the general formula (IA). The compound of general formula (IIIA) is an intermediate for the preparation of the compound of general formula (III).

Another aspect of the present disclosure provides a compound of general formula (IA) or a tautomer, mesomer, racemate, enantiomer or diastereomer thereof or a mixture thereof, or a pharmaceutically acceptable salt thereof, which is a compound of general formula (IIIaA) or a tautomer, mesomer, racemate, enantiomer or diastereomer thereof or a mixture thereof, or a pharmaceutically acceptable salt thereof,

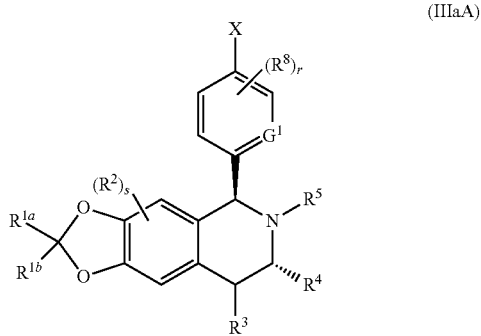

(IIIaA)

wherein:
X is Br;
r is 0, 1, 2 or 3;
$G^1$, $R^{1a}$, $R^{1b}$, $R^2$-$R^5$, $R^8$ and s are as defined in the general formula (IA). The compound of general formula (IIIaA) is an intermediate for the preparation of the compound of general formula (IIIa).

Another aspect of the present disclosure provides a compound of general formula (IA) or a tautomer, mesomer, racemate, enantiomer or diastereomer thereof or a mixture thereof, or a pharmaceutically acceptable salt thereof, which is a compound of general formula (IIGA) or (IIGaA) or a tautomer, mesomer, racemate, enantiomer or diastereomer thereof or a mixture thereof, or a pharmaceutically acceptable salt thereof,

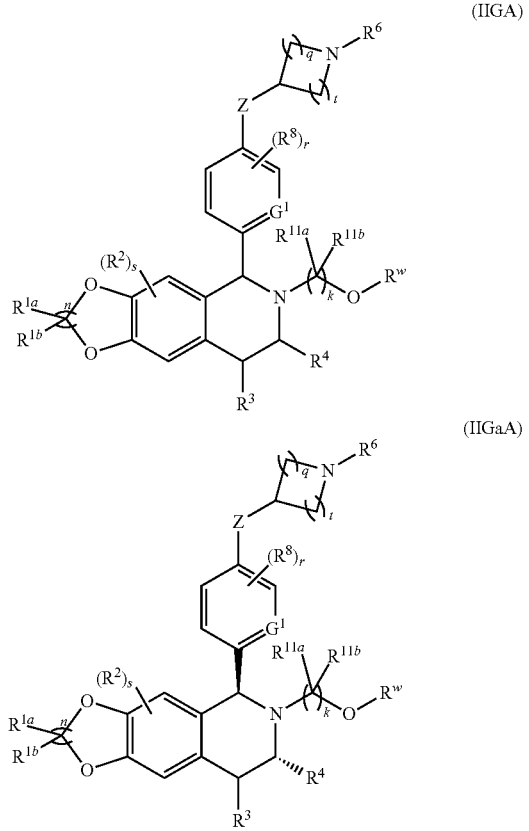

wherein:
R$^w$ is a hydroxy protective group, and is preferably

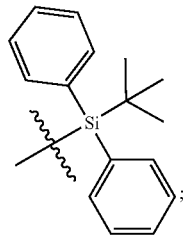 [SMILES: *[Si](c1ccccc1)(c1ccccc1)C(C)(C)C]

Z is selected from the group consisting of O atom, S atom, NR$^7$ and CR$^9$R$^{10}$;

G$^1$ is CR$^8$ or a N atom;

R$^{1a}$ and R$^{1b}$ are identical or different and are each independently selected from the group consisting of hydrogen atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

R$^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

R$^3$ is selected from the group consisting of hydrogen atom, alkyl and cycloalkyl, wherein the alkyl and cycloalkyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

R$^6$ is selected from the group consisting of hydrogen atom, alkyl, deuterated alkyl, haloalkyl, alkoxy, cyano, amino, nitro, halogen, carboxyl, carboxylate group, aldehyde, hydroxy, hydroxyalkyl, cycloalkyl and heterocyclyl, wherein the alkyl, cycloalkyl and heterocyclyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^7$ is selected from the group consisting of hydrogen atom, alkyl, haloalkyl, alkenyl, propargyl, cycloalkyl and heterocyclyl, wherein the alkyl, cycloalkyl and heterocyclyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^9$ and R$^{10}$ are identical or different and are each independently selected from the group consisting of hydrogen atom, halogen, alkyl, alkoxy, hydroxy, hydroxyalkyl, haloalkyl, alkenyl, alkynyl, cyano, cycloalkyl and heterocyclyl;

R$^{11a}$ and R$^{11b}$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl;

k is an integer from 1 to 6;
q is 1, 2 or 3;
t is 1 or 2;

n is 1, 2 or 3;

r is 0, 1, 2 or 3; and s is 0, 1 or 2.

Another aspect of the present disclosure provides a compound of general formula (IA) or a tautomer, mesomer, racemate, enantiomer or diastereomer thereof or a mixture thereof, or a pharmaceutically acceptable salt thereof, which is a compound of general formula (IIGA) or (IIGaA) or a tautomer, mesomer, racemate, enantiomer or diastereomer thereof or a mixture thereof, or a pharmaceutically acceptable salt thereof,

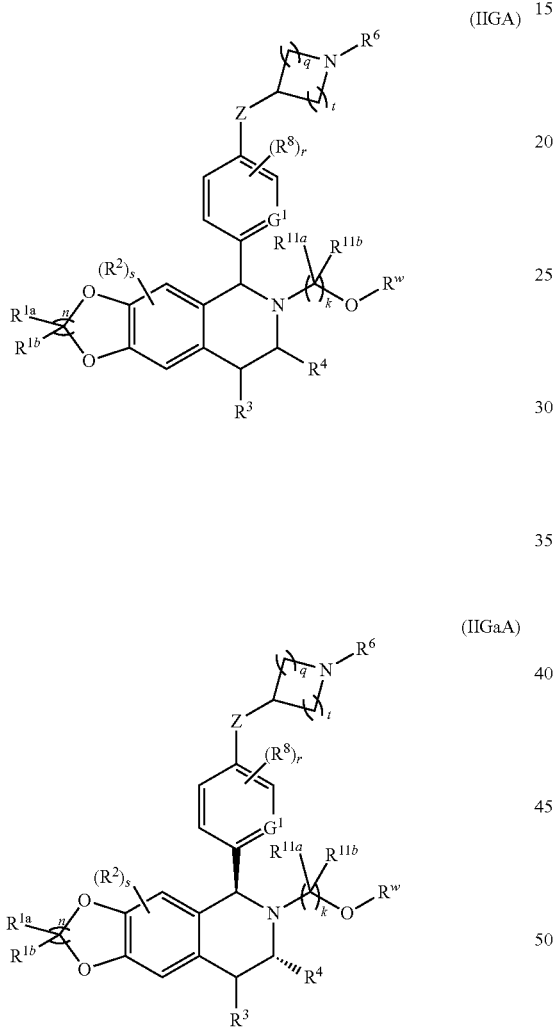

wherein:

$R^{1a}$ and $R^{1b}$ are identical or different and are each independently selected from the group consisting of H atom, deuterium atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

$R^w$ is a hydroxy protective group, and is preferably

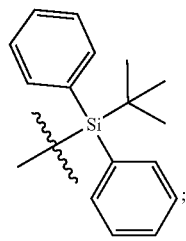 [SMILES: *[Si](c1ccccc1)(c1ccccc1)C(C)(C)C]

Z is selected from the group consisting of O atom, S atom, $NR^7$ and $CR^9R^{10}$;

$G^1$ is $CR^8$ or a N atom;

$R^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

$R^3$ is selected from the group consisting of hydrogen atom, alkyl and cycloalkyl, wherein the alkyl and cycloalkyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

$R^6$ is selected from the group consisting of hydrogen atom, alkyl, deuterated alkyl, haloalkyl, alkoxy, cyano, amino, nitro, halogen, carboxyl, carboxylate group, aldehyde, hydroxy, hydroxyalkyl, cycloalkyl and heterocyclyl, wherein the alkyl, cycloalkyl and heterocyclyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^7$ is selected from the group consisting of hydrogen atom, alkyl, haloalkyl, alkenyl, propargyl, cycloalkyl and heterocyclyl, wherein the alkyl, cycloalkyl and heterocyclyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^9$ and $R^{10}$ are identical or different and are each independently selected from the group consisting of hydrogen atom, halogen, alkyl, alkoxy, hydroxy, hydroxyalkyl, haloalkyl, alkenyl, alkynyl, cyano, cycloalkyl and heterocyclyl;

$R^{11a}$ and $R^{11b}$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl;

k is an integer from 1 to 6;

q is 1, 2 or 3;

t is 1 or 2;

n is 1, 2 or 3;

r is 0, 1, 2 or 3; and s is 0, 1 or 2.

Typical intermediate compounds described herein include, but are not limited to:

| Example | Structure and name of compound |
|---|---|
| 1h | 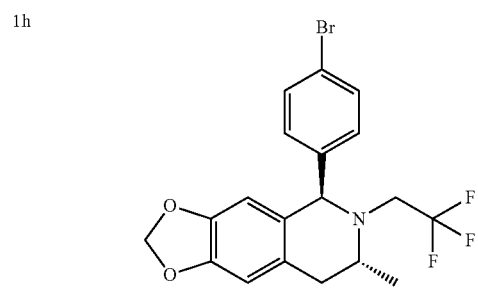<br>(5R,7R)-5-(4-bromophenyl)-7-methyl-6-(2,2,2-trifluoroethyl)-5,6,7,8-tetrahydro-[1,3]dioxolo[4,5-g]isoquinolin 1h |
| 2b | 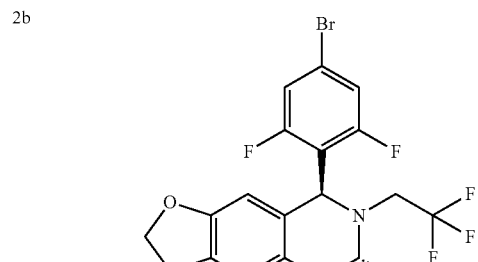<br>(5S,7R)-5-(4-bromo-2,6-difluorophenyl)-7-methyl-6-(2,2,2-trifluoroethyl)-5,6,7,8-tetrahydro-[1,3]dioxolo[4,5-g]isoquinoline 2b |
| 6b | 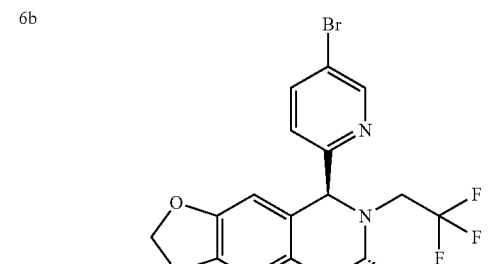<br>(5S,7R)-5-(5-bromopyridin-2-yl)-7-methyl-6-(2,2,2-trifluoroethyl)-5,6,7,8-tetrahydro-[1,3]dioxolo[4,5g]isoquinoline 6h |
| 9b | 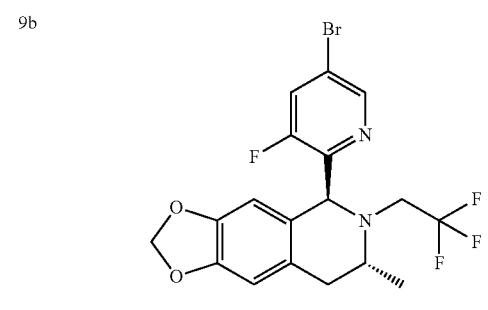<br>(5S,7R)-5-(5-bromo-3-fluoropyridin-2-yl)-7-methyl-6-(2,2,2-trifluoroethyl)-5,6,7,8-tetrahydro-[1,3]dioxolo[4,5-g]isoquinoline 9b |
| 3e | 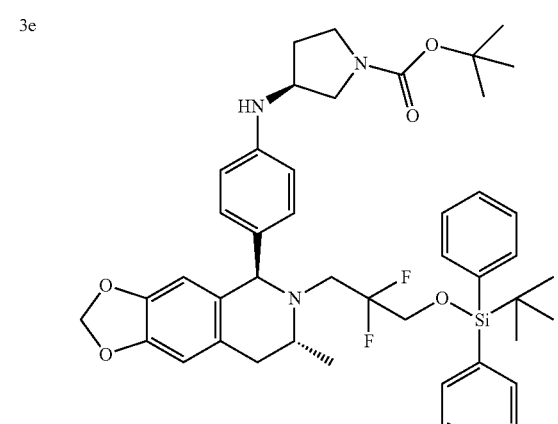<br>tert-Butyl (S)-3-((4-((5R,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)phenyl)amino)pyrrolidine-1-carboxylate 3e |

| Example | Structure and name of compound |
|---|---|
| 3f | 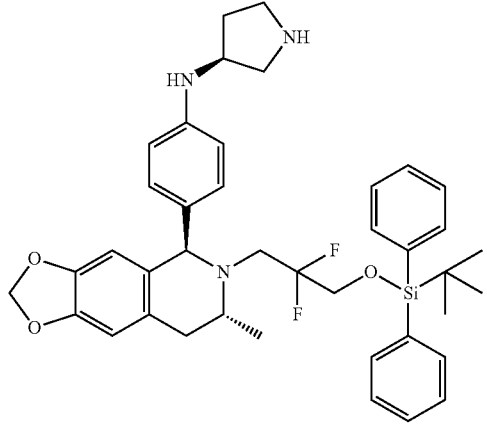<br>3f<br><br>(S)-N-(4-((5R,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)phenyl)pyrrolidin-3-amine 3f |
| 3g | 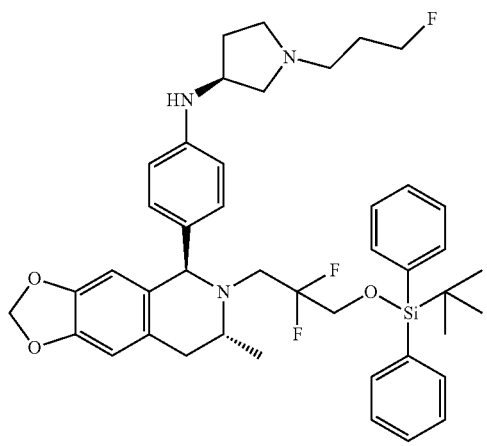<br>3g<br><br>(S)-N-(4-((5R,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)phenyl)-1-(3-fluoropropyl)pyrrolidin-3-amine 3g |
| 4c | 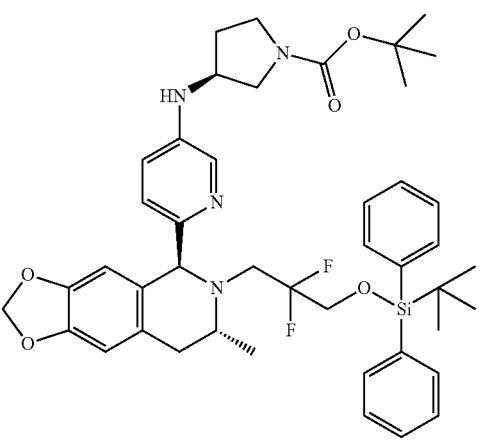<br>4c<br><br>tert-Butyl (S)-3-((6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)pyridin-3-yl)amino)pyrrolidine-1-carboxylate 4c |
| 4d | 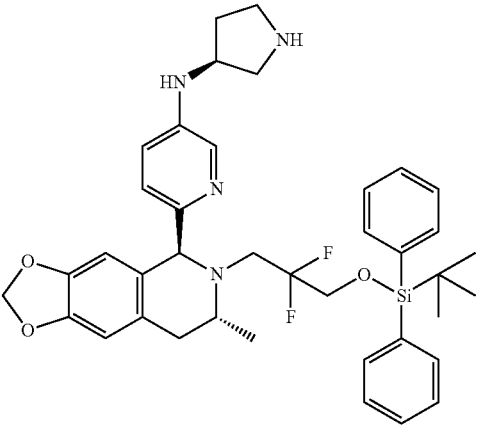<br>4d<br><br>6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-N-((S)-pyrrolidin-3-yl)pyridin-3-amine 4d |

| Example | Structure and name of compound |
|---|---|
| 4e | 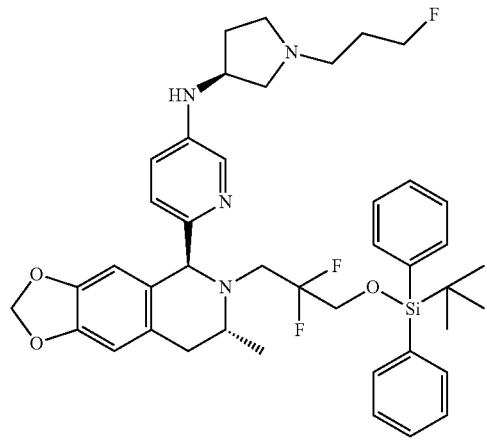

4e 6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-N-((S)-1-(3-fluoropropyl)pyrrolidin-3-yl)pyridin-3-amine 4e |
| 5c | 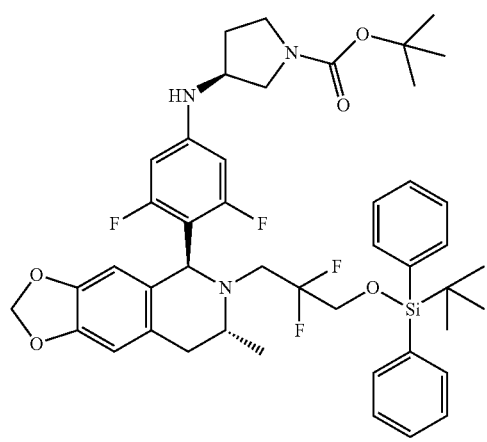

5c tert-Butyl (S)-3-((4-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-3,5-difluorophenyl)amino)pyrrolidine-1-carboxylate |
| 5d | 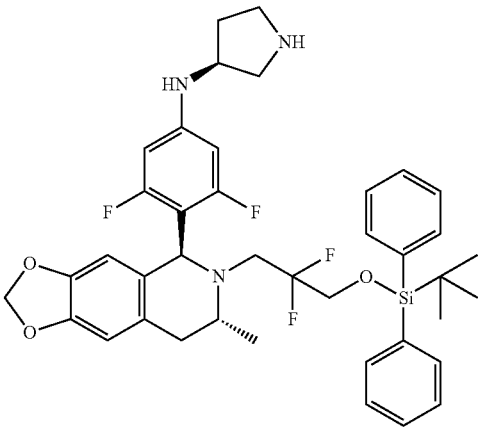

5d (S)-N-(4-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-3,5-difluorophenyl)pyrrolidin-3-amine |
| 5e | 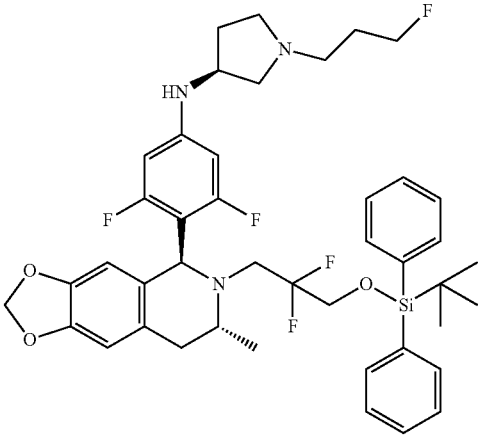

5e (S)-N-(4-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-3,5-difluorophenyl)-1-(3-fluoropropyl)pyrrolidin-3-amine |

| Example | Structure and name of compound |
|---|---|
| 11c | 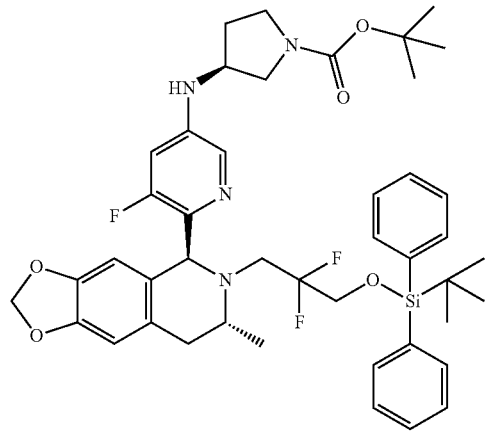

tert-Butyl (S)-3-((6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-5-fluoropyridin-3-yl)amino)pyrrolidine-1-carboxylate 11c |
| 11d | 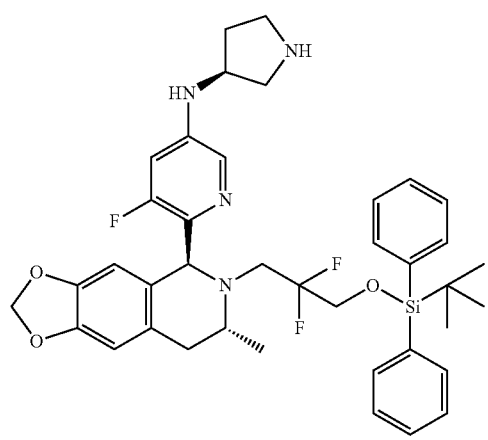

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-5-fluoro-N-((S)-pyrrolidin-3-yl)pyridin-3-amine 11d |
| 11e | 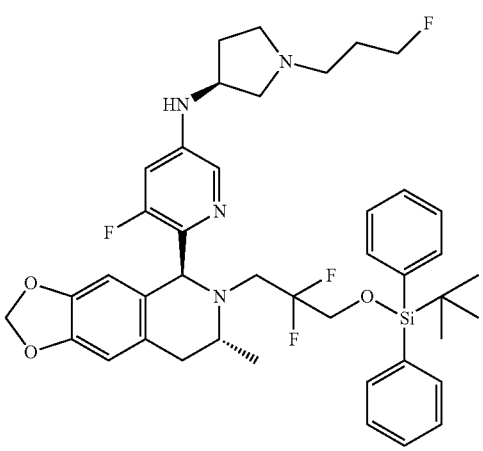

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-5-fluoro-N-((S)-1-(3-fluoropropyl)pyrrolidin-3-yl)pyridin-3-amine 11e |
| 12b | 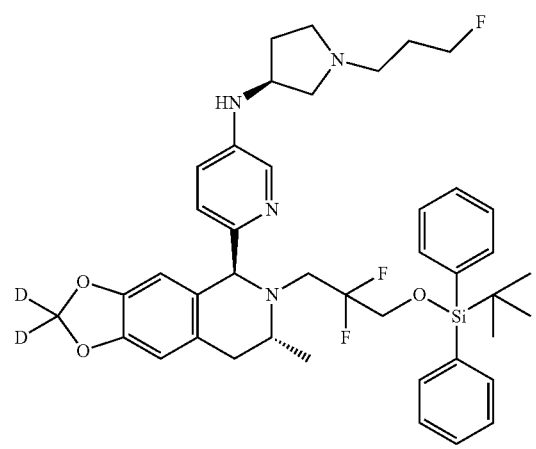

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl-2,2-$d_2$)-N-((S)-1-(3-fluoropropyl)pyrrolidin-3-yl)pyridin-3-amine 12b |

| Example | Structure and name of compound |
|---|---|
| 13a | 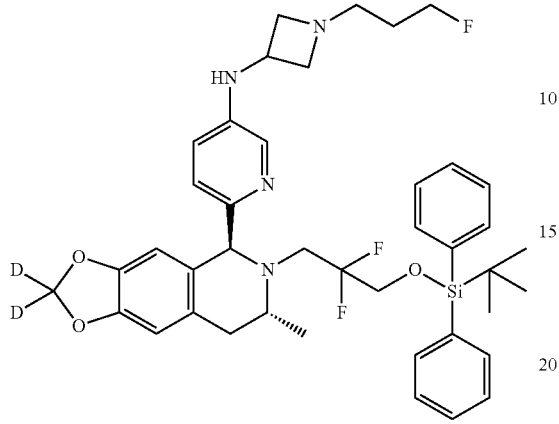

13a 6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl-2,2-d$_2$)-N-(1-(3-fluoropropyl)azetidin-3-yl)pyridin-3-amine 13a |
| 14a | 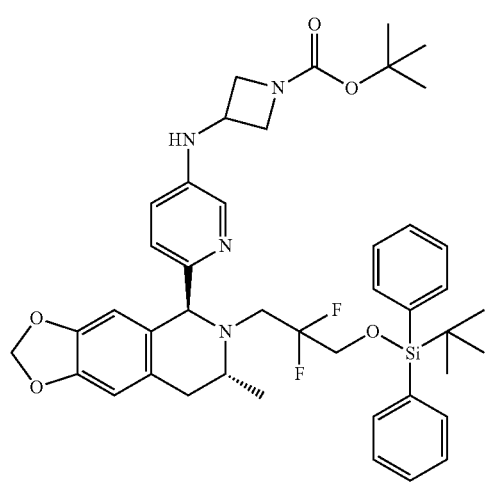

14a tert-Butyl 3-((6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)pyridin-3-yl)amino)azetidine-1-carboxylate 14a |
| 14b | 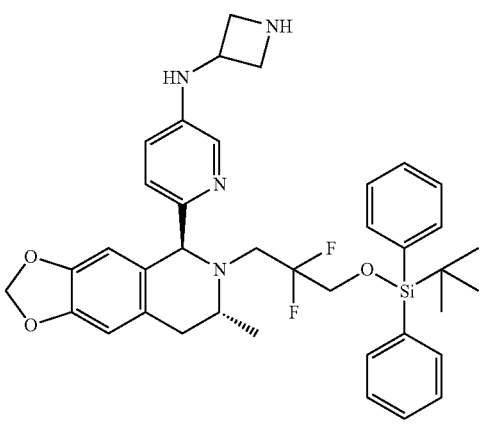

14b

N-(azetidin-3-yl)-6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)pyridin-3-amine 14b |
| 14c | 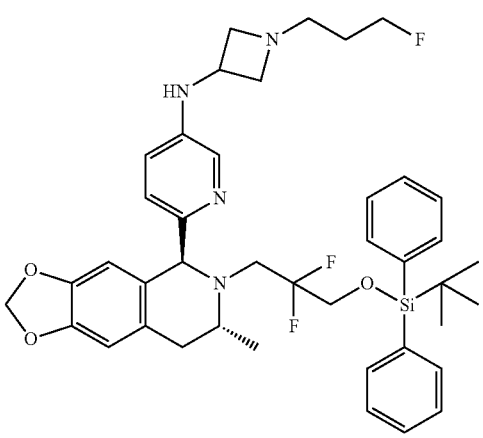

14c 6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-N-(1-(3-fluoropropyl)azetidin-3-yl)pyridin-3-amine 14c |
| 18a | 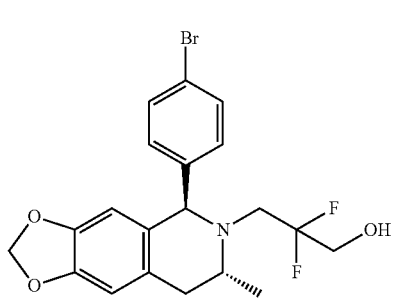

18a 3-((5R,7R)-5-(4-bromophenyl)-7-methyl-7,8-dihydro-[1,3]dioxolo[4,5-g]isoquinolin-6(5H)-yl)-2,2-difluoropropan-1-ol 18a |

-continued

| Example | Structure and name of compound |
|---|---|
| 19b | 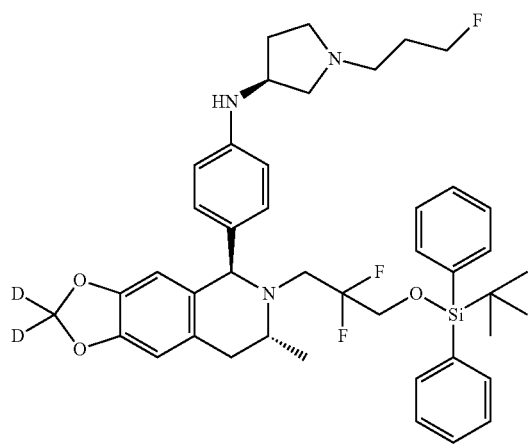

19b (S)-N-(4-((5R,7R)-6-(3-((tert-butyldiphenylsilyl)oxy)-2,2-difluoro-propyl)-7-methyl-5,6,7,8-tetrahydro-[1,3]dioxolo[4,5-g]isoquinolin-5-yl-2,2-d₂)phenyl)-1-(3-fluoropropyl)pyrrolidin-3-amine 19b |

Another aspect of the present disclosure provides a method for preparing the compound of general formula (I) or the tautomer, mesomer, racemate, enantiomer or diastereomer thereof or the mixture thereof, or the pharmaceutically acceptable salt thereof, comprising the following step:

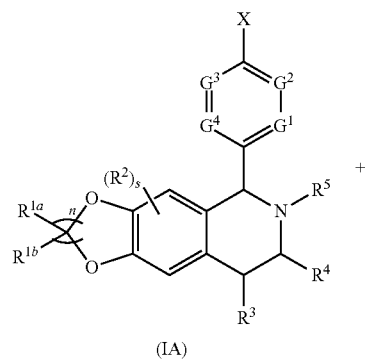

(IA)

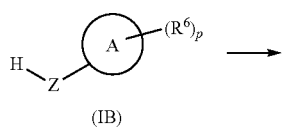

(IB)

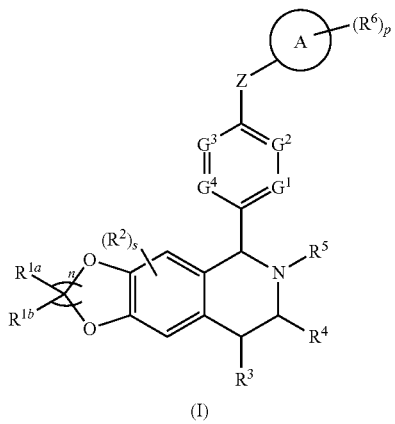

(I)

subjecting a compound of general formula (IA) and a compound of general formula (IB) to a coupling reaction to give the compound of general formula (I), wherein:

X is Br;

ring A, Z, $G^1$, $G^2$, $G^3$, $G^4$, $R^{1a}$, $R^{1b}$, $R^2$-$R^6$, p, n and s are as defined in the compound of general formula (I).

Another aspect of the present disclosure provides a method for preparing the compound of general formula (II) or the tautomer, mesomer, racemate, enantiomer or diastereomer thereof or the mixture thereof, or the pharmaceutically acceptable salt thereof, comprising the following step:

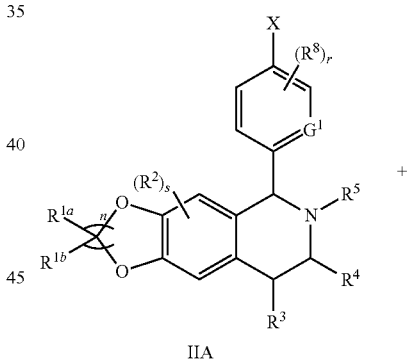

IIA

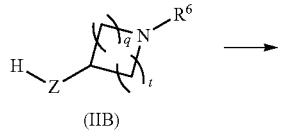

(IIB)

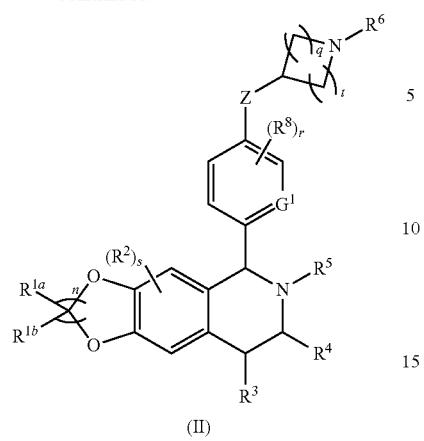

(II)

subjecting a compound of general formula (IIA) and a compound of general formula (IIB) to a coupling reaction to give the compound of general formula (II), wherein:

X is Br;

$G^1$, Z, $R^{1a}$, $R^{1b}$, $R^2$-$R^6$, $R^8$, r, q, t, n and s are as defined in the compound of general formula (II).

Another aspect of the present disclosure provides a method for preparing the compound of general formula (III) or the tautomer, mesomer, racemate, enantiomer or diastereomer thereof or the mixture thereof, or the pharmaceutically acceptable salt thereof, comprising the following step:

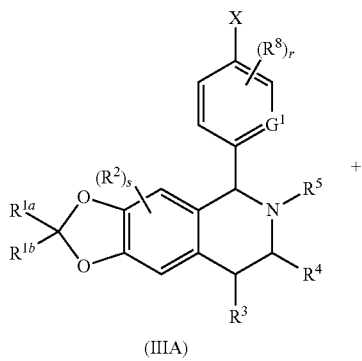

(IIIA)

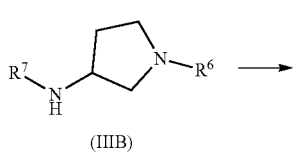

(IIIB)

subjecting a compound of general formula (IIIA) and a compound of general formula (IIIB) to a coupling reaction to give the compound of general formula (III), wherein:

X is Br;

$G^1$, $R^{1a}$, $R^{1b}$, $R^2$-$R^8$, r and s are as defined in the compound of general formula (III).

Another aspect of the present disclosure provides a method for preparing the compound of general formula (IIIa) or the tautomer, mesomer, racemate, enantiomer or diastereomer thereof or a mixture thereof, or the pharmaceutically acceptable salt thereof, comprising the following step:

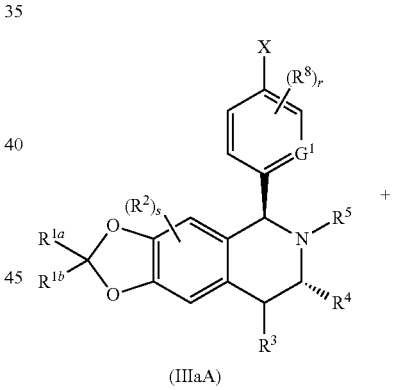

(IIIaA)

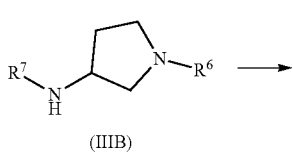

(IIIB)

-continued

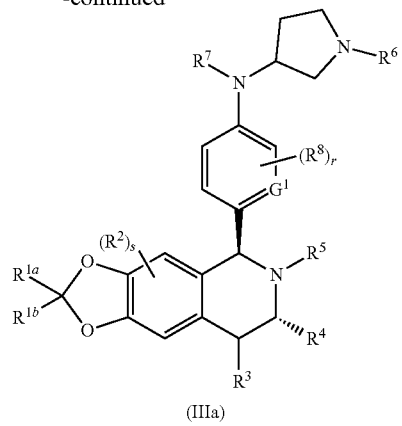

(IIIa)

subjecting a compound of general formula (IIIaA) and a compound of general formula (IIIB) to a coupling reaction to give the compound of general formula (IIIa), wherein:

X is Br;

$G^1$, $R^{1a}$, $R^{1b}$, $R^2$-$R^8$, r and s are as defined in the compound of general formula (IIIa).

Another aspect of the present disclosure provides a method for preparing the compound of general formula (IIG) or (IIGa) or the tautomer, mesomer, racemate, enantiomer or diastereomer thereof or the mixture thereof, or the pharmaceutically acceptable salt thereof, comprising the following step:

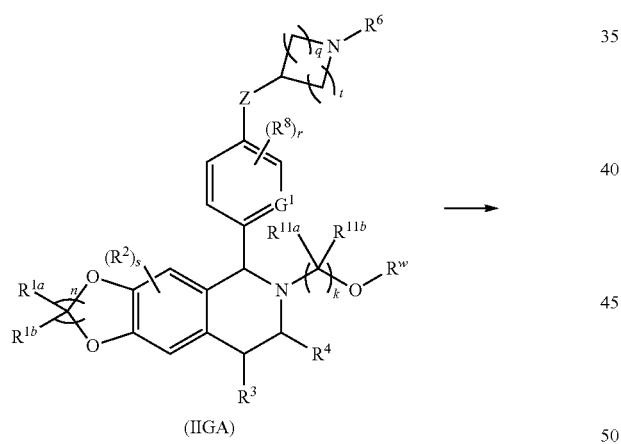

(IIGA)

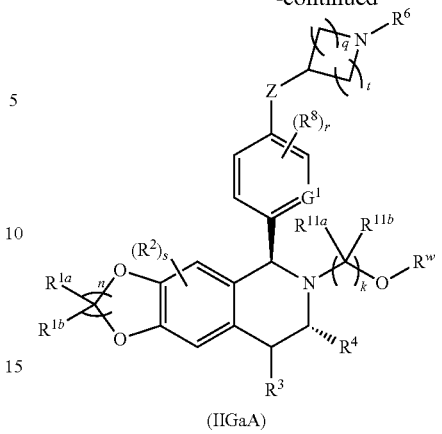

(IIGaA)

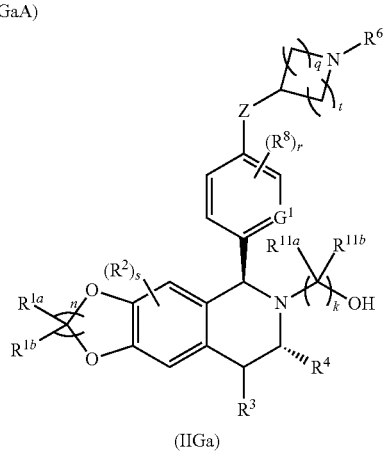

(IIGa)

removing a hydroxy protective group from a compound of general formula (IIGA) to give the compound of general formula (IIG), or removing a hydroxy protective group from a compound of general formula (IIGaA) to give the compound of general formula (IIGa), wherein:

$R^w$ is a hydroxy protective group, and is preferably

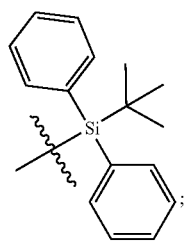 [SMILES: *[Si](c1ccccc1)(c1ccccc1)C(C)(C)C]

Z, $G^1$, $R^{1a}$, $R^{1b}$, $R^2$-$R^4$, $R^6$, $R^8$, $R^{11a}$, $R^{11b}$, q, t, k, r, n and s are as defined in the compound of general formula (IIG).

Another aspect of the present disclosure relates to a pharmaceutical composition comprising a therapeutically effective amount of the compound of general formula (I) or the tautomer, mesomer, racemate, enantiomer or diastereomer thereof or the mixture thereof, or the pharmaceutically acceptable salt thereof, and one or more pharmaceutically acceptable carriers, diluents or excipients. The present disclosure also relates to a method for preparing the (IIG)

above pharmaceutical composition, which comprises mixing the compounds of various general formulas or the tautomers, mesomers, racemates, enantiomers or diastereomers thereof or the mixtures thereof, or the pharmaceutically acceptable salts thereof, with the pharmaceutically acceptable carriers, diluents or excipients.

Another aspect of the present disclosure relates to use of the compound of general formula (I) or the tautomer, mesomer, racemate, enantiomer or diastereomer thereof or the mixture thereof, or the pharmaceutically acceptable salt thereof, or the pharmaceutical composition comprising the same in preparing an estrogen receptor modulator, preferably in preparing a selective estrogen receptor degrader (SERD).

Another aspect of the present disclosure relates to use of the compound of general formula (I) or the tautomer, mesomer, racemate, enantiomer or diastereomer thereof or the mixture thereof, or the pharmaceutically acceptable salt thereof, or the pharmaceutical composition comprising the same in preparing a medicament for preventing and/or treating cancer, wherein the cancer is preferably selected from the group consisting of breast cancer, endometrial cancer, cervical cancer, skin cancer, prostate cancer, ovarian cancer, fallopian tube tumor, ovarian tumor, hemophilia and leukemia, more preferably from the group consisting of breast cancer, ovarian cancer, endometrial cancer, prostate cancer and uterine cancer, and most preferably from breast cancer.

Another aspect of the present disclosure relates to use of the compound of general formula (I) or the tautomer, mesomer, racemate, enantiomer or diastereomer thereof or the mixture thereof, or the pharmaceutically acceptable salt thereof, or the pharmaceutical composition comprising the same in preparing a medicament for preventing and/or treating an estrogen receptor-mediated or -dependent disease or condition, wherein the estrogen receptor-mediated or -dependent disease or condition is preferably selected from the group consisting of cancer, central nervous system deficit, cardiovascular system deficit, blood system deficit, immune and inflammatory disease, susceptible infection, metabolic deficit, neurologic deficit, psychiatric deficit and reproductive deficit; the cancer is preferably selected from the group consisting of breast cancer, endometrial cancer, uterine cancer, cervical cancer, skin cancer, prostate cancer, ovarian cancer, fallopian tube tumors, hemophilia and leukemia, more preferably from the group consisting of breast cancer, ovarian cancer, endometrial cancer, prostate cancer and uterine cancer, and most preferably from breast cancer; the central nervous system (CNS) deficit may be alcoholism or migraine; the cardiovascular system deficit may be aortic aneurysm, susceptibility to myocardial infarction, aortic valve sclerosis, cardiovascular disease, coronary artery disease or hypertension; the blood system deficit may be deep vein thrombosis; the immune and inflammatory disease may be Graves' disease, arthritis, multiple sclerosis or liver cirrhosis; the susceptibility to infections may be hepatitis B or chronic liver disease; the metabolic deficit may be cholestasis, hypospadias, obesity, osteoarthritis, osteopenia or osteoporosis; the neurologic deficit may be Alzheimer's disease, Parkinson's disease, migraine or vertigo; the psychiatric deficit may be anorexia nervosa, attention deficit hyperactivity disorder (ADHD), dementia, major depressive disorder or psychosis; and the reproductive deficit may be age of menarche, endometriosis, infertility, etc.

Another aspect of the present disclosure relates to a method for treating cancer, which comprises administering to a patient in need thereof a therapeutically effective dose of the compound of general formula (I) or the tautomer, mesomer, racemate, enantiomer or diastereomer thereof or the mixture thereof, or the pharmaceutically acceptable salt thereof, or the pharmaceutical composition comprising the same of the present disclosure. The method has a remarkable therapeutic effect and fewer side effects. The cancer is preferably selected from the group consisting of breast cancer, endometrial cancer, cervical cancer, skin cancer, prostate cancer, ovarian cancer, fallopian tube tumor, ovarian tumor, hemophilia and leukemia, more preferably from the group consisting of breast cancer, ovarian cancer, endometrial cancer, prostate cancer and uterine cancer, and most preferably from breast cancer.

Another aspect of the present disclosure relates to a method for treating an estrogen receptor-mediated or -dependent disease, which comprises administering to a patient in need thereof a therapeutically effective dose of the compound of general formula (I) or the tautomer, mesomer, racemate, enantiomer or diastereomer thereof or the mixture thereof, or the pharmaceutically acceptable salt thereof, or the pharmaceutical composition comprising the same of the present disclosure. The method has a remarkable therapeutic effect and fewer side effects. The estrogen receptor-mediated or -dependent disease or condition is preferably selected from the group consisting of cancer, central nervous system deficit, cardiovascular system deficit, blood system deficit, immune and inflammatory disease, susceptible infection, metabolic deficit, neurologic deficit, psychiatric deficit and reproductive deficit. The cancer is preferably selected from the group consisting of breast cancer, endometrial cancer, uterine cancer, cervical cancer, skin cancer, prostate cancer, ovarian cancer, fallopian tube tumors, hemophilia and leukemia, more preferably from the group consisting of breast cancer, ovarian cancer, endometrial cancer, prostate cancer and uterine cancer, and most preferably from breast cancer; the central nervous system (CNS) deficit may be alcoholism or migraine; the cardiovascular system deficit may be aortic aneurysm, susceptibility to myocardial infarction, aortic valve sclerosis, cardiovascular disease, coronary artery disease or hypertension; the blood system deficit may be deep vein thrombosis; the immune and inflammatory disease may be Graves' disease, arthritis, multiple sclerosis or liver cirrhosis; the susceptibility to infections may be hepatitis B or chronic liver disease; the metabolic deficit may be cholestasis, hypospadias, obesity, osteoarthritis, osteopenia or osteoporosis; the neurologic deficit may be Alzheimer's disease, Parkinson's disease, migraine or vertigo; the psychiatric deficit may be anorexia nervosa, attention deficit hyperactivity disorder (ADHD), dementia, major depressive disorder or psychosis; and the reproductive deficit may be age of menarche, endometriosis, infertility, etc.

Another aspect of the present disclosure relates to the compound of general formula (I) or the tautomer, mesomer, racemate, enantiomer or diastereomer thereof or the mixture thereof, or the pharmaceutically acceptable salt thereof disclosed herein, or the pharmaceutical composition comprising the same of the present disclosure for use as a medicament.

Another aspect of the present disclosure relates to the compound of general formula (I) or the tautomer, mesomer, racemate, enantiomer or diastereomer thereof or the mixture thereof, or the pharmaceutically acceptable salt thereof disclosed herein, or the pharmaceutical composition comprising the same of the present disclosure for use as a medicament for treating cancer, wherein the cancer may be selected from the group consisting of breast cancer, endometrial cancer, cervical cancer, skin cancer, prostate cancer, ovarian cancer, fallopian tube tumor, ovarian tumor, hemophilia and leukemia, more preferably from the group consisting of breast cancer, ovarian cancer, endometrial cancer, prostate cancer and uterine cancer, and most preferably from breast cancer.

Another aspect of the present disclosure relates to the compound of general formula (I) or the tautomer, mesomer, racemate, enantiomer or diastereomer thereof or the mixture thereof, or the pharmaceutically acceptable salt thereof, or the pharmaceutical composition comprising the same of the present disclosure for use as a medicament for treating an estrogen receptor-mediated or -dependent disease or condition, wherein the estrogen receptor-mediated or -dependent disease or condition is preferably selected from the group consisting of cancer, central nervous system deficit, cardiovascular system deficit, blood system deficit, immune and inflammatory disease, susceptible infection, metabolic deficit, neurologic deficit, psychiatric deficit and reproductive deficit; the cancer is preferably selected from the group consisting of breast cancer, endometrial cancer, uterine cancer, cervical cancer, skin cancer, prostate cancer, ovarian cancer, fallopian tube tumors, hemophilia and leukemia, more preferably from the group consisting of breast cancer, ovarian cancer, endometrial cancer, prostate cancer and uterine cancer, and most preferably from breast cancer; the central nervous system (CNS) deficit may be alcoholism or migraine; the cardiovascular system deficit may be aortic aneurysm, susceptibility to myocardial infarction, aortic valve sclerosis, cardiovascular disease, coronary artery disease or hypertension; the blood system deficit may be deep vein thrombosis; the immune and inflammatory disease may be Graves' disease, arthritis, multiple sclerosis or liver cirrhosis; the susceptibility to infections may be hepatitis B or chronic liver disease; the metabolic deficit may be cholestasis, hypospadias, obesity, osteoarthritis, osteopenia or osteoporosis; the neurologic deficit may be Alzheimer's disease, Parkinson's disease, migraine or vertigo; the psychiatric deficit may be anorexia nervosa, attention deficit hyperactivity disorder (ADHD), dementia, major depressive disorder or psychosis; and the reproductive deficit may be age of menarche, endometriosis, infertility, etc.

The active compound may be formulated into a form suitable for administration by any suitable route, preferably in a form of a unit dose, or in a form of a single dose that can be self-administered by a patient. The unit dose of the compound or composition of the present disclosure may be in a tablet, capsule, cachet, vial, powder, granule, lozenge, suppository, regenerating powder or liquid formulation.

The dosage of the compound or composition used in the treatment method of the present disclosure will generally vary with the severity of the disease, the weight of the patient, and the relative efficacy of the compound. However, as a general guide, a suitable unit dose may be 0.1 to 1000 mg.

The pharmaceutical composition of the present disclosure may comprise, in addition to the active compound, one or more auxiliary materials selected from the group consisting of filler (diluent), binder, wetting agent, disintegrant, excipient, and the like. Depending on the method of administration, the compositions may comprise 0.1 to 99 wt. % of the active compound.

The pharmaceutical composition comprising the active ingredient may be in a form suitable for oral administration, for example, in the form of a tablet, a dragee, a lozenge, an aqueous or oil suspension, a dispersible powder or granule, an emulsion, a hard or soft capsule, or a syrup or elixir. Oral compositions can be prepared according to any method known in the art for preparing pharmaceutical compositions and may comprise one or more ingredients selected from the group consisting of sweetener, corrigent, colorant and preservative, so as to provide a pleasant-to-eye and palatable pharmaceutical formulation. The tablet comprises the active ingredient and a non-toxic pharmaceutically acceptable excipient which is used for mixing and is suitable for the preparation of the tablet.

The aqueous suspension comprises an active substance and an excipient which is used for mixing and suitable for the preparation of the aqueous suspension. The aqueous suspension may also comprise one or more preservatives, for example ethylparaben or n-propylparaben, one or more colorants, one or more corrigents and one or more sweeteners. The oil suspension may be formulated by suspending the active ingredient in a vegetable oil. The oil suspension may comprise a thickening agent. The sweeteners and corrigents described above may be added to provide a palatable formulation.

The dispersible powder and granule suitable for the preparation of an aqueous suspension can be allowed to provide the active ingredient, and a dispersant or a wetting agent, a suspending agent or one or more preservatives for mixing, by adding water. The description above can be exemplified by suitable dispersants or wetting agents and suspending agents. Other excipients, such as sweeteners, corrigents and colorants, may also be added. Antioxidants such as ascorbic acid are added to preserve these compositions.

The pharmaceutical composition disclosed herein may also be in the form of an oil-in-water emulsion.

The pharmaceutical composition may be in the form of a sterile injectable aqueous solution. Available and acceptable vehicles or solvents include water, Ringer's solution and isotonic sodium chloride solution. The sterile injectable formulation may be a sterile injectable oil-in-water microemulsion in which the active ingredient is dissolved in the oil phase. For example, the active ingredient is dissolved in a mixture of soybean oil and lecithin. The oil solution is then treated in a mixture of water and glycerol to form a microemulsion. The injection or microemulsion can be locally injected into the bloodstream of a patient in large quantities. Alternatively, it may be desirable to administer solutions and microemulsions in such a way as to maintain a constant circulating concentration of the compound of the present disclosure. To maintain such a constant concentration, a continuous intravenous delivery device may be used. An example of such a device is a Deltec CADD-PLUS™ 5400 intravenous injection pump.

The pharmaceutical composition may be in the form of a sterile injectable aqueous or oily suspension for intramuscular and subcutaneous administration. The suspension can be prepared according to the prior art by using those suitable dispersants or wetting agents and suspending agents described above. The sterile injectable formulation may also be a sterile injection or suspension prepared in a parenterally acceptable non-toxic diluent or solvent. In addition, a sterile fixed oil may be conveniently used as a solvent or a suspending medium.

The compound of the present disclosure may be administered in the form of a suppository for rectal administration. Such a pharmaceutical composition can be prepared by mixing a drug with a suitable non-irritating excipient which is a solid at ambient temperature but a liquid in the rectum and therefore will melt in the rectum to release the drug. Such materials include cocoa butter, glycerogelatin, hydrogenated vegetable oils, polyethylene glycols of various molecular weights and mixtures of fatty acid esters of polyethylene glycols.

As is well known to those skilled in the art, the dosage of the drug administered depends on a variety of factors, including but not limited to, the activity of the particular compound employed, the age of the patient, the weight of the patient, the health condition of the patient, the behavior of the patient, the diet of the patient, the time of administration, the route of administration, the rate of excretion, the combination of drugs, and the like. In addition, the optimal treatment regimen, such as the mode of administration, the daily dose of the compound of general formula (I) or the type of pharmaceutically acceptable salts, can be verified according to conventional treatment regimens.

DETAILED DESCRIPTION OF THE INVENTION

Unless otherwise stated, the terms used in the specification and claims have the following meanings.

The term "alkyl" refers to a saturated aliphatic hydrocarbon group which is a linear or branched group containing 1 to 20 carbon atoms, preferably to an alkyl group containing 1 to 12 (e.g., 1, 2, 3, 4, 5, 6, 7, 8, 9, 10, 11 and 12) carbon atoms, and more preferably to an alkyl group containing 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various side-chain isomers thereof, etc. More preferred is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted, and when it is substituted, the substituent may be substituted at any available connection site, and the substituent is preferably one or more of the following groups; it is substituted with one or more substituents independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "alkenyl" refers to an alkyl compound containing at least one carbon-carbon double bond in the molecule, wherein the alkyl is as defined above. The alkenyl is a linear or branched group containing 2 to 20 carbon atoms, preferably 2 to 12 (e.g., 2, 3, 4, 5, 6, 7, 8, 9, 10, 11 and 12) carbon atoms, and more preferably 2 to 6 carbon atoms. The alkenyl may be substituted or unsubstituted, and when it is substituted, the substituent is preferably one or more of the following groups; it is substituted with one or more substituents independently selected from the group consisting of hydrogen atom, alkyl, alkoxy, halogen, haloalkyl, hydroxy, hydroxyalkyl, cyano, amino, nitro, cycloalkyl, heterocyclyl, aryl and heteroaryl.

The term "alkynyl" refers to an alkyl compound containing at least one carbon-carbon triple bond in the molecule, wherein the alkyl is as defined above. The alkynyl is a linear or branched group containing 2 to 20 carbon atoms, preferably 2 to 12 (e.g., 2, 3, 4, 5, 6, 7, 8, 9, 10, 11 and 12) carbon atoms, and more preferably 2 to 6 carbon atoms. Non-limiting examples of the alkynyl include, but are not limited to —C≡CH, —CH$_2$C≡CH, —CH$_2$C≡CCH$_3$, —C≡CCH$_2$CH$_3$, —CH$_2$C≡CCH$_2$CH$_3$, —C≡CCH(CH$_3$)$_2$, —C(CH$_3$)$_2$C≡CH, —C(CH$_3$)$_2$C≡CCH$_3$ and the like. The alkynyl may be substituted or unsubstituted, and when it is substituted, the substituent is preferably one or more of the following groups; it is substituted with one or more substituents preferably independently selected from the group consisting of hydrogen atom, alkyl, alkoxy, halogen, haloalkyl, hydroxy, hydroxyalkyl, cyano, amino, nitro, cycloalkyl, heterocyclyl, aryl and heteroaryl.

The term "alkylene" refers to a saturated linear or branched aliphatic hydrocarbon group having 2 residues derived from the parent alkane by removal of two hydrogen atoms from the same carbon atom or two different carbon atoms, which is a linear or branched group containing 1 to 20 carbon atoms, preferably an alkylene group containing 1 to 12 (e.g., 1, 2, 3, 4, 5, 6, 7, 8, 9, 10, 11 and 12) carbon atoms, and more preferably an alkylene group containing 1 to 6 carbon atoms. Non-limiting examples of the alkylene include, but are not limited to, methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—) and the like. The alkylene may be substituted or unsubstituted, and when it is substituted, the substituent may be substituted at any available connection site with one or more substituents preferably independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkoxy" refers to —O-(alkyl) and —O-(unsubstituted cycloalkyl), wherein the alkyl is as defined above. Non-limiting examples of alkoxy include: methoxy, ethoxy, propoxy, butoxy, cyclopropyloxy, cyclobutoxy, cyclopentyloxy, cyclohexyloxy. The alkoxy may be optionally substituted or unsubstituted, and when it is substituted, the substituent is preferably one or more of the following groups; it is substituted with one or more substituents independently selected from the group consisting of hydrogen atom, halogen, alkyl, alkoxy, haloalkyl, hydroxy, hydroxyalkyl, cyano, amino, nitro, cycloalkyl, heterocyclyl, aryl and heteroaryl.

The term "cycloalkyl" refers to a saturated or partially unsaturated monocyclic or polycyclic hydrocarbon substituent. The cycloalkyl ring contains 3 to 20 carbon atoms, preferably 3 to 12 (e.g., 3, 4, 5, 6, 7, 8, 9, 10, 11 and 12) carbon atoms, more preferably 3 to 8 carbon atoms, and most preferably 3 to 6 (e.g., 3, 4, 5 or 6) carbon atoms. Non-limiting examples of the monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like, preferably cycloalkyl. Polycyclic cycloalkyl includes spiro cycloalkyl, fused cycloalkyl, and bridged cycloalkyl.

The term "spiro cycloalkyl" refers to a 5- to 20-membered polycyclic group in which monocyclic rings share one carbon atom (referred to as the spiro atom), wherein the spiro cycloalkyl may contain one or more double bonds. The spiro cycloalkyl is preferably 6- to 14-membered, more preferably 7- to 10-membered (e.g., 7, 8, 9 and 10-membered). According to the number of the spiro atoms shared among the rings, the spiro cycloalkyl may be monospiro cycloalkyl, bispiro cycloalkyl or polyspiro cycloalkyl, preferably monospiro cycloalkyl and bispiro cycloalkyl, more preferably 4-membered/4-membered, 4-membered/5-membered, 4-membered/6-membered, 5-membered/5-membered or 5-membered/6-membered monospiro cycloalkyl. Non-limiting examples of the spiro cycloalkyl include:

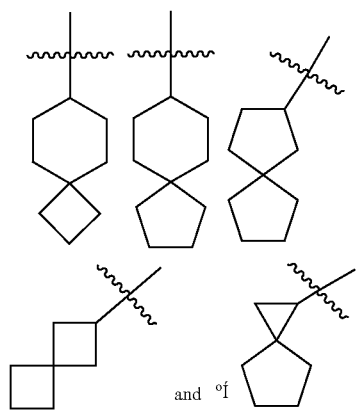

The term "fused cycloalkyl" refers to a 5- to 20-membered carbon polycyclic group in which each ring shares a pair of adjacent carbon atoms with the other rings in the system, wherein one or more of the rings may contain one or more double bonds. The fused cycloalkyl is preferably 6- to 14-membered, more preferably 7- to 10-membered (e.g., 7, 8, 9 and 10-membered). According to the number of the formed rings, the fused cycloalkyl may be bicyclic, tricyclic, tetracyclic or polycyclic cycloalkyl, preferably bicyclic or tricyclic cycloalkyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic cycloalkyl. Non-limiting examples of the fused cycloalkyl include:

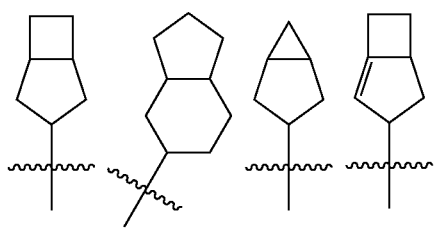

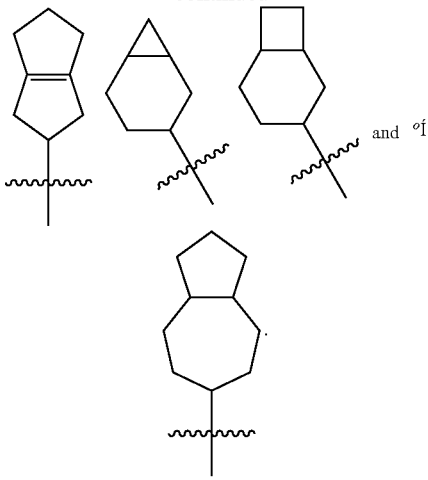

The term "bridged cycloalkyl" refers to a 5- to 20-membered carbon polycyclic group in which any two rings share two carbon atoms that are not directly connected to each other, wherein the bridged cycloalkyl may contain one or more double bonds. The bridged cycloalkyl is preferably 6- to 14-membered, more preferably 7- to 10-membered (e.g., 7, 8, 9 and 10-membered). According to the number of the formed rings, the bridged cycloalkyl may be bicyclic, tricyclic, tetracyclic or polycyclic, preferably bicyclic, tricyclic or tetracyclic, and more preferably bicyclic or tricyclic. Non-limiting examples of the bridged cycloalkyl include:

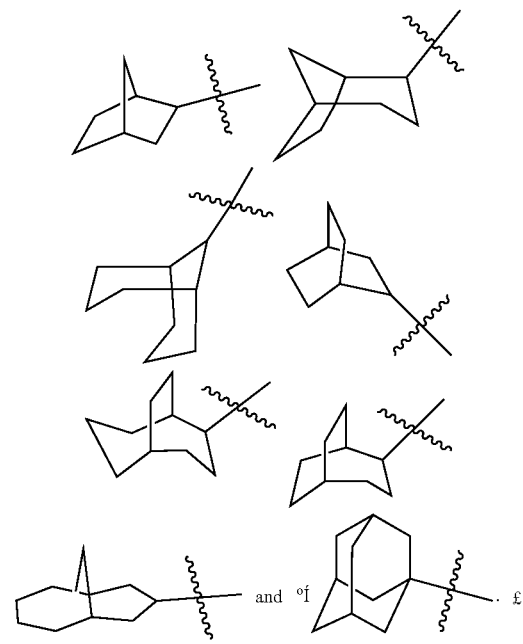

The cycloalkyl ring includes those in which the cycloalkyl described above (e.g., monocyclic, fused, spiro, and bridged cycloalkyl groups) is fused to an aryl, heteroaryl or heterocycloalkyl ring, wherein the ring connected to the parent structure is cycloalkyl. Non-limiting examples include indanyl, tetrahydronaphthyl, benzocycloheptanyl, and the like, preferably indanyl and tetrahydronaphthyl.

The cycloalkyl may be optionally substituted or unsubstituted, and when it is substituted, the substituent is preferably one or more of the following groups; it is substituted with one or more substituents independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "heterocyclyl" refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen, S, S(O) and S(O)$_2$, excluding a cyclic portion of —O—O—, —O—S— or —S—S—, and the remaining ring atoms are carbon atoms. The heterocyclyl preferably contains 3 to 12 (e.g., 3, 4, 5, 6, 7, 8, 9, 10, 11 and 12) ring atoms, of which 1 to 4 (e.g., 1, 2, 3 and 4) are heteroatoms. The heterocyclyl preferably contains 3 to 8 ring atoms, of which 1 to 3 are heteroatoms. The heterocyclyl preferably contains 3 to 6 ring atoms, of which 1 to 3 are heteroatoms. Non-limiting examples of the monocyclic heterocyclyl include azetidinyl, pyrrolidinyl, imidazolidinyl, tetrahydrofuryl, tetrahydropyranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, and the like, preferably tetrahydropyranyl, piperidinyl and pyrrolidinyl. The polycyclic heterocyclyl includes spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more ring atoms are heteroatoms selected from the group consisting of nitrogen, oxygen, S, S(O) and S(O)$_2$, and the remaining ring atoms are carbon atoms. The spiro heterocyclyl may contain one or more double bonds. The spiro heterocyclyl is preferably 6- to 14-membered, more preferably 7- to 10-membered (e.g., 7, 8, 9 and 10-membered). According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 4-membered/4-membered, 4-membered/5-membered, 4-membered/6-membered, 5-membered/5-membered or 5-membered/6-membered monospiro heterocyclyl. Non-limiting examples of the spiro heterocyclyl include:

The term "fused heterocyclyl" refers to a 5- to 20-membered polycyclic heterocyclyl group in which each ring shares a pair of adjacent atoms with the other rings in the system, wherein one or more of the rings may contain one or more double bonds. In the fused heterocyclyl, one or more of the ring atoms are heteroatoms selected from the group consisting of nitrogen, oxygen, S, S(O) and S(O)$_2$, and the remaining ring atoms are carbon atoms. The fused heterocyclyl is preferably 6- to 14-membered, more preferably 7- to 10-membered (e.g., 7, 8, 9 and 10-membered). According to the number of the formed rings, the fused heterocyclyl may be bicyclic, tricyclic, tetracyclic or polycyclic fused heterocyclyl, preferably bicyclic or tricyclic fused heterocyclyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic fused heterocyclyl. Non-limiting examples of fused heterocyclyl include:

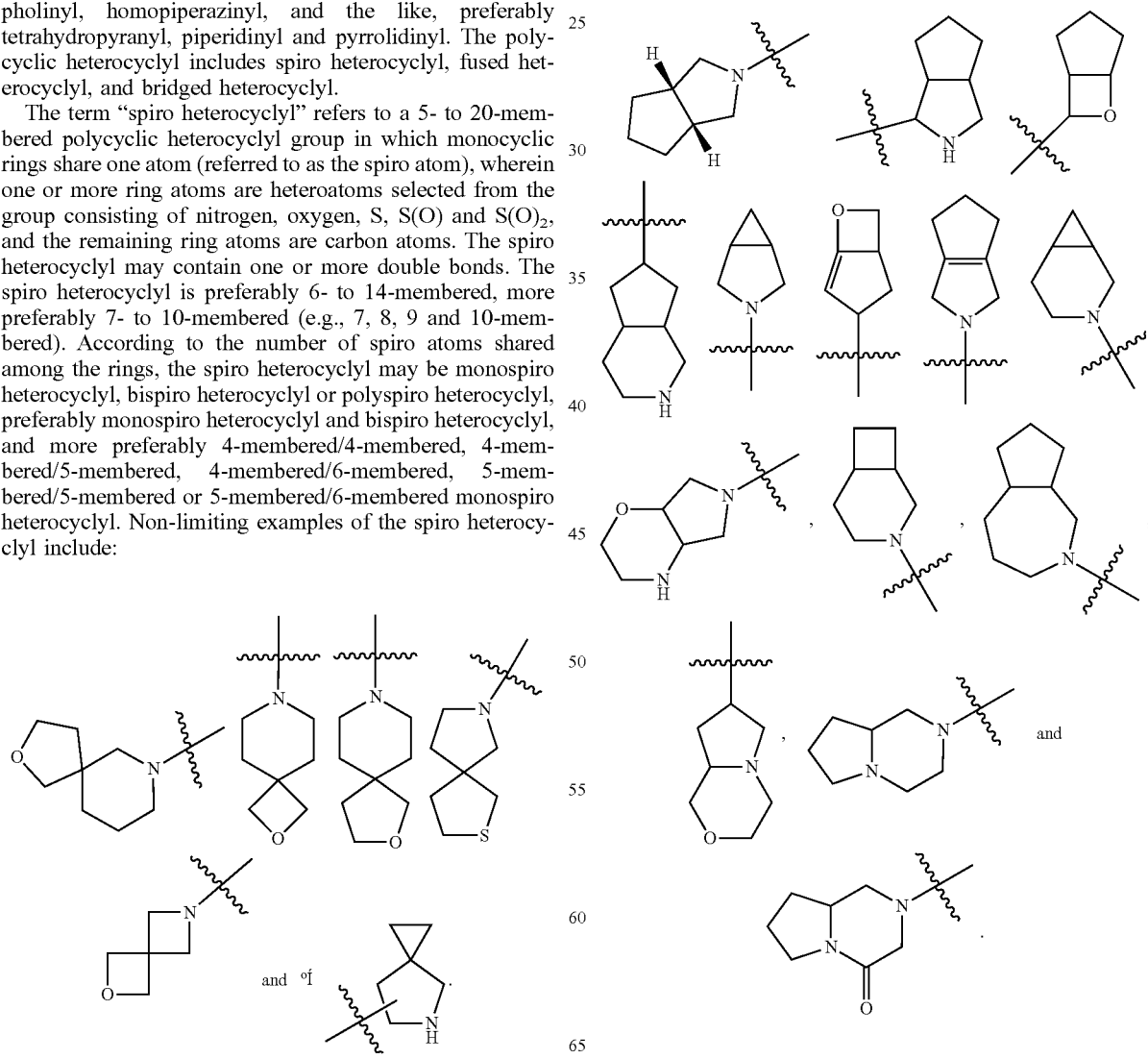

The term "bridged heterocyclyl" refers to a 5- to 14-membered polycyclic heterocyclyl group in which any two rings share two atoms that are not directly connected to each other, wherein the bridged heterocyclyl may contain one or more double bonds. In the bridged heterocyclyl, one or more of the ring atoms are heteroatoms selected from the group consisting of nitrogen, oxygen, S, S(O) and S(O)$_2$, and the remaining ring atoms are carbon atoms. The bridged heterocyclyl is preferably 6- to 14-membered, more preferably 7- to 10-membered (e.g., 7, 8, 9 and 10-membered). According to the number of the formed rings, the bridged heterocyclyl may be bicyclic, tricyclic, tetracyclic or polycyclic, preferably bicyclic, tricyclic or tetracyclic, and more preferably bicyclic or tricyclic. Non-limiting examples of the bridged heterocyclyl include:

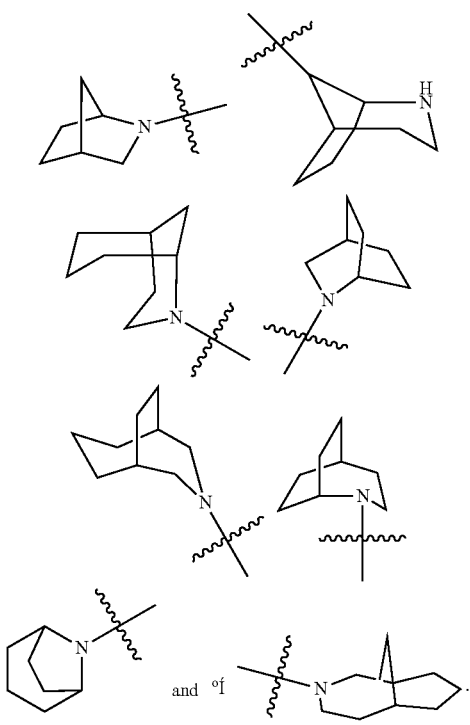

The heterocyclyl ring includes those in which the heterocyclyl described above (e.g., monocyclic, fused, spiro and bridged heterocyclyl groups) is fused to an aryl, heteroaryl or cycloalkyl ring, wherein the ring connected to the parent structure is heterocyclyl. Non-limiting examples include:

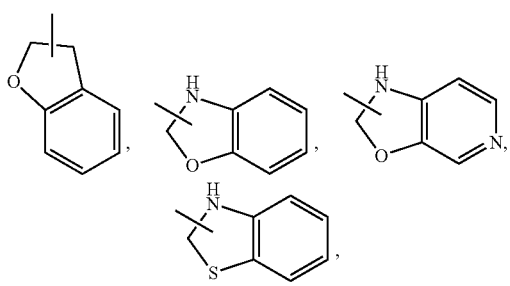

and the like.

The heterocyclyl may be optionally substituted or unsubstituted, and when it is substituted, the substituent is preferably one or more of the following groups; it is substituted with one or more substituents independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "aryl" refers to a 6- to 20-membered, preferably 6- to 10-membered, and more preferably 6-membered carbon monocyclic or fused polycyclic (i.e., rings that share a pair of adjacent carbon atoms) group having a conjugated n-electron system such as phenyl and naphthyl. The aryl ring includes those in which the aryl described above is fused to a heteroaryl, heterocyclyl or cycloalkyl ring, wherein the ring connected to the parent structure is an aryl ring. Non-limiting examples include:

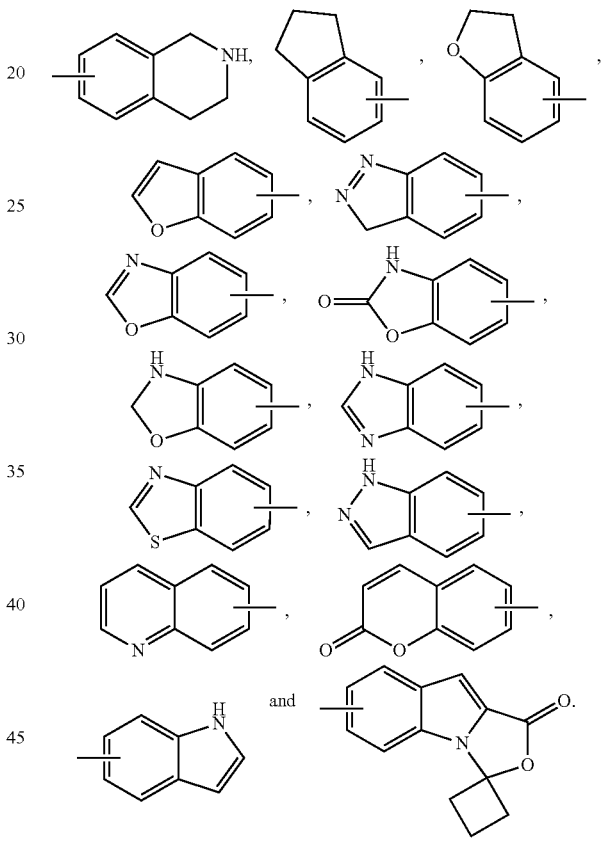

The aryl may be substituted or unsubstituted, and when it is substituted, the substituent is preferably one or more of the following groups; it is substituted with one or more substituents independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "heteroaryl" refers to a heteroaromatic system containing 1 to 4 (e.g., 1, 2, 3 and 4) heteroatoms and 5 to 20 ring atoms, wherein the heteroatoms are selected from the group consisting of oxygen, sulfur and nitrogen. The heteroaryl is preferably 5- to 10-membered (e.g. 5-, 6-, 7-, 8-, 9- and 10-membered) and contains 1 to 3 heteroatoms. The heteroaryl is more preferably 5- or 6-membered and contains 1 to 3 heteroatoms. Non-limiting examples are pyrazolyl, imidazolyl, furyl, thienyl, thiazolyl, oxazolyl, pyrrolyl, triazolyl, tetrazolyl, pyridyl, pyrimidinyl, thiadiazole, pyrazinyl, and the like. The heteroaryl ring may be fused to an aryl, heterocyclyl or cycloalkyl ring, wherein the ring connected to the parent structure is heteroaryl. Non-limiting examples include:

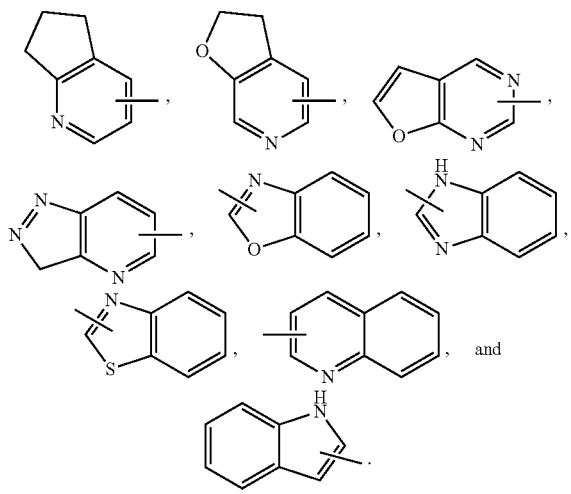

The heteroaryl may be optionally substituted or unsubstituted, and when it is substituted, the substituent is preferably one or more of the following groups; it is substituted with one or more substituents preferably independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The cycloalkyl, heterocyclyl, aryl and heteroaryl described above have 1 residue derived from the parent ring by removal of one hydrogen atom from a ring atom, or 2 residues derived from the parent ring by removal of two hydrogen atoms from the same ring atom or two different ring atoms.

The term "alkylthio" refers to —S-(alkyl) and —S-(unsubstituted cycloalkyl), wherein the alkyl is as defined above. Non-limiting examples of the alkylthio include: methylthio, ethylthio, propylthio, butylthio, cyclopropylthio, cyclobutylthio, cyclopentylthio and cyclohexylthio. The alkylthio may be optionally substituted or unsubstituted, and when it is substituted, the substituent is preferably one or more of the following groups; it is substituted with one or more substituents independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "cycloalkyloxy" refers to —O-cycloalkyl, wherein the cycloalkyl is as defined above.

The term "haloalkyl" refers to an alkyl group substituted with one or more halogens, wherein the alkyl group is as defined above.

The term "deuterated alkyl" refers to an alkyl group substituted with one or more deuterium atoms, wherein the alkyl group is as defined above. The term "haloalkoxy" refers to an alkoxy group substituted with a halogen, wherein the alkoxy group is as defined above.

The term "hydroxyalkyl" refers to an alkyl group substituted with one or more hydroxy groups, wherein the alkyl group is as defined above.

The term "halohydroxyalkyl" refers to a hydroxyalkyl group substituted with one or more halogens, wherein the hydroxyalkyl group is as defined above. The term "hydroxy" refers to —OH group.

The term "halogen" refers to fluorine, chlorine, bromine or iodine.

The term "amino" refers to —NH$_2$.
The term "cyano" refers to —CN.
The term "nitro" refers to —NO$_2$.
The term "aldehyde" refers to —C(O)H.
The term "carboxyl" refers to —C(O)OH.
The term "aldehyde" refers to —C(O)H.
The term "carboxylate" refers to —C(O)O(alkyl) or —C(O)O(cycloalkyl), wherein the alkyl and cycloalkyl are as defined above.

The term "hydroxy protective group" is a suitable group known in the art for protecting hydroxy. See the hydroxy protective groups in the literature ("*Protective Groups in Organic Synthesis*", 5$^{th}$ Ed. T. W. Greene & P. G. M. Wuts). As an example, preferably, the hydroxy protective group may be (C$_{1-10}$alkyl or aryl)$_3$silyl such as triethylsilyl, triisopropylsilyl, tert-butyldimethylsilyl, tert-butyldiphenylsilyl, and the like; or may be C$_{1-10}$ alkyl or substituted alkyl, preferably alkoxy or aryl-substituted alkyl, more preferably C$_{1-6}$ alkoxy-substituted C$_{1-6}$ alkyl or phenyl-substituted C$_{1-6}$ alkyl, and most preferably C$_{1-4}$ alkoxy-substituted C$_{1-4}$ alkyl such as methyl, tert-butyl, allyl, benzyl, methoxymethyl (MOM), ethoxyethyl, 2-tetrahydropyranyl (THP), and the like; or may be (C$_{1-10}$ alkyl or aryl)acyl such as formyl, acetyl, benzoyl, and the like; or may be (C$_{1-6}$ alkyl or C$_{6-10}$ aryl)sulfonyl; or may also be (C$_{1-6}$ alkoxy or C$_{6-10}$ aryloxy) carbonyl. The term "optional" or "optionally" means that the event or circumstance subsequently described may, but not necessarily, occur, and that the description includes instances where the event or circumstance occurs or does not occur. For example, "a heterocyclyl group optionally substituted with alkyl" means that alkyl may be, but not necessarily, present, and that the description includes instances where the heterocyclyl group is or is not substituted with alkyl.

"Substituted" means that one or more, preferably up to 5, more preferably 1-3 hydrogen atoms in the group are independently substituted with a corresponding number of substituents, wherein each of the substituents has an independent option (i.e., the substituents may be identical or different). It goes without saying that a substituent is only in its possible chemical position, and those skilled in the art will be able to determine (experimentally or theoretically) possible or impossible substitution without undue efforts. For example, it may be unstable when an amino or hydroxy group having a free hydrogen is bound to a carbon atom having an unsaturated (e.g., olefinic) bond.

The term "pharmaceutical composition" refers to a mixture containing one or more of the compounds described herein or a physiologically/pharmaceutically acceptable salt or pro-drug thereof, and other chemical components, and other components, for example physiologically/pharmaceutically acceptable carriers and excipients. The purpose of the pharmaceutical composition is to promote the administration to an organism, which facilitates the absorption of the active ingredient, thereby exerting biological activities.

The term "pharmaceutically acceptable salt" refers to salts of the disclosed compounds which are safe and effective for use in the body of a mammal and possess the requisite biological activities.

The compounds disclosed herein include isotopic derivatives thereof. The term "isotopic derivative" refers to compounds that differ in structure only by having one or more enriched isotopic atoms. For example, compounds having the structure disclosed herein having "deuterium" or "tritium" in place of hydrogen, or $^{18}F$-fluorine labeling ($^{18}F$ isotope) in place of fluorine, or $^{11}C$-, $^{13}C$- or $^{14}C$-enriched carbon ($^{11}C$-, $^{13}C$- or $^{14}C$-carbon labeling; $^{13}C$- or $^{14}C$-isotope) in place of a carbon atom are within the scope of the present disclosure. Such a compound can be used as an analytical tool or a probe in, for example, a biological assay, or may be used as a tracer for in vivo diagnostic imaging of disease, or as a tracer in a pharmacodynamic, pharmacokinetic or receptor study.

Various deuterated forms of the compound of general formula (I) of the present disclosure are those in which each of the available hydrogen atoms connected to the carbon atoms can be independently replaced by a deuterium atom. Unless otherwise stated, when a position is specifically designated to D or deuterium, that position is construed as deuterium having an abundance that is at least 3000 times greater than the natural abundance of deuterium (which is 0.015%) (i.e., at least 45% incorporation of deuterium). Those skilled in the art are able to synthesize the deuterated forms of the compound of general formula (I) with reference to the relevant literature. Commercially available deuterated starting materials can be used in preparing the deuterated forms of the compound of general formula (I), or they can be synthesized by using conventional techniques with deuterated reagents including, but not limited to, deuterated borane, tri-deuterated borane in tetrahydrofuran, deuterated lithium aluminum hydride, deuterated iodoethane, deuterated iodomethane, and the like.

For drugs and pharmacological active agents, the term "therapeutically effective amount" refers to an amount of a medicament or an agent that is sufficient to provide the desired effect but is non-toxic. The determination of the effective amount varies from person to person. It depends on the age and general condition of a subject, as well as the particular active substance used. The appropriate effective amount in a case may be determined by those skilled in the art in light of routine tests.

Synthesis of the Compounds of the Present Disclosure

In order to achieve the purpose of the present disclosure, the following technical schemes are adopted in the present disclosure:

Scheme 1

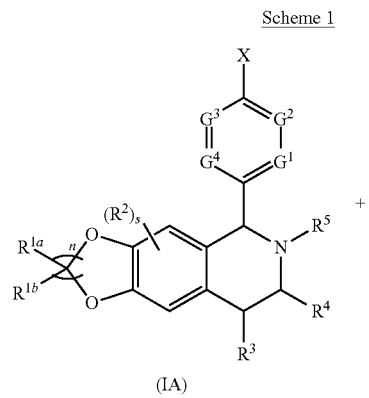

(IA)

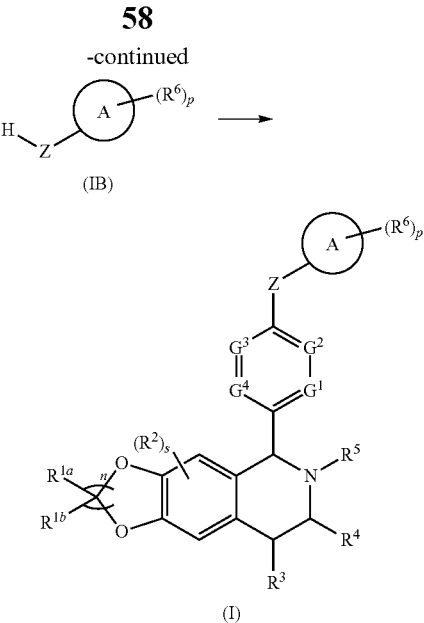

Provided is a method for preparing the compound of general formula (I) or the tautomer, mesomer, racemate, enantiomer or diastereomer thereof or the mixture thereof, or the pharmaceutically acceptable salt thereof of the present disclosure, which comprises the following step:

subjecting a compound of general formula (IA) and a compound of general formula (IB) to a coupling reaction under alkaline conditions in the presence of a catalyst to give the compound of general formula (I), wherein:

X is Br;

ring A, Z, $G^1$, $G^2$, $G^3$, $G^4$, $R^{1a}$, $R^{1b}$, $R^2$-$R^6$, p, n and s are as defined in general formula (I).

Provided is a method for preparing the compound of general formula (II) or the tautomer, mesomer, racemate, enantiomer or diastereomer thereof or the mixture thereof, or the pharmaceutically acceptable salt thereof of the present disclosure, which comprises the following step:

Scheme 2

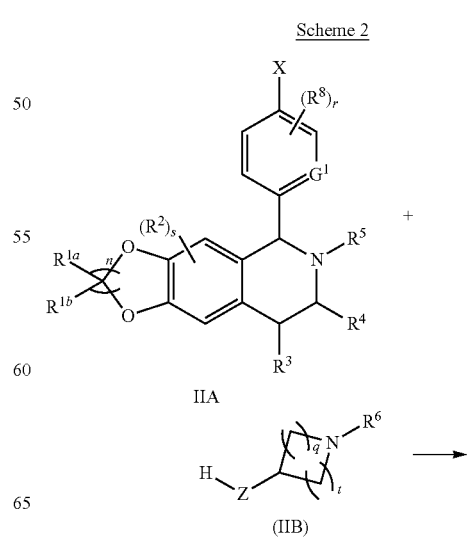

-continued

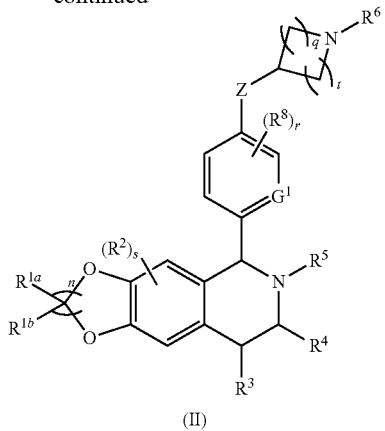

(II)

subjecting a compound of general formula (IIA) and a compound of general formula (IIB) to a coupling reaction under alkaline conditions in the presence of a catalyst to give the compound of general formula (II),
wherein:
X is Br;
$G^1$, Z, $R^{1a}$, $R^{1b}$, $R^2$-$R^6$, $R^8$ r, q, t, n and s are as defined in general formula (II).

Scheme 3

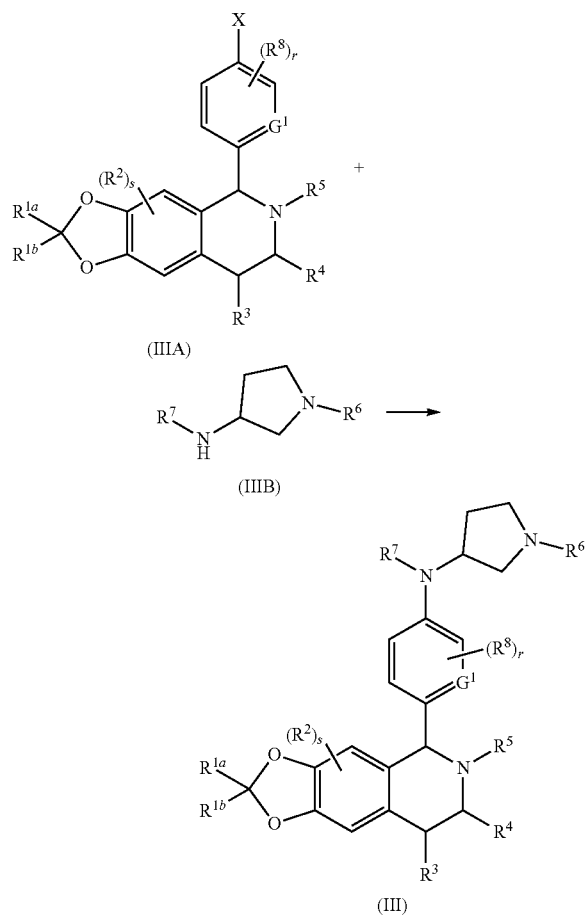

Provided is a method for preparing the compound of general formula (III) or the tautomer, mesomer, racemate, enantiomer or diastereomer thereof or the mixture thereof, or the pharmaceutically acceptable salt thereof of the present disclosure, which comprises the following step:
  subjecting a compound of general formula (IIIA) and a compound of general formula (IIIB) to a coupling reaction under alkaline conditions in the presence of a catalyst to give the compound of general formula (III),
wherein:
X is Br;
$G^1$, $R^{1a}$, $R^{1b}$, $R^2$-$R^8$, r and s are as defined in general formula (III).

Scheme 4

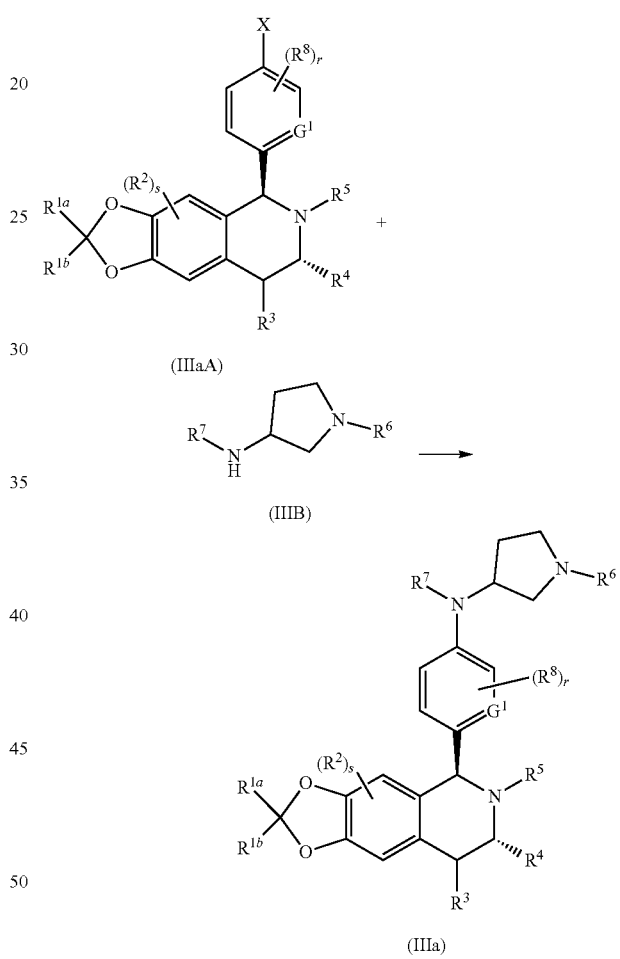

Provided is a method for preparing the compound of general formula (IIIa) or the tautomer, mesomer, racemate, enantiomer or diastereomer thereof or the mixture thereof, or the pharmaceutically acceptable salt thereof of the present disclosure, which comprises the following step:
  subjecting a compound of general formula (IIIaA) and a compound of general formula (IIIB) to a coupling reaction under alkaline conditions in the presence of a catalyst to give the compound of general formula (IIIa),
wherein:
X is Br;
$G^1$, $R^{1a}$, $R^{1b}$, $R^2$-$R^8$, r and s are as defined in general formula (IIIa).

Scheme 5

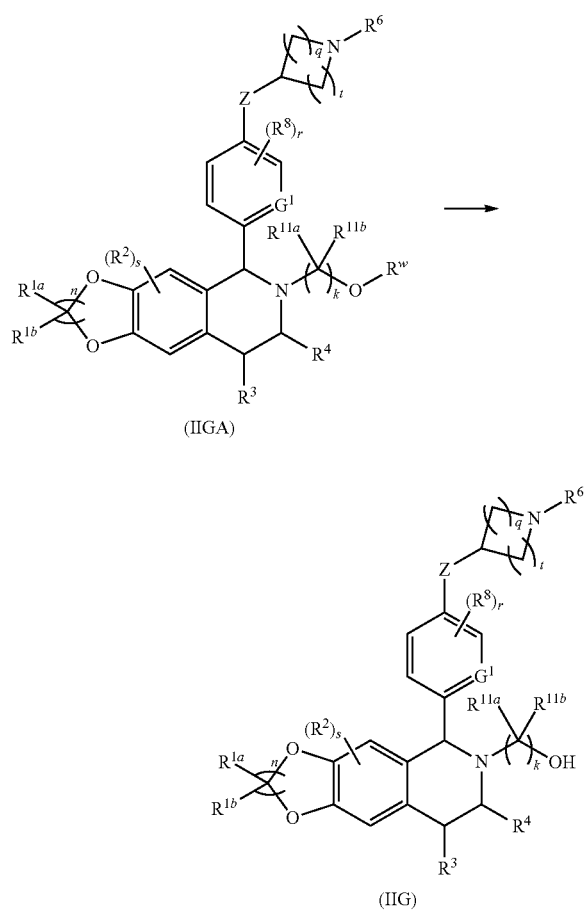

(IIGA)

↓

(IIG)

Provided is a method for preparing the compound of general formula (IIG) or the tautomer, mesomer, racemate, enantiomer or diastereomer thereof or the mixture thereof, or the pharmaceutically acceptable salt thereof of the present disclosure, which comprises the following step:

removing a hydroxy protective group from a compound of general formula (IIGA) in the presence of a phase transfer catalyst (preferably n-tetrabutylammonium fluoride) to give the compound of general formula (IIG), wherein:

$R^w$ is a hydroxy protective group, and is preferably

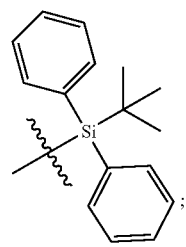

Z, $G^1$, $R^{1a}$, $R^{1b}$, $R^2$-$R^4$, $R^6$, $R^8$, $R^{11a}$, $R^{11b}$, q, t, k, r, n and s are as defined in general formula (IIG).

Scheme 6

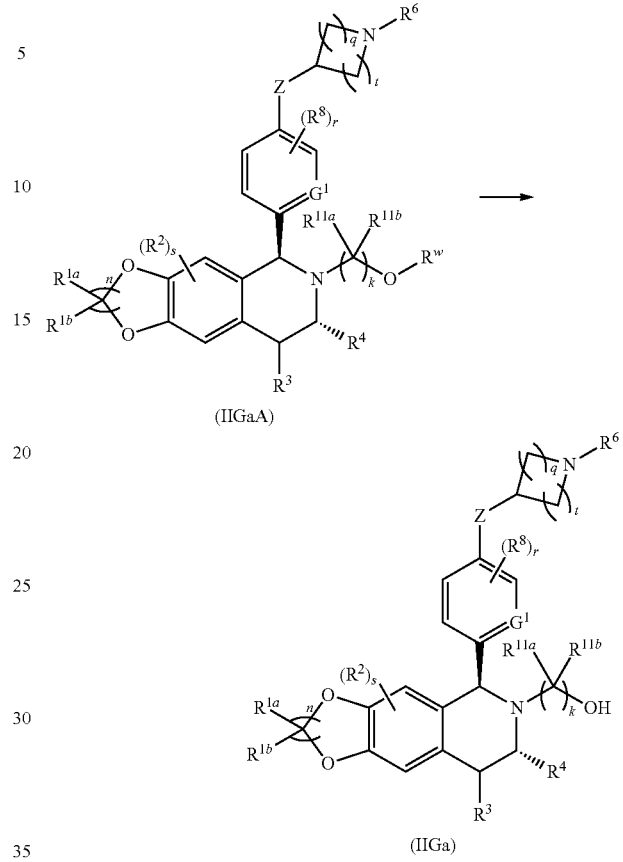

(IIGaA)

↓

(IIGa)

Provided is a method for preparing the compound of general formula (IIGa) or the tautomer, mesomer, racemate, enantiomer or diastereomer thereof or the mixture thereof, or the pharmaceutically acceptable salt thereof of the present disclosure, which comprises the following step:

removing a hydroxy protective group from a compound of general formula (IIGaA) in the presence of a phase transfer reagent (preferably n-tetrabutylammonium fluoride) to give the compound of general formula (IIGa), wherein:

$R^w$ is a hydroxy protective group, and is preferably

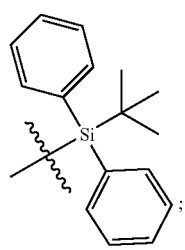 [SMILES: *[Si](c1ccccc1)(c1ccccc1)C(C)(C)C]

Z, $G^1$, $R^{1a}$, $R^{1b}$, $R^2$-$R^4$, $R^6$, $R^8$, $R^{11a}$, $R^{11b}$, q, t, k, r, n and s are as defined in general formula (IIGa).

The reagents that provide alkaline conditions in the above synthesis schemes 1-4 described above include organic bases including, but not limited to, triethylamine, N,N-diisopropylethylamine, n-butyllithium, lithium diisopropylamide, sodium acetate, potassium acetate, sodium tert-butoxide and potassium tert-butoxide; and inorganic bases including, but not limited to, sodium hydride, potassium phosphate, sodium carbonate, potassium carbonate or cesium carbonate, sodium hydroxide, lithium hydroxide and potassium hydroxide; and are preferably sodium tert-butoxide.

The catalysts in the above synthesis schemes 1-4 described above include, but are not limited to tetrakis(triphenylphosphine)palladium(0), palladium dichloride, palladium acetate, bis(dibenzylideneacetone)palladium, chlorine(2-dicyclohexylphosphino-2',4',6'-triisopropyl-1,1'-biphenyl) [2-(2'-amino-1,1'-biphenyl)] palladium, [1,1'-bis(diphenylphosphino)ferrocene] palladium(II) dichloride, [1,1'-bis(dibenzylphosphino)ferrocene]palladium dichloride or tris(dibenzylideneacetone)dipalladium(0);

The phase transfer reagents in the synthesis schemes 5 and 6 described above include, but are not limited to, benzyltriethylammonium chloride (TEBA), tetrabutylammonium bromide, tetrabutylammonium chloride, n-tetrabutylammonium fluoride, tetrabutylammonium hydrogen sulfate (TBAB), trioctylmethylammonium chloride, dodecyltrimethylammonium chloride and tetradecyltrimethylammonium chloride, and are preferably n-tetrabutylammonium fluoride;

The above reactions are preferably conducted in solvents including, but not limited to acetic acid, methanol, ethanol, n-butanol, toluene, acetonitrile, tetrahydrofuran, dichloromethane, petroleum ether, ethyl acetate, n-hexane, dimethyl sulfoxide, 1,4-dioxane, ethylene glycol dimethyl ether, water or N,N-dimethylformamide, and mixtures thereof.

DETAILED DESCRIPTION

The following examples further illustrate the present disclosure, but the present disclosure is not limited thereto.

EXAMPLES

The structure of the compound was determined by nuclear magnetic resonance (NMR) spectroscopy and/or mass spectrometry (MS). NMR shifts (δ) are given in units of $10^{-6}$ (ppm). NMR spectra were measured using a Bruker AVANCE-400 nuclear magnetic resonance instrument, with deuterated dimethyl sulfoxide (DMSO-$d_6$), deuterated chloroform (CDCl$_3$) and deuterated methanol (CD$_3$OD) as determination solvents, with tetramethylsilane (TMS) as internal standard.

Mass spectra were measured using Agilent 1200/1290 DAD-6110/6120 Quadrupole MS liquid chromatography-mass spectrometry system (manufacturer: Agilent; MS model: 6110/6120 Quadrupole MS), waters ACQuity UPLC-QD/SQD (manufacturer: waters; MS model:

waters ACQuity Qda Detector/waters SQ Detector) and

THERMO Ultimate 3000-Q Exactive (manufacturer: THERMO; MS model: THERMO Q Exactive).

High performance liquid chromatography (HPLC) was performed using Agilent HPLC 1200DAD, Agilent HPLC 1200VWD and Waters HPLC e2695-2489 high pressure liquid chromatography.

Chiral HPLC was performed on Agilent 1260 DAD HPLC.

HPLC preparation was performed using Waters 2545-2767, Waters 2767-SQ Detecor2, Shimadzu LC-20AP and Gilson GX-281 preparative chromatographs.

Chiral preparation was performed on a Shimadzu LC-20AP preparative chromatograph.

A CombiFlash Rf200 (TELEDYNE ISCO) system was used for rapid preparation.

Huanghai HSGF254 or Qingdao GF254 silica gel plates of specifications 0.15 mm to 0.2 mm were adopted for thin layer chromatography (TLC) analysis and 0.4 mm to 0.5 mm for TLC separation and purification.

The silica gel column chromatography generally used 200 to 300-mesh silica gel (Huanghai, Yantai) as the carrier.

The mean kinase inhibition rates and IC50 values were measured using a NovoStar microplate reader (BMG, Germany).

Known starting materials described herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions can be performed in an argon atmosphere or a nitrogen atmosphere unless otherwise specified.

The argon atmosphere or nitrogen atmosphere means that the reaction flask is connected to a balloon containing about 1 L of argon or nitrogen.

A hydrogen atmosphere means that the reaction flask is connected to a balloon containing about 1 L of hydrogen.

Parr 3916EKX hydrogenator, Qinglan QL-500 hydrogenator or HC2-SS hydrogenator was used in the pressurized hydrogenation reactions.

The hydrogenation reactions usually involve 3 cycles of vacuumization and hydrogen purge.

A CEM Discover-S 908860 microwave reactor was used in the microwave reactions.

In the examples, a solution refers to an aqueous solution unless otherwise specified.

In the examples, the reaction temperature was room temperature, i.e., 20° C. to 30° C., unless otherwise specified.

The monitoring of the reaction progress in the examples was conducted by thin layer chromatography (TLC). The developing solvent for reactions, the eluent system for column chromatography purification and the developing solvent system for thin layer chromatography included: A: dichloromethane/methanol system, B: n-hexane/ethyl acetate system, and C: petroleum ether/ethyl acetate system. The volume ratio of the solvents was adjusted according to the polarity of the compound, or by adding a small amount of basic or acidic reagents such as triethylamine and acetic acid.

Example 1

(S)-1-(3-fluoropropyl)-N-(4-((5R,7R)-7-methyl-6-(2,2,2-trifluoroethyl)-5,6,7,8-tetrahydro-[1,3]dioxolo[4,5-g]isoquinolin-5-yl)phenyl)pyrrolidin-3-amine 1

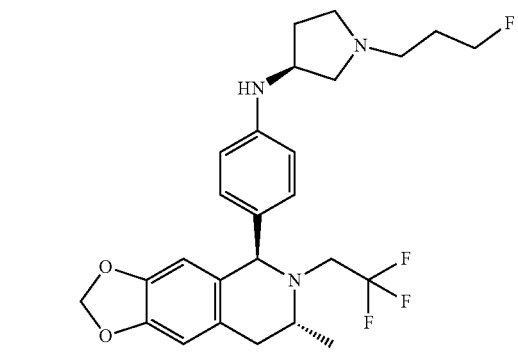

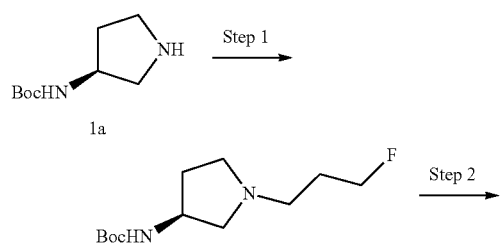

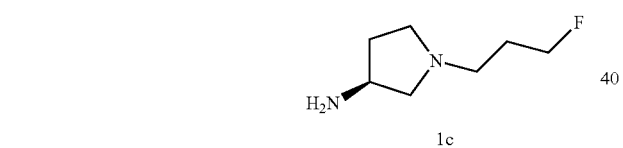

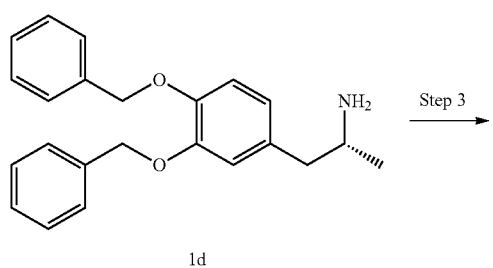

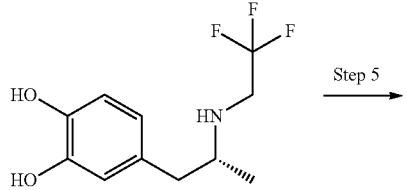

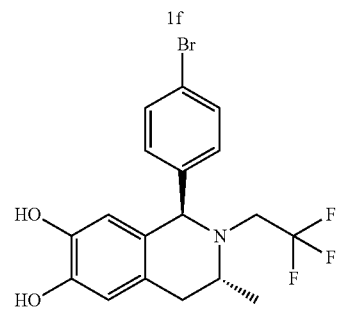

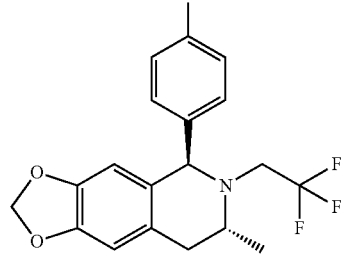

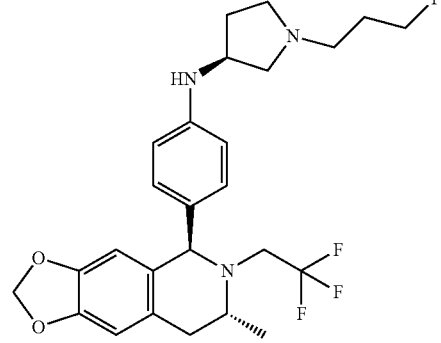

Step 1 tert-Butyl (S)-(1-(3-fluoropropyl)pyrrolidin-3-yl)carbamate 1b tert-Butyl (S)-pyrrolidin-3-ylcarbamate 1a (1.86 g, 10 mmol, Accela) was dissolved in N,N-dimethylformamide (20 mL), and diisopropylethylamine (1.55 g, 12 mmol) was added, followed by the dropwise addition of 1-fluoro-3-iodopropane (207 mg, 11 mmol). The reaction mixture was stirred for 12 h. Water (50 mL) was added, followed by the extraction with ethyl acetate (50 mL×3) and washing with water (50 mL×2) and saturated sodium chloride solution (50 mL). The organic phases were combined, dried over anhydrous sodium sulfate, and filtered. The filtrate was concentrated under reduced pressure, and the resulting residue was purified by column chromatography with developing solvent system B to give the title compound 1b (1.92 g, 78% yield).

Step 2

(S)-1-(3-fluoropropyl)pyrrolidin-3-amine 1c

Compound 1b (1.23 g, 5 mmol) was dissolved in dichloromethane (10 mL), and a 5 M solution of hydrogen chloride in 1,4-dioxane (2 mL) was added dropwise in an ice bath. After addition, the reaction mixture was stirred at room temperature for 1.5 h and concentrated under reduced pressure. Saturated sodium bicarbonate solution (25 mL) was added, followed by the extraction with ethyl acetate (15 mL×3). The organic phases were combined, washed with saturated sodium chloride solution (15 mL), dried over anhydrous sodium sulfate, and filtered. The filtrate was concentrated under reduced pressure to give the title compound 1c (702 mg, 96% yield).

Step 3

(R)-1-(3,4-bis(benzyloxy)phenyl)-N-(2,2,2-trifluoroethyl)propan-2-amine 1e (R)-1-(3,4-bis(benzyloxy)phenyl)propan-2-amine 1d (7.0 g, 20.1 mmol, prepared by using the well-known method in "*European Journal of Medicinal Chemistry,* 2014, 67(23), 35-36") was dissolved in dioxane (100 mL), and diisopropylethylamine (7.8 g, 60.4 mmol), 2,2,2-trifluoroethyl trifluoromethanesulfonate (9.4 g, 40.3 mmol, prepared as disclosed in "Example 59 on page 69 of the specification of Patent Application US20140249162") was added. The reaction mixture was stirred in an oil bath at 80° C. in an argon atmosphere for 20 h. The reaction mixture was cooled and concentrated under reduced pressure. Saturated sodium bicarbonate solution (50 mL) was added, followed by the extraction with ethyl acetate (100 mL×2). The organic phases were combined, dried over anhydrous sodium sulfate, and filtered. The filtrate was concentrated under reduced pressure, and the resulting residue was purified by column chromatography with developing solvent system B to give the title compound 1e (7.6 g, 88% yield).

MS m/z (ESI): 430.3 [M+1].

Step 4

(R)-4-(2-((2,2,2-trifluoroethyl)amino)propyl)-1,2-benzenediol 1f

Compound 1e (3.3 g, 7.7 mmol) was dissolved in methanol (10 mL), and palladium hydroxide on carbon (0.5 g, 3.8 mmol) was added in an argon atmosphere. The reaction mixture was stirred under hydrogen balloon for 3 h, and filtered. The filtrate was concentrated under reduced pressure to give the title compound 1f (1.8 g, 96% yield).

Step 5

(1R,3R)-1-(4-bromophenyl)-3-methyl-2-(2,2,2-threefluoroethyl)-1,2,3,4-tetrahydroisoquinoline-6,7-diol 1g Compound 1f (3.0 g, 12.0 mmol) was dissolved in toluene (100 mL), and acetic acid (1.4 g, 23.3 mmol) and 4-bromobenzaldehyde (4.4 g, 23.8 mmol) were added. The reaction mixture was stirred in an oil bath at 80° C. for 16 h, and the reaction was terminated. The reaction mixture was cooled and concentrated under reduced pressure. Water (100 mL) was added, and the aqueous phase was adjusted to about pH 8 by adding saturated sodium bicarbonate solution (200 mL) and extracted with ethyl acetate (100 mL×2). The organic phases were combined, dried over anhydrous sodium sulfate, and filtered. The filtrate was concentrated under reduced pressure, and the resulting residue was purified by column chromatography with developing solvent system B to give the title compound 1g (3.5 g, 70% yield).

MS m/z (ESI): 416.0 [M+1].

Step 6

(5R,7R)-5-(4-bromophenyl)-7-methyl-6-(2,2,2-trifluoroethyl)-5,6,7,8-tetrahydro-[1,3]dioxolo[4,5-g]isoquinoline 1h Compound 1g (3.5 g, 8.4 mmol) was dissolved in N,N-dimethylformamide (100 mL), and dibromomethane (1.9 g, 10.9 mmol) and cesium carbonate (3.6 g, 11.0 mmol) were added. The reaction mixture was stirred in an oil bath at 70° C. for 16 h, and the reaction was terminated. The reaction mixture was cooled and concentrated under reduced pressure. Water (100 mL) was added, followed by the extraction with ethyl acetate (100 mL×2). The organic phases were combined, dried over anhydrous sodium sulfate, and filtered. The filtrate was concentrated under reduced pressure, and the resulting residue was purified by column chromatography with developing solvent system B to give the title compound 1h (2.4 g, 67% yield).

Step 7

(S)-1-(3-fluoropropyl)-N-(4-((5R,7R)-7-methyl-6-(2,2,2-trifluoroethyl)-5,6,7,8-tetrahydro-[1,3]dioxolo[4,5-g]isoquinolin-5-yl)phenyl)pyrrolidin-3-amine 1

Compound 1h (600 mg, 1.4 mmol) was dissolved in dioxane (10 mL), and compound 1c (225 mg, 1.5 mmol), 2-dicyclohexylphosphine-2',6'-bis(N,N-dimethylamino)-1,1'-biphenyl (3 mg, 0.007 mmol), tris(dibenzylideneacetone)dipalladium(0) (20 mg, 0.02 mmol) and sodium tert-butoxide (471 mg, 4.9 mmol) were added. The reaction mixture was stirred in an oil bath at 105° C. in an argon atmosphere for 16 h, and the reaction was terminated. The reaction mixture was cooled and concentrated. Saturated sodium bicarbonate solution (20 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 1 (449 mg, 65% yield).

MS m/z (ESI): 494.2 [M+1].

1H NMR (400 MHz, CD$_3$OD) 6.84 (d, 2H), 6.49 (s, 1H), 6.43 (d, 2H), 6.20 (s, 1H), 5.75 (d, 2H), 4.64 (s, 1H), 4.45-4.42 (m, 1H), 4.33-4.30 (m, 1H), 3.91-3.87 (m, 1H), 3.18-3.15 (m, 2H), 2.83-2.80 (m, 2H), 2.66-2.40 (m, 8H), 1.85-1.60 (m, 3H), 0.92 (d, 3H).

Example 2

(S)—N-(3,5-difluoro-4-((5S,7R)-7-methyl-6-(2,2,2-trifluoroethyl)-5,6,7,8-tetrahydro-[1,3]dioxolo[4,5-g]isoquinolin-5-yl)phenyl)-1-(3-fluoropropyl)pyrrolidin-3-amine 2

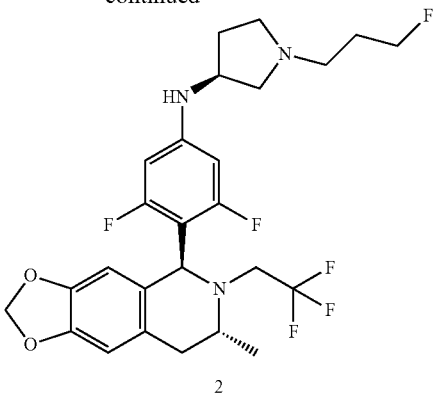

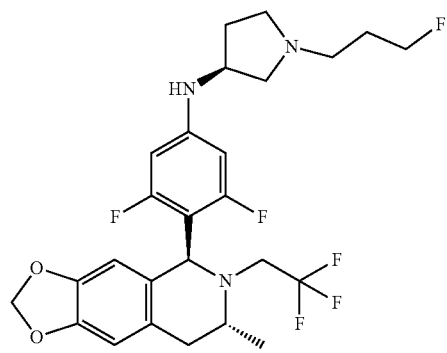

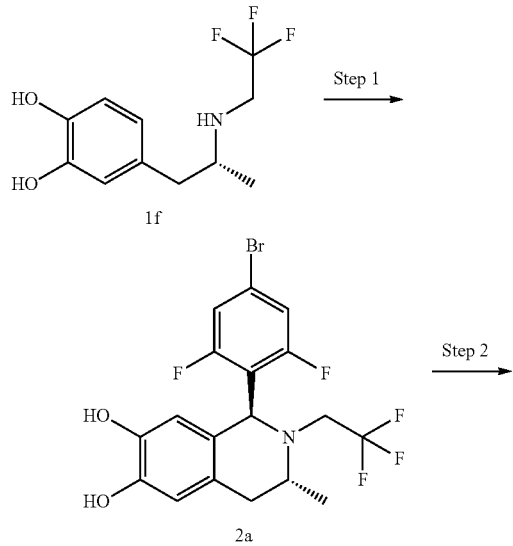

Step 1

(1S,3R)-1-(4-bromo-2,6-difluorophenyl)-3-methyl-2-(2,2,2-threefluoroethyl)-1,2,3,4-tetrahydroisoquinoline-6,7-diol 2a Compound 1f (310 mg, 1.2 mmol) was dissolved in toluene (5 mL), and acetic acid (598 mg, 10.0 mmol) and 4-bromo-2,6-difluorobenzaldehyde (384 mg, 1.7 mmol) were added. The reaction mixture was stirred in an oil bath at 80° C. for 16 h, and the reaction was terminated. The reaction mixture was cooled and concentrated under reduced pressure. Water (10 mL) was added, and the aqueous phase was adjusted to about pH 8 by adding saturated sodium bicarbonate solution (20 mL) and extracted with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 2a (390 mg, 72% yield).

MS m/z (ESI): 451.9 [M+1].

Step 2

(5S,7R)-5-(4-bromo-2,6-difluorophenyl)-7-methyl-6-(2,2,2-trifluoroethyl)-5,6,7,8-tetrahydro-[1,3]dioxolo[4,5-g]isoquinoline 2b Compound 2a (130 mg, 0.3 mmol) was dissolved in N,N-dimethylformamide (10 mL), and dibromomethane (60 mg, 0.3 mmol) and cesium carbonate (121 mg, 0.4 mmol) were added. The reaction mixture was stirred in an oil bath at 70° C. for 16 h, and the reaction was terminated. The reaction mixture was cooled and concentrated. Water (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 2b (85 mg, 61% yield).

MS m/z (ESI): 464.0 [M+1].

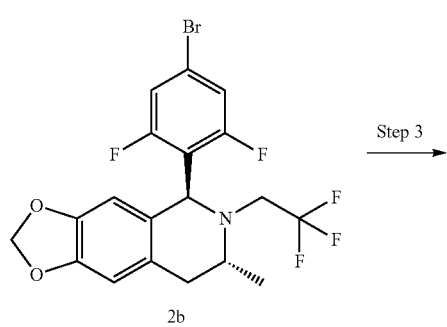

Step 3

(S)—N-(3,5-difluoro-4-((5S,7R)-7-methyl-6-(2,2,2-trifluoroethyl)-5,6,7,8-tetrahydro-[1,3]dioxolo[4,5-g]isoquinolin-5-yl)phenyl)-1-(3-fluoropropyl)pyrrolidin-3-amine 2

Compound 2b (70 mg, 0.2 mmol) was dissolved in dioxane (10 mL), and compound 1c (29 mg, 0.2 mmol), 2-dicyclohexylphosphine-2',6'-bis(N,N-dimethylamino)-1,1'-biphenyl (2 mg, 0.005 mmol), tris(dibenzylideneacetone)dipalladium(0) (2 mg, 0.002 mmol) and sodium tert-butoxide (43 mg, 0.5 mmol) were added. The reaction mixture was stirred in an oil bath at 105° C. in an argon atmosphere for 16 h, and the reaction was terminated. The reaction mixture was cooled and concentrated under reduced pressure. Saturated sodium bicarbonate solution (20 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 2 (449 mg, 58% yield).

MS m/z (ESI): 530.1 [M+1].

1H NMR (400 MHz, CD$_3$OD) 6.45 (s, 1H), 6.07 (s, 1H), 6.03-6.00 (m, 2H), 5.73 (d, 2H), 4.94 (s, 1H), 4.46-4.43 (m, 1H), 4.34-4.31 (m, 1H), 3.87-3.83 (m, 1H), 3.38-3.35 (m, 1H), 3.13-3.02 (m, 2H), 2.86-2.42 (m, 9H), 1.87-1.63 (m, 3H), 0.92 (d, 3H).

Example 3

2,2-Difluoro-3-((5R,7R)-5-(4-(((S)-1-(3-fluoropropyl)pyrrolidin-3-yl)amino)phenyl)-7-methyl-7,8-dihydro-[1,3]dioxolo[4,5-g]isoquinolin-6(5H)-yl)propan-1-ol 3

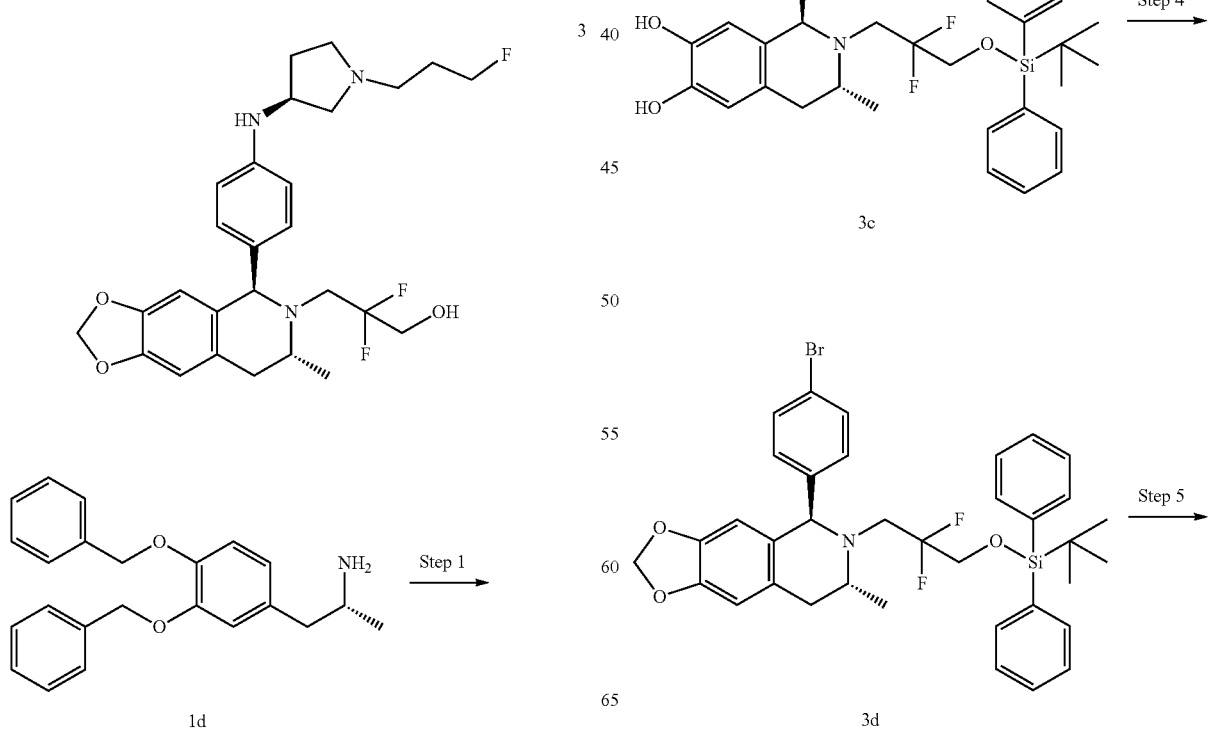

-continued

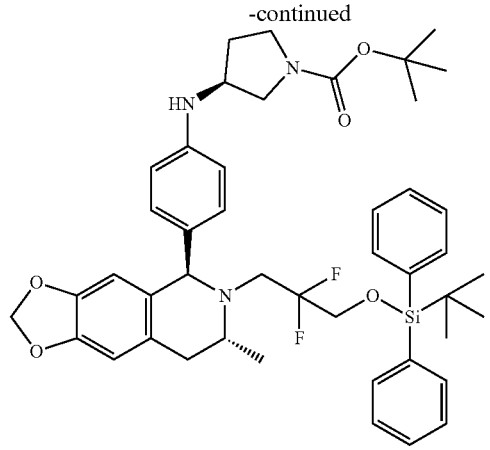

3e

3f

3g

-continued

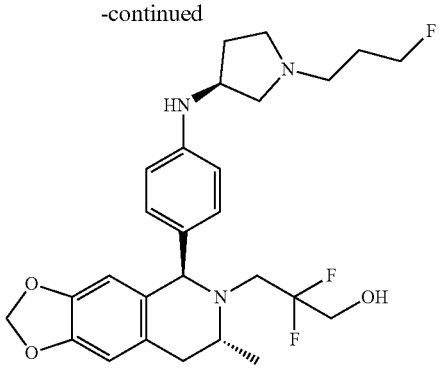

3

Step 1

(R)—N-(1-(3,4-bis(benzyloxy)phenyl)propan-2-yl)-3-((tert-butyldiphenylsilyl)oxy)-2,2-difluoropropan-1-amine 3a Compound 1d (1.0 g, 3.0 mmol) was dissolved in dioxane (20 mL), and diisopropylethylamine (1.2 g, 9.0 mmol) and 3-((tert-butyldiphenylsilyl)oxy)-2,2-difluoropropyltrifluoromethanesulfonate (1.0 g, 2.0 mmol, prepared by using the well-known method in "*Bioorganic &Medicinal Chemistry Letters,* 2018, 28(14), 2528-2532") were added. The reaction mixture was stirred in an oil bath at 80° C. in an argon atmosphere for 20 h. The reaction mixture was cooled and concentrated under reduced pressure. Saturated sodium bicarbonate solution (50 mL) was added, followed by the extraction with ethyl acetate (100 mL×2). The organic phases were combined, dried over anhydrous sodium sulfate, and filtered. The filtrate was concentrated under reduced pressure, and the resulting residue was purified by column chromatography with developing solvent system B to give the title compound 3a (1.7 g, 84% yield).

MS m/z (ESI): 680.2 [M+1].

Step 2

(R)-4-(2-((3-((tert-butyldiphenylsilyl)oxy)-2,2-difluoropropyl)amino)propyl)benzene-1,2-diol 3b Compound 3a (1.4 g, 2.0 mmol) was dissolved in methanol (10 mL), and palladium hydroxide on carbon (0.2 g) was added in an argon atmosphere. The reaction mixture was stirred under hydrogen balloon for 3 h, and filtered. The filtrate was concentrated under reduced pressure to give the title compound 3b (0.9 g, 94% yield).

Step 3

(1R,3R)-1-(4-bromophenyl)-2-(3-((tert-butyldiphenylsilyl)oxy)-2,2-difluoropropyl)-3-methyl-1,2,3,4-tetrahydroisoquinoline-6,7-diol 3c Compound 3b (0.8 g, 1.6 mmol) was dissolved in toluene (10 mL), and acetic acid (0.2 g, 3.2 mmol) and 4-bromobenzaldehyde (0.6 g, 3.2 mmol) were added. The reaction mixture was stirred in an oil bath at 80° C. for 16 h, and the reaction was terminated. The reaction mixture was cooled and concentrated under reduced pressure. Water (10 mL) was added, and the reaction mixture was adjusted to about pH 8 by slowly adding saturated sodium bicarbonate solution (20 mL) and extracted with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 3c (0.6 g, 56% yield).

MS m/z (ESI): 666.1 [M+1].

Step 4

(5R,7R)-5-(4-bromophenyl)-6-(3-((tert-butyldiphenylsilyl)oxy)-2,2-difluoropropyl)-7-methyl-5,6,7,8-tetrahydro-[1,3]dioxolo[4,5-g]isoquinoline 3d Compound 3c (0.2 g, 0.3 mmol) was dissolved in N,N-dimethylformamide (10 mL), and dibromomethane (0.07 g, 0.4 mmol) and cesium carbonate (0.1 g, 0.4 mmol) were added. The reaction mixture was stirred in an oil bath at 70° C. for 16 h, and the reaction was terminated. The reaction mixture was cooled and concentrated under reduced pressure. Water (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 3d (0.1 g, 47% yield).

Step 5 tert-Butyl (S)-3-((4-((5R,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)phenyl)amino)pyrrolidine-1-carboxylate 3e Compound 3d (60 mg, 0.09 mmol) was dissolved in dioxane (10 mL), and tert-butyl (S)-3-aminopyrrolidine-1-carboxylate (19 mg, 0.1 mmol), 2,2'-bis-(diphenylphosphino)-1,1'-binaphthyl (12 mg, 0.02 mmol), tris(dibenzylideneacetone)dipalladium(0) (20 mg, 0.02 mmol) and sodium tert-butoxide (29 mg, 0.3 mmol) were added. The reaction mixture was stirred in an oil bath at 80° C. in an argon atmosphere for 16 h, and the reaction was terminated. The reaction mixture was cooled and concentrated. Saturated sodium bicarbonate solution (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 3e (39 mg, 55% yield).

MS m/z (ESI): 784.3 [M+1].

Step 6

(S)—N-(4-((5R,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)phenyl)pyrrolidin-3-amine 3f Compound 3e (39 mg, 0.05 mmol) was dissolved in dichloromethane (5 mL), and a 5 M solution of hydrogen chloride in 1,4-dioxane (1 mL) was added dropwise in an ice bath. After addition, the reaction mixture was stirred at room temperature for 1.5 h and concentrated under reduced pressure. Saturated sodium bicarbonate solution (5 mL) was added, followed by the extraction with ethyl acetate (5 mL×3). The organic phases were combined, washed with saturated sodium chloride solution (5 mL), dried over anhydrous sodium sulfate, and filtered. The filtrate was concentrated under reduced pressure to give the title compound 3f (32 mg, 93% yield).

Step 7

(S)—N-(4-((5R,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)phenyl)-1-(3-fluoropropyl)pyrrolidin-3-amine 3g Compound 3f (32 mg, 0.04 mmol) was dissolved in N,N-dimethylformamide (5 mL), and diisopropylethylamine (4 mg, 0.05 mmol) was added, followed by the dropwise addition of 1-fluoro-3-iodopropane (10 mg, 0.05 mmol). The reaction mixture was stirred for 12 h. Water (5 mL) was added, followed by the extraction with ethyl acetate (5 mL×3). The organic phases were combined, washed with water (5 mL×2) and saturated sodium chloride solution (5 mL), dried over anhydrous sodium sulfate, and filtered. The filtrate was concentrated under reduced pressure, and the resulting residue was purified by column chromatography with developing solvent system B to give the title compound 3g (22 mg, 73% yield).

Step 8

2,2-Difluoro-3-((5R,7R)-5-(4-(((S)-1-(3-fluoropropyl)pyrrolidin-3-yl)amino)phenyl)-7-methyl-7,8-dihydro-[1,3]dioxolo[4,5-g]isoquinolin-6(5H)-yl)propan-1-ol 3

Compound 3g (20 mg, 0.03 mmol) was dissolved in dichloromethane (5 mL), and a 1 M solution of n-tetrabutylammonium fluoride in tetrahydrofuran (1 mL) was added dropwise in an ice bath. After addition, the reaction mixture was stirred at room temperature for 1.5 h and concentrated under reduced pressure. Saturated sodium bicarbonate solution (5 mL) was added, followed by the extraction with ethyl acetate (5 mL×3). The organic phases were combined, washed with saturated sodium chloride solution (5 mL), dried over anhydrous sodium sulfate, and filtered. The filtrate was concentrated under reduced pressure, and the resulting residue was purified by column chromatography with developing solvent system B to give the title compound 3 (5 mg, 33% yield).

MS m/z (ESI): 506.3 [M+1].

1H NMR (400 MHz, CD$_3$OD) 6.84 (d, 2H), 6.49 (s, 1H), 6.45 (d, 2H), 6.17 (s, 1H), 5.75 (s, 2H), 4.67 (s, 1H), 4.45-4.42 (m, 1H), 4.34-4.31 (m, 1H), 3.96-3.93 (m, 1H), 3.72-3.69 (m, 1H), 3.57-3.54 (m, 1H), 2.99-2.89 (m, 2H), 2.70-2.61 (m, 6H), 2.43-2.40 (m, 2H), 1.89-1.67 (m, 5H), 0.91 (d, 3H).

Example 4
2,2-Difluoro-3-(((5S,7R)-5-(5-(((S)-1-(3-fluoropropyl)pyrrolidin-3-yl)amino)pyridin-2-yl)-7-methyl-7,8-dihydro-[1,3]dioxolo[4,5-g]isoquinolin-6(5H)-yl)propan-1-ol 4
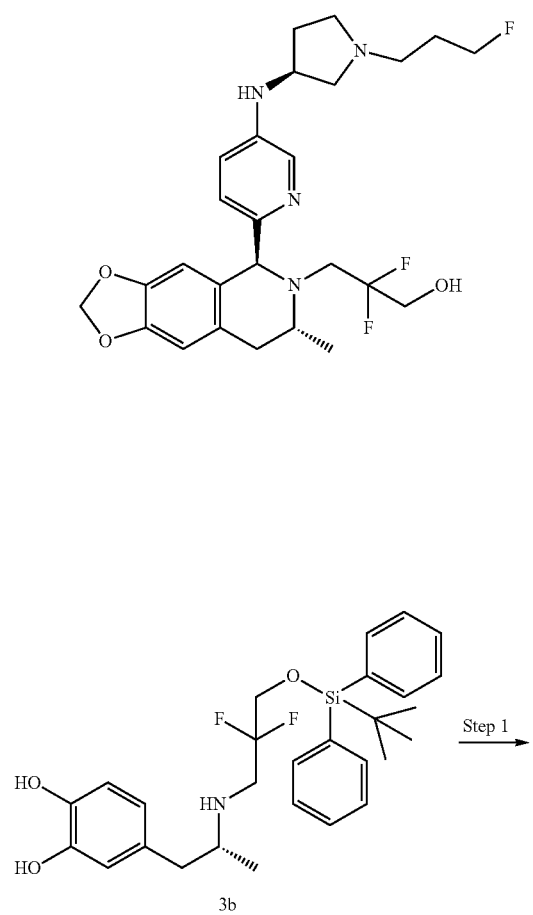
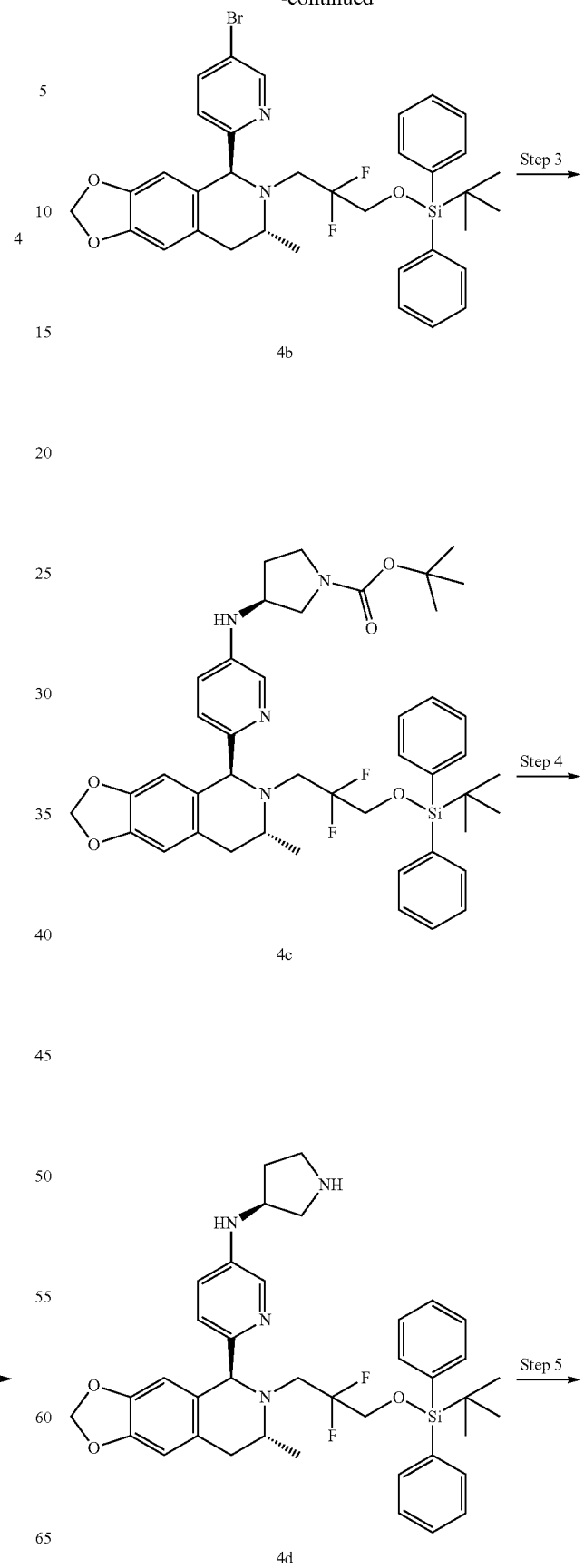

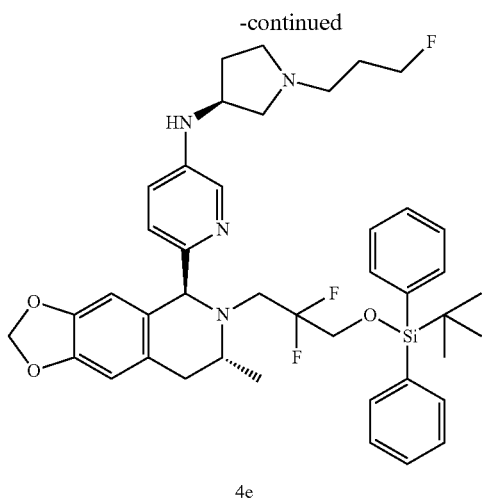

4e

4

Step 1

(1S,3R)-1-(5-bromopyridin-2-yl)-2-(3-((tert-butyldiphenylsilyl)oxy)-2,2-difluoropropyl)-3-methyl-1,2,3,4-tetrahydroisoquinoline-6,7-diol 4a The title compound 4a (256 mg, 75% yield) was obtained by following the synthesis scheme of Example 3 with the starting material 4-bromo-benzaldehyde in step 3 replaced by 5-bromopyridylaldehyde.
MS m/z (ESI): 667.1 [M+1].

Step 2

(5S,7R)-5-(5-bromopyridin-2-yl)-6-(3-((tert-butyldiphenylsilyl)oxy)-2,2-difluoropropyl)-7-methyl-5,6,7,8-tetrahydro-[1,3]dioxolo[4,5-g]isoquinoline 4b The title compound 4b (163 mg, 65% yield) was obtained by following the synthesis scheme of Example 3 with the compound 3c in step 4 replaced by compound 4a.

Step 3 tert-Butyl (S)-3-((6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)pyridin-yl)amino)pyrrolidine-1-carboxylate 4c The title compound 4c (40 mg, 68% yield) was obtained by following the synthesis scheme of Example 3 with the compound 3d in step 5 replaced by compound 4b.
MS m/z (ESI): 785.3 [M+1].

Step 4

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-N—((S)-pyrrolidin-3-yl)pyridin-3-amine 4d The title compound 4d (30 mg, 95% yield) was obtained by following the synthesis scheme of Example 3 with the compound 3e in step 6 replaced by compound 4c.

Step 5

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-N—((S)-1-(3-fluoropropyl)pyrrolidin-3-yl)pyridin-3-amine 4e The title compound 4e (25 mg, 75% yield) was obtained by following the synthesis scheme of Example 3 with the compound 3f in step 7 replaced by compound 4d.

Step 6

2,2-Difluoro-3-((5S,7R)-5-(5-(((S)-1-(3-fluoropropyl)pyrrolidin-3-yl)amino)pyridin-2-yl)-7-methyl-7,8-dihydro-[1,3]dioxolo[4,5-g]isoquinolin-6(5H)-yl)propan-1-ol 4

The title compound 4 (5 mg, 29% yield) was obtained by following the synthesis scheme of Example 3 with the compound 3g in step 8 replaced by compound 4e.
MS m/z (ESI): 507.2 [M+1].
1H NMR (400 MHz, CD3OD) 7.84 (s, 1H), 7.05-6.96 (m, 2H), 6.62 (s, 1H), 6.21 (s, 1H), 5.86 (d, 2H), 4.77 (s, 1H), 4.58-4.55 (m, 1H), 4.44-4.43 (m, 1H), 3.74-3.71 (m, 1H), 3.62-3.58 (m, 1H), 3.26-3.24 (m, 2H), 2.97-2.95 (m, 2H), 2.76-2.52 (m, 6H), 1.72-1.64 (m, 4H), 1.45-1.43 (m, 2H), 0.92 (d, 3H).

Example 5

3-(5S,7R)-5-(2,6-difluoro-4-(((S)-1-(3-fluoropropyl)pyrrolidin-3-yl)amino)phenyl)-7-methyl-7,8-dihydro-[1,3]dioxolo[4,5-g]isoquinolin-6(5H)-yl)-2,2-difluoropropan-1-ol 5

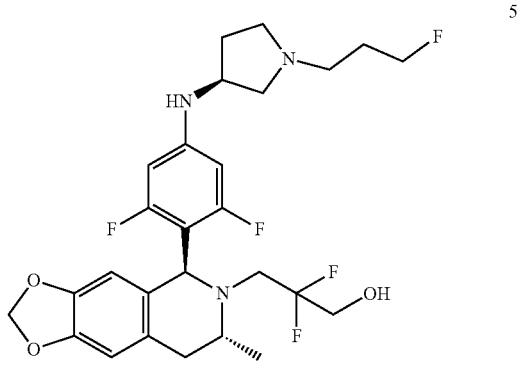 [SMILES: C[C@@H]1Cc2cc3c(cc2[C@@H](c2c(F)cc(N[C@H]4CCN(CCCF)C4)cc2F)N1CC(F)(F)CO)OCO3]

5

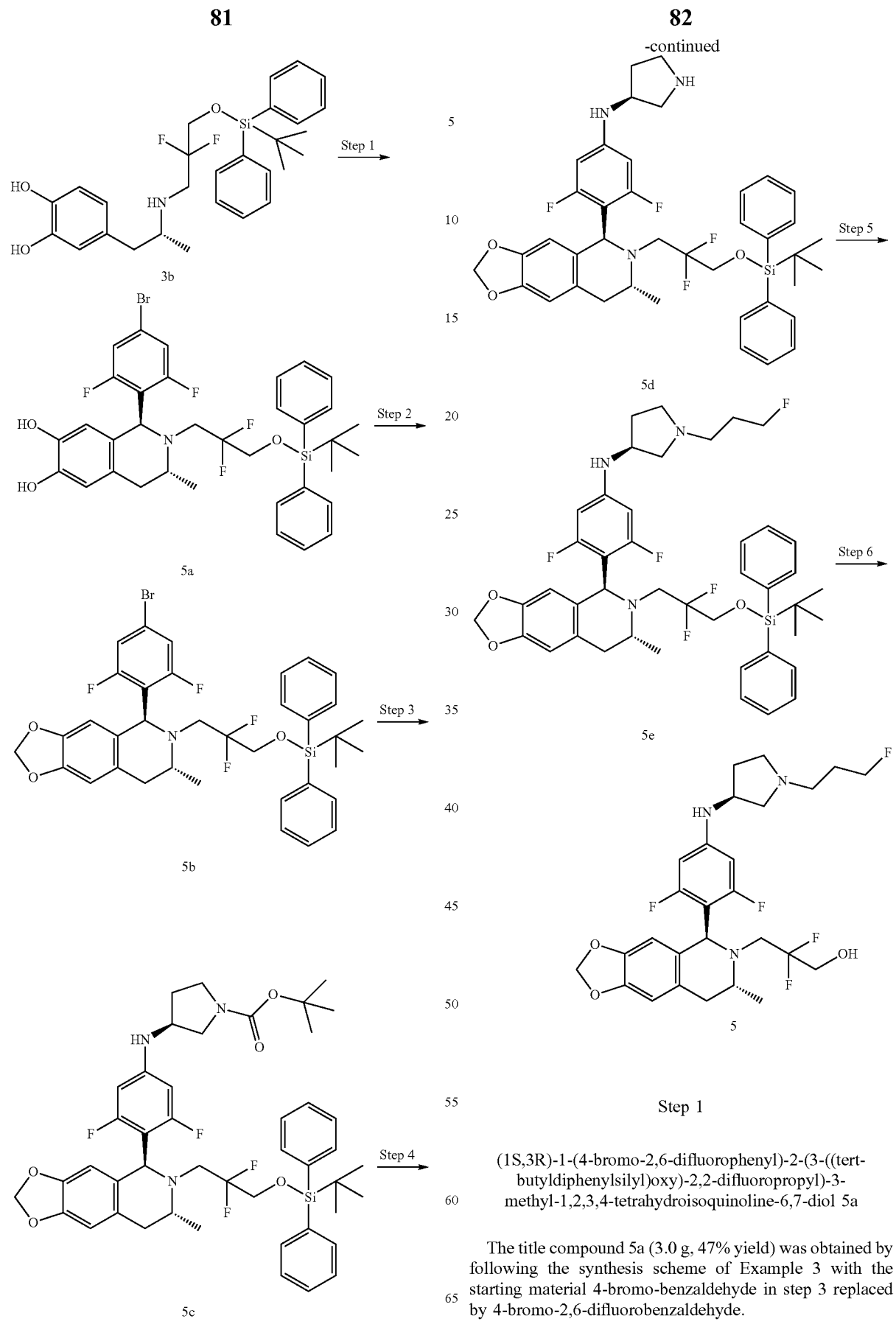
Step 1
(1S,3R)-1-(4-bromo-2,6-difluorophenyl)-2-(3-((tert-butyldiphenylsilyl)oxy)-2,2-difluoropropyl)-3-methyl-1,2,3,4-tetrahydroisoquinoline-6,7-diol 5a
The title compound 5a (3.0 g, 47% yield) was obtained by following the synthesis scheme of Example 3 with the starting material 4-bromo-benzaldehyde in step 3 replaced by 4-bromo-2,6-difluorobenzaldehyde.
MS m/z (ESI): 702.0 [M+1].

Step 2

(5S,7R)-5-(4-bromo-2,6-difluorophenyl)-6-(3-((tert-butyldiphenylsilyl)oxy)-2,2-difluoropropyl)-7-methyl-5,6,7,8-tetrahydro-[1,3]dioxolo[4,5-g]isoquinoline 5b The title compound 5b (1.6 g, 55% yield) was obtained by following the synthesis scheme of Example 3 with the compound 3c in step 4 replaced by compound 5a.

Step 3 tert-Butyl (S)-3-((4-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-3,5-difluorophenyl)amino)pyrrolidine-1-carboxylate 5c The title compound 5c (1.5 g, 65% yield) was obtained by following the synthesis scheme of Example 3 with the compound 3d in step 5 replaced by compound 5b.
MS m/z (ESI): 820.3 [M+1].

Step 4

(S)—N-(4-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-3,5-difluorophenyl)pyrrolidin-3-amine 5d The title compound 5d (1.3 g, 99% yield) was obtained by following the synthesis scheme of Example 3 with the compound 3e in step 6 replaced by compound 5c.

Step 5

(S)—N-(4-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-3,5-difluorophenyl)-1-(3-fluoropropyl)pyrrolidin-3-amine 5e The title compound 5e (1.2 g, 92% yield) was obtained by following the synthesis scheme of Example 3 with the compound 3f in step 7 replaced by compound 5d.

Step 6

3-((5S,7R)-5-(2,6-difluoro-4-(((S)-1-(3-fluoropropyl)pyrrolidin-3-yl)amino)phenyl)-7-methyl-7,8-dihydro-[1,3]dioxolo[4,5-g]isoquinolin-6(5H)-yl)-2,2-difluoro-1-propanol 5

The title compound 5 (300 mg, 36% yield) was obtained by following the synthesis scheme of Example 3 with the compound 3g in step 8 replaced by compound 5e.
MS m/z (ESI): 542.2 [M+1].
$^1$H NMR (400 MHz, CD$_3$OD) 6.56 (s, 1H), 6.18-6.16 (m, 3H), 5.86-5.84 (m, 2H), 4.99 (s, 1H), 4.59-4.56 (m, 1H), 4.49-4.47 (m, 1H), 4.05 (br, 1H), 3.84-3.71 (m, 2H), 3.55-3.53 (m, 2H), 3.15-3.07 (m, 3H), 2.88-2.68 (m, 4H), 2.53-2.38 (m, 2H), 2.03-1.96 (m, 2H), 1.84 (br, 1H), 1.40-1.31 (m, 1H), 1.06 (d, 3H).

Example 6

N—((S-1-(3-fluoropropyl)pyrrolidin-3-yl)-6-((5S,7R)-7-methyl-6-(2,2,2-trifluoroethyl)-5,6,7,8-tetrahydro-[1,3]dioxolo[4,5-g]isoquinolin-5-yl)pyridin-3-amine 6

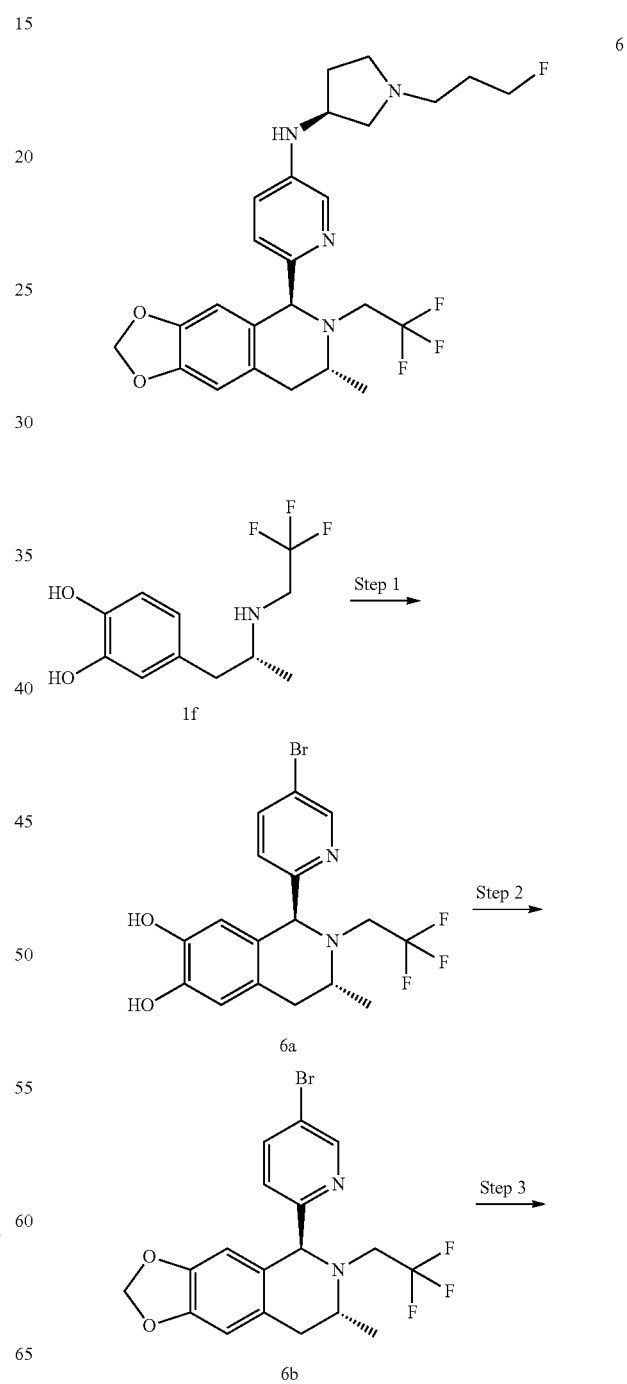

85
-continued

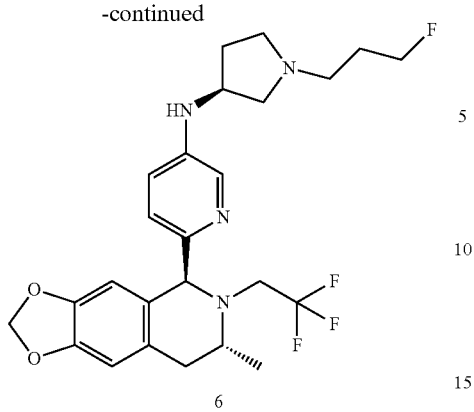

6

Step 1

(1S,3R)-1-(5-bromopyridin-2-yl)-3-methyl-2-(2,2,2-threefluoroethyl)-1,2,3,4-tetrahydroisoquinoline-6,7-diol 6a The title compound 6a (600 mg, 60% yield) was obtained by following the synthesis scheme of Example 2 with the starting material 4-bromo-2,6-difluorobenzaldehyde in step 1 replaced by 5-bromopyridylaldehyde.

MS m/z (ESI): 417.0 [M+1].

Step 2

(5S,7R)-5-(5-bromopyridin-2-yl)-7-methyl-6-(2,2,2-trifluoroethyl)-5,6,7,8-tetrahydro-[1,3]dioxolo[4,5-g]isoquinoline 6b The title compound 6b (450 mg, 73% yield) was obtained by following the synthesis scheme of Example 2 with the compound 2a in step 2 replaced by compound 6a. MS m/z (ESI): 431.0 [M+1].

Step 3

N—((S)-1-(3-fluoropropyl)pyrrolidin-3-yl)-6-((5S,7R)-7-methyl-6-(2,2,2-trifluoroethyl)-5,6,7,8-tetrahydro-[1,3]dioxolo[4,5-g]isoquinolin-5-yl)pyridin-3-amine 6

The title compound 6 (200 mg, 44% yield) was obtained by following the synthesis scheme of Example 2 with the compound 2b in step 2 replaced by compound 6b.

MS m/z (ESI): 495.2 [M+1].

$^1$H NMR (400 MHz, CD$_3$OD) 7.81 (s, 1H), 7.12 (d, 1H), 7.00 (d, 1H), 6.60 (s, 1H), 6.21 (s, 1H), 5.86 (d, 2H), 4.76 (s, 1H), 4.56-4.54 (m, 1H), 4.43-4.41 (m, 1H), 4.01-4.00 (m, 1H), 3.47-3.31 (m, 2H), 3.14-3.11 (m, 1H), 2.94-2.61 (m, 8H), 2.37-2.35 (m, 1H), 1.96-1.90 (m, 2H), 1.88-1.74 (m, 1H), 1.08 (d, 3H).

Example 7

(S)—N-(4-((5S,7R)-2,2-difluoro-7-methyl-6-(2,2,2-trifluoroethyl)-5,6,7,8-tetrahydro-[1,3]dioxolo[4,5-g]isoquinolin-5-yl)-3,5-difluorophenyl)-1-(3-fluoropropyl)pyrrolidin amine 7

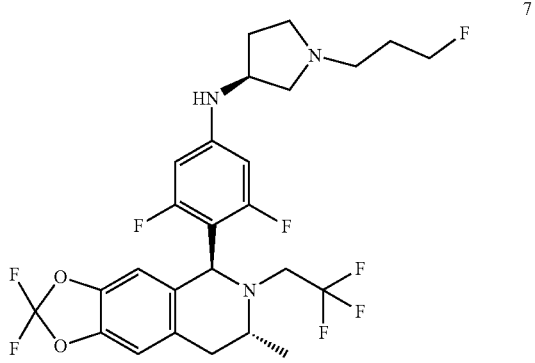 [SMILES: C[C@@H]1Cc2cc3c(cc2[C@@H](c2c(F)cc(N[C@H]4CCN(CCCF)C4)cc2F)N1CC(F)(F)F)OC(F)(F)O3]

7

Example 8

6-((5S,7R)-2,2-difluoro-7-methyl-6-(2,2,2-trifluoroethyl)-5,6,7,8-tetrahydro-[1,3]dioxolo[4,5-g]isoquinolin-5-yl)-N—((S)-1-(3-fluoropropyl)pyrrolidin-3-yl)pyridin-3-amine 8

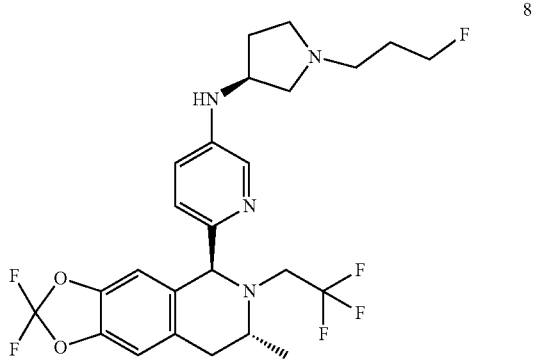 [SMILES: C[C@@H]1Cc2cc3c(cc2[C@@H](c2ccc(N[C@H]4CCN(CCCF)C4)cn2)N1CC(F)(F)F)OC(F)(F)O3]

8

Example 9

5-Fluoro-N—((S)-1-(3-fluoropropyl)pyrrolidin-3-yl)-6-((5S,7R)-7-methyl-6-(2,2,2-trifluoroethyl)-5,6,7,8-tetrahydro-[1,3]dioxolo[4,5-g]isoquinolin-5-yl)pyridin-3-amine 9

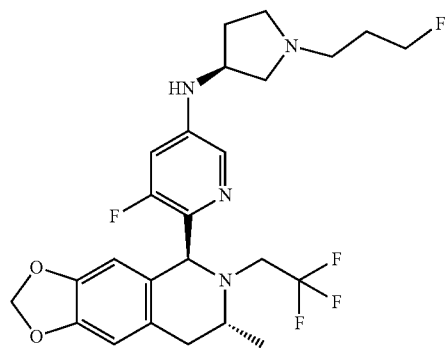

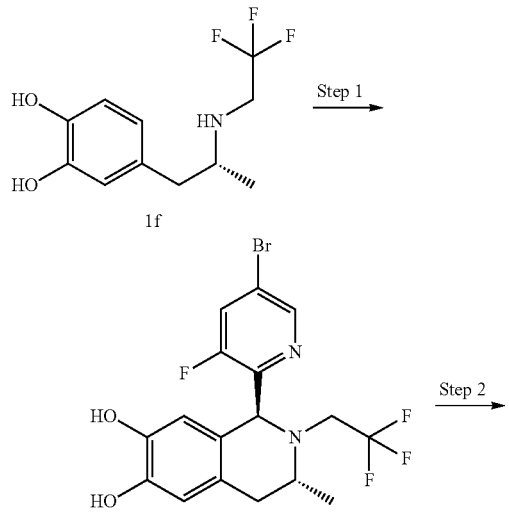

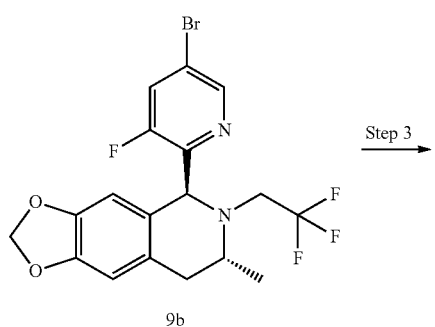

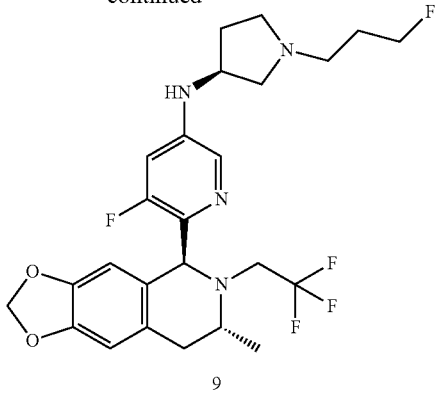

Step 1

(1S,3R)-1-(5-bromo-3-fluoropyridin-2-yl)-3-methyl-2-(2,2,2-trifluoroethyl)-1,2,3,4-tetrahydroisoquinoline-6,7-diol 9a The title compound 9a (115 mg, 55% yield) was obtained by following the synthesis scheme of Example 2 with the starting material 4-bromo-2,6-difluorobenzaldehyde in step 1 replaced by 5-bromo-3-fluoropyridyl-2-aldehyde.

Step 2

(5S,7R)-5-(5-bromo-3-fluoropyridin-2-yl)-7-methyl-6-(2,2,2-trifluoroethyl)-5,6,7,8-tetrahydro-[1,3]dioxolo[4,5-g]isoquinoline 9b The title compound 9b (58 mg, 58% yield) was obtained by following the synthesis scheme of Example 2 with the compound 2a in step 2 replaced by compound 9a.

Step 3

5-Fluoro-N—((S)-1-(3-fluoropropyl)pyrrolidin-3-yl)-6-((5S,7R)-7-methyl-6-(2,2,2-trifluoroethyl)-5,6,7,8-tetrahydro-[1,3]dioxolo[4,5-g]isoquinolin-5-yl)pyridin-3-amine 9

The title compound 9 (18 mg, 48% yield) was obtained by following the synthesis scheme of Example 2 with the compound 2b in step 3 replaced by compound 9b.

MS m/z (ESI): 513.2 [M+1].

$^1$H NMR (400 MHz, CD$_3$OD) 7.66-7.65 (m, 1H), 6.74-6.73 (m, 1H), 6.61 (s, 1H), 6.18 (s, 1H), 5.85 (d, 2H), 4.56-4.54 (m, 1H), 4.46-4.44 (m, 1H), 4.00-3.97 (m, 1H), 3.53-3.51 (m, 1H), 3.32-3.29 (m, 2H), 3.06-3.02 (m, 1H), 2.98-2.92 (m, 2H), 2.79-2.76 (m, 1H), 2.66-2.60 (m, 3H), 2.56-2.51 (m, 2H), 2.36-2.35 (m, 1H), 1.96-1.88 (m, 2H), 1.74-1.73 (m, 1H), 1.07 (d, 3H).

Example 10
3-((5S,7R)-5-(2,6-difluoro-4-(((S)-1-(3-fluoropropyl)pyrrolidin-3-yl)amino)phenyl)-2,2,7-trimethyl-7,8-dihydro-[1,3]dioxolo[4,5-g]isoquinolin-6(5H)-yl)-2,2-difluoropropan-1-ol 10
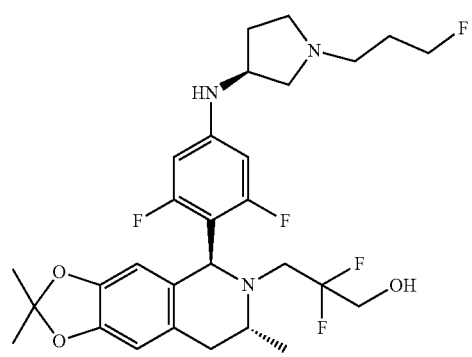
Example 11
2,2-Difluoro-3-((5S,7R)-5-(3-fluoro-5-(((S)-1-(3-fluoropropyl)pyrrolidin-3-yl)amino)pyridin-2-yl)-7-methyl-7,8-dihydro-[1,3]dioxolo[4,5-g]isoquinolin-6(5H)-yl)propan-1-ol 11
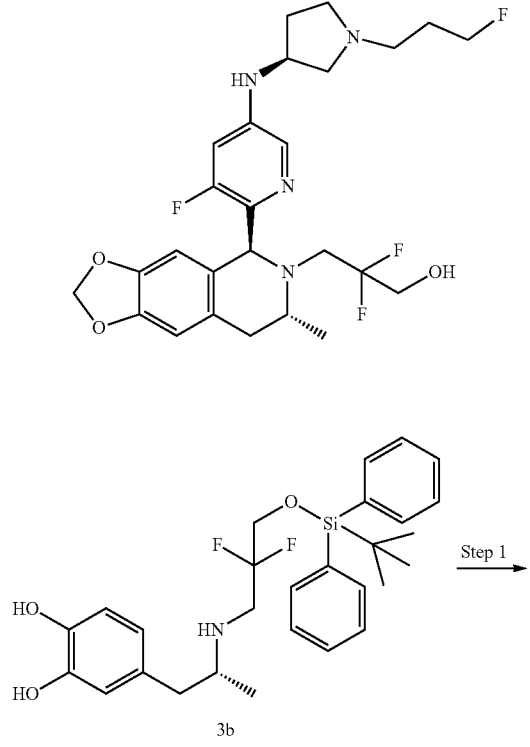
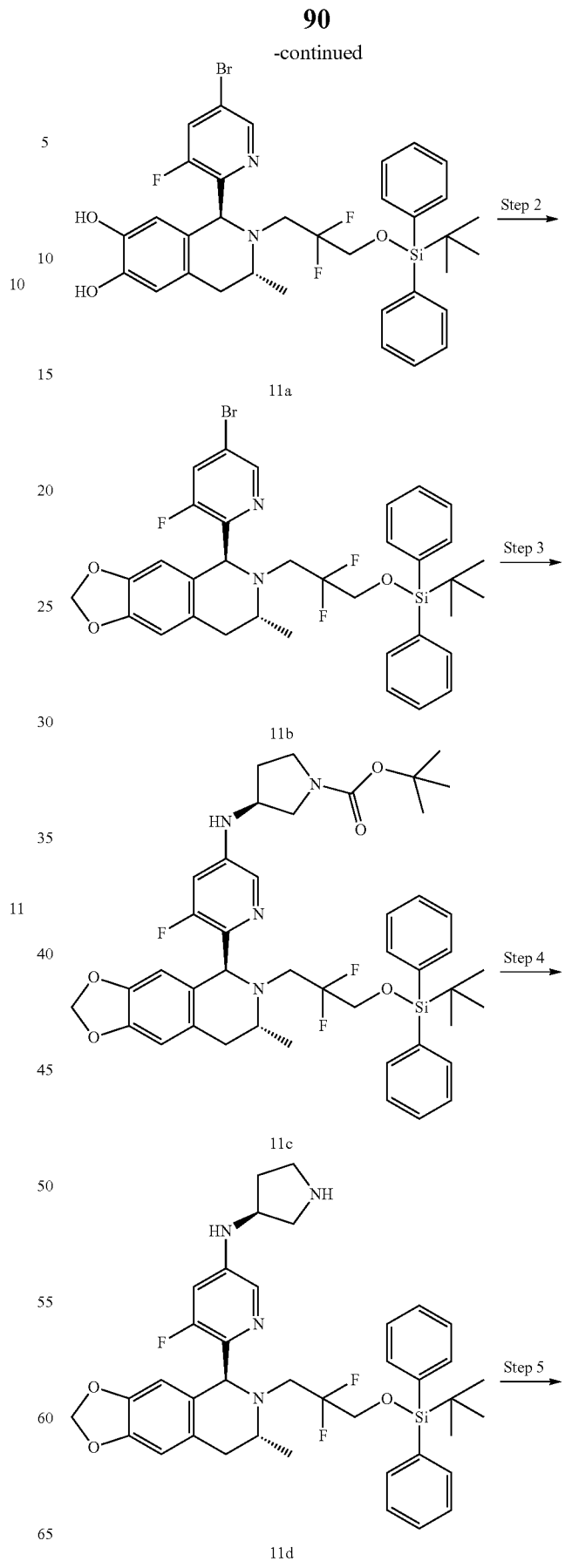

-continued

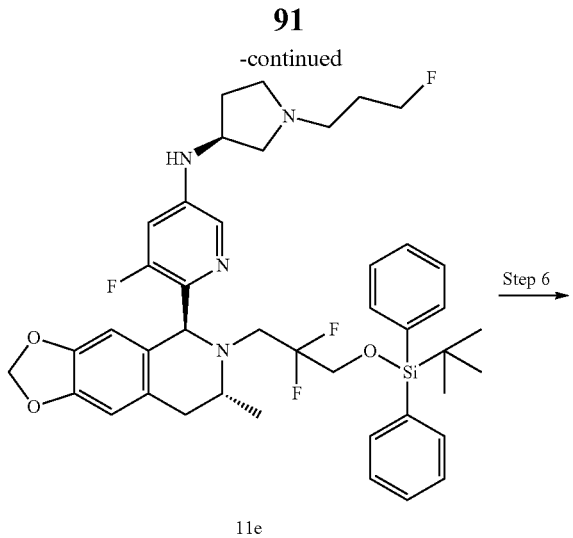

11e

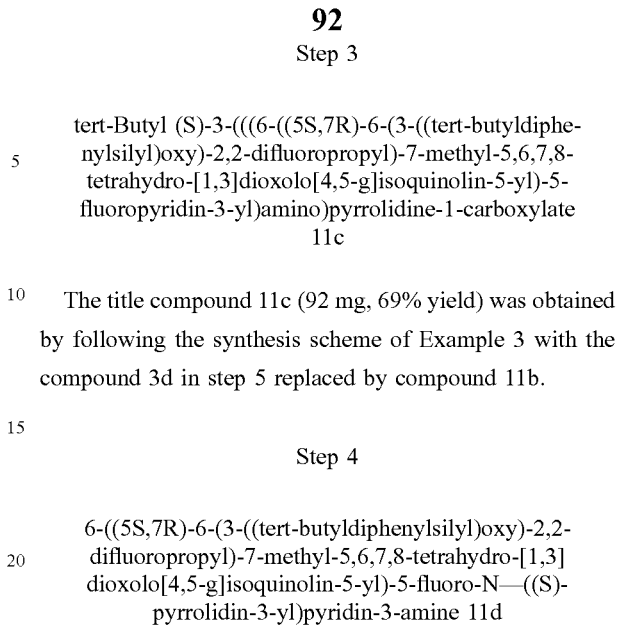

11

Step 1

(1S,3R)-1-(5-bromo-3-fluoropyridin-2-yl)-2-(3-((tert-butyldiphenylsilyl)oxy)-2,2-difluoropropyl)-3-methyl-1,2,3,4-tetrahydroisoquinoline-6,7-diol 11a The title compound 11a (356 mg, 71% yield) was obtained by following the synthesis scheme of Example 3 with the starting material 4-bromo-benzaldehyde in step 3 replaced by 5-bromo-3-fluoropyridylaldehyde.

MS m/z (ESI): 685.1 [M+1].

Step 2

(5S,7R)-5-(5-bromo-3-fluoropyridin-2-yl)-6-(3-((tert-butyldiphenylsilyl)oxy)-2,2-difluoropropyl)-7-methyl-5,6,7,8-tetrahydro-[1,3]dioxolo[4,5-g]isoquinoline 11b The title compound 11b (169 mg, 61% yield) was obtained by following the synthesis scheme of Example 3 with the compound 3c in step 4 replaced by compound 11a.

Step 3 tert-Butyl (S)-3-(((6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-5-fluoropyridin-3-yl)amino)pyrrolidine-1-carboxylate 11c The title compound 11c (92 mg, 69% yield) was obtained by following the synthesis scheme of Example 3 with the compound 3d in step 5 replaced by compound 11b.

Step 4

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-5-fluoro-N—((S)-pyrrolidin-3-yl)pyridin-3-amine 11d The title compound 11d (62 mg, 95% yield) was obtained by following the synthesis scheme of Example 3 with the compound 3e in step 6 replaced by compound 11c.

Step 5

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-5-fluoro-N—((S)-1-(3-fluoropropyl)pyrrolidin-3-yl)pyridin-3-amine 11e The title compound 11e (35 mg, 71% yield) was obtained by following the synthesis scheme of Example 3 with the compound 3f in step 7 replaced by compound 11d.

Step 6

2,2-Difluoro-3-((5S,7R)-5-(3-fluoro-5-(((S)-1-(3-fluoropropyl)pyrrolidin-3-yl)amino)pyridin-2-yl)-7-methyl-7,8-dihydro-[1,3]dioxolo[4,5-g]isoquinolin-6(5H)-yl)propan-1-ol 11

The title compound 11 (15 mg, 39% yield) was obtained by following the synthesis scheme of Example 3 with the compound 3g in step 8 replaced by compound 11e.

MS m/z (ESI): 525.2 [M+1].

$^1$H NMR (400 MHz, CD$_3$OD) 7.68-7.67 (m, 1H), 6.76-6.73 (m, 1H), 6.60 (s, 1H), 6.15 (s, 1H), 5.85 (d, 2H), 4.56-4.54 (m, 1H), 4.47-4.44 (m, 1H), 4.01-3.98 (m, 1H), 3.75-3.70 (m, 1H), 3.60-3.52 (m, 2H), 3.13-2.95 (m, 4H), 2.80-2.51 (m, 7H), 2.38-2.34 (m, 1H), 1.97-1.88 (m, 2H), 1.76-1.72 (m, 1H), 1.05 (d, 3H).

Example 12

2,2-Difluoro-3-((5S,7R)-5-(5-(((S)-1-(3-fluoropropyl)pyrrolidin-3-yl)amino)pyridin-2-yl)-7-methyl-7,8-dihydro-[1,3]dioxolo[4,5-g]isoquinolin-6(5H)-yl-2,2-th)propan-1-ol 12

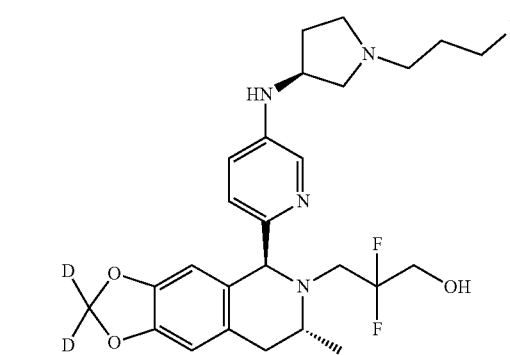

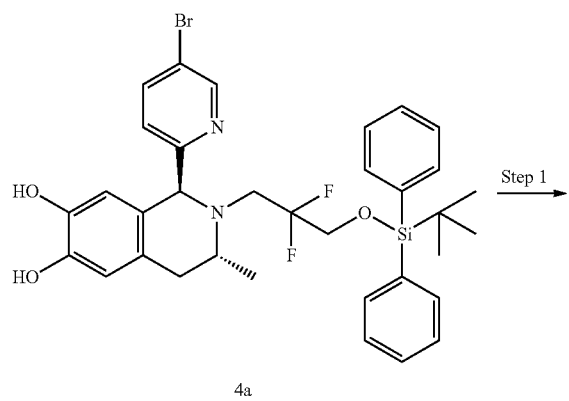

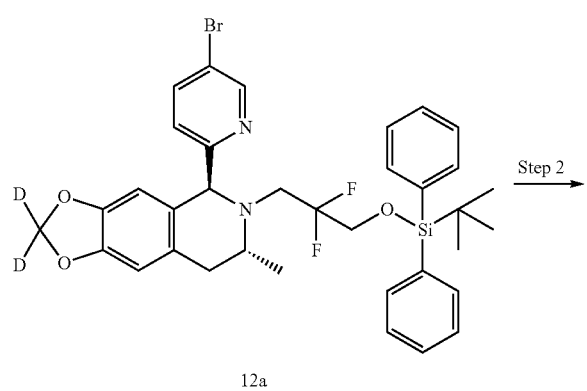

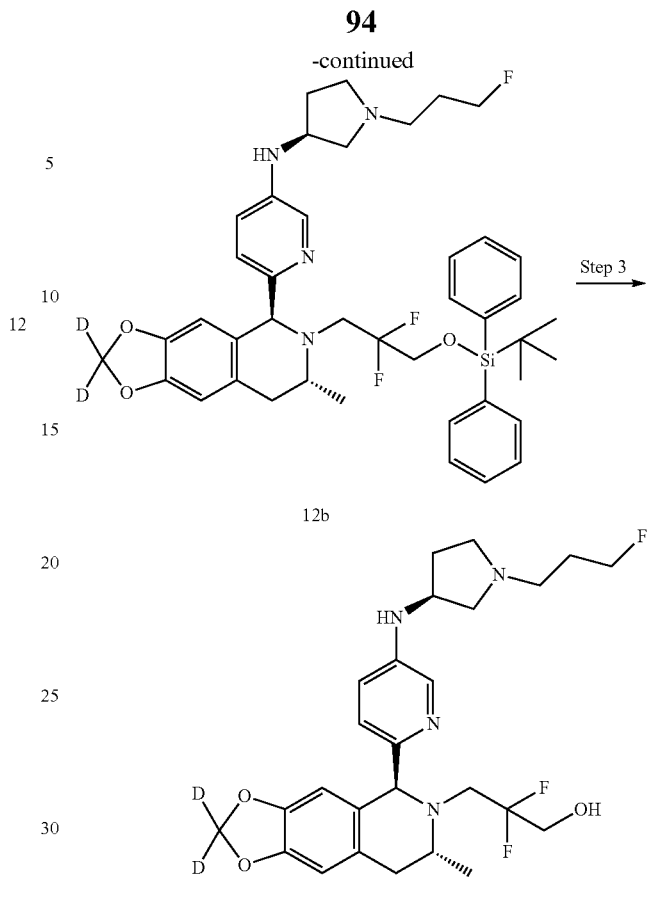

Step 1

(5S,7R)-5-(5-bromopyridin-2-yl)-6-(3-((tert-butyldiphenylsilyl)oxy)-2,2-difluoropropyl)-7-methyl-5,6,7,8-tetrahydro-[1,3]dioxolo[4,5-g]isoquinoline-2,2-th 12a Compound 4a (350 mg, 0.5 mmol) was dissolved in N,N-dimethylformamide (10 mL), and dibromodideuteromethane (277 mg, 1.6 mmol) and cesium carbonate (512 mg, 1.6 mmol) were added. The reaction mixture was stirred in an oil bath at 70° C. for 16 h, and the reaction was terminated. The reaction mixture was cooled and concentrated under reduced pressure. Water (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 12a (170 mg, 48% yield).

MS m/z (ESI): 681.1 [M+1].

Step 2

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl-2,2-$d_2$)—N—((S)-1-(3-fluoropropyl)pyrrolidin-3-yl)pyridin-3-amine 12b Compound 12a (170 mg, 0.25 mmol) was dissolved in dioxane (10 mL), and compound 1c (44 mg, 0.3 mmol), 2,2'-bis-(diphenylphosphino)-1,1'-binaphthyl (12 mg, 0.02 mmol), tris(dibenzylideneacetone)dipalladium(0) (20 mg, 0.02 mmol) and sodium tert-butoxide (29 mg, 0.3 mmol) were added. The reaction mixture was stirred in an oil bath at 80° C. in an argon atmosphere for 16 h, and the reaction was terminated. The reaction mixture was cooled and concentrated. Saturated sodium bicarbonate solution (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 12b (103 mg, 55% yield).

Step 3

2,2-Difluoro-3-((5S,7R)-5-(5-(((S)-1-(3-fluoropropyl)pyrrolidin-3-yl)amino)pyridin-2-yl)-7-methyl-7,8-dihydro-[1,3]dioxolo[4,5-g]isoquinolin-6(5H)-yl-2,2-th)propan-1-ol 12

Compound 12b (103 mg, 0.14 mmol) was dissolved in dichloromethane (5 mL), and a 1 M solution of n-tetrabutylammonium fluoride in tetrahydrofuran (1 mL) was added dropwise in an ice bath. After addition, the reaction mixture was stirred at room temperature for 1.5 h and concentrated under reduced pressure. Saturated sodium bicarbonate solution (5 mL) was added, followed by the extraction with ethyl acetate (5 mL×3). The organic phases were combined, washed with saturated sodium chloride solution (5 mL), dried over anhydrous sodium sulfate, and filtered. The filtrate was concentrated under reduced pressure, and the resulting residue was purified by column chromatography with developing solvent system B to give the title compound 12 (35 mg, 49% yield).

MS m/z (ESI): 509.1 [M+1].

$^1$H NMR (400 MHz, CD$_3$OD) 8.01 (dd, 1H), 7.68 (d, 1H), 7.63 (d, 1H), 6.74 (s, 1H), 6.47 (s, 1H), 5.19 (s, 1H), 4.64-4.62 (m, 1H), 4.54-4.52 (m, 1H), 4.42 (br, 1H), 3.83-3.71 (m, 5H), 3.45-3.41 (m, 5H), 3.09-3.05 (m, 1H), 2.91-2.82 (m, 1H), 2.67-2.62 (m, 1H), 2.21-2.12 (m, 4H), 1.14 (d, 3H).

Example 13

2,2-Difluoro-3-((5S,7R)-5-(5-((1-(3-fluoropropyl)azetidin-3-yl)amino)pyridin-2-yl)-7-methyl-7,8-dihydro-[1,3]dioxolo[4,5-g]isoquinolin-6(5H)-yl-2,2-th)propan-1-ol 13

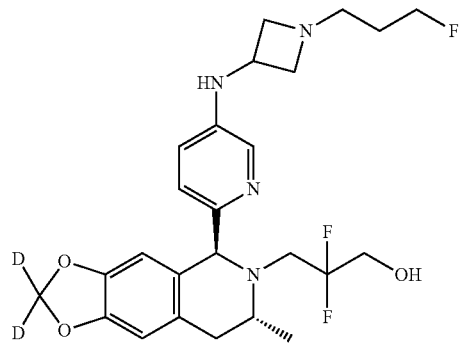

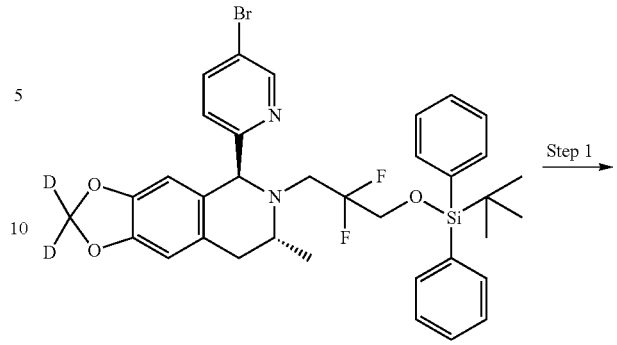

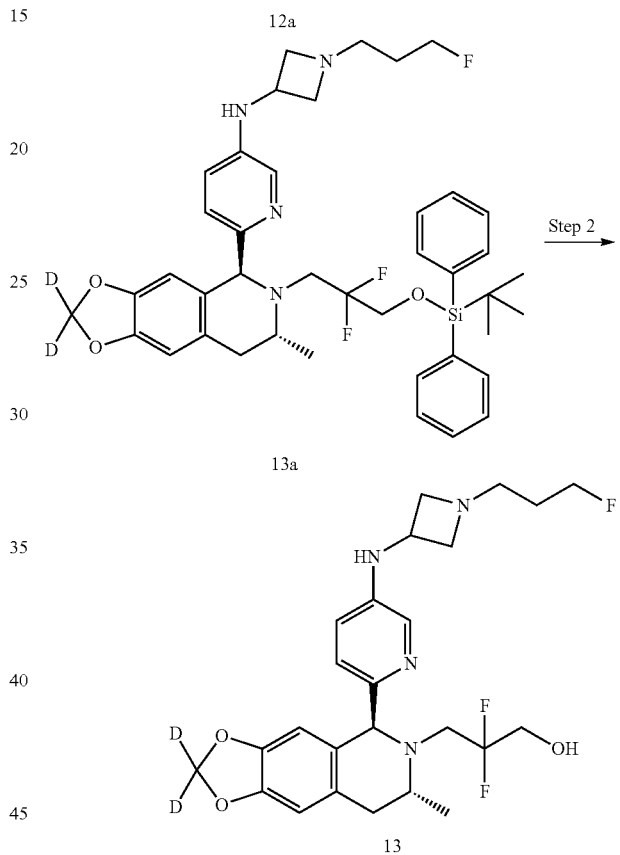

Step 1

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl-2,2-d$_2$)-N-(1-(3-fluoropropyl)azetidin-3-yl)pyridin-3-amine 13a Compound 12a (86 mg, 0.13 mmol) was dissolved in dioxane (10 mL), and the compound 1-(3-fluoropropyl)azetidin-3-amine (44 mg, 0.3 mmol, prepared as disclosed in "Example 1 on page 50 of the specification of Patent Application WO2019228443"), 2,2'-bis-(diphenylphosphino)-1,1'-binaphthyl (12 mg, 0.02 mmol), tris(dibenzylideneacetone)dipalladium(0) (20 mg, 0.02 mmol) and sodium tert-butoxide (29 mg, 0.3 mmol) were added. The reaction mixture was stirred in an oil bath at 80° C. in an argon atmosphere for 16 h, and the reaction was terminated. The reaction mixture was cooled and concentrated. Saturated sodium bicarbonate solution (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 13a (47 mg, 51% yield).

Step 2

2,2-Difluoro-3-((5S,7R)-5-(5-((1-(3-fluoropropyl) azetidin-3-yl)amino)pyridin-2-yl)-7-methyl-7,8-di- hydro-[1,3]dioxolo[4,5-g]isoquinolin-6(5H)-yl-2,2- d$_2$)propan-1-ol 13

Compound 13a (39 mg, 0.05 mmol) was dissolved in dichloromethane (5 mL), and a 1 M solution of n-tetrabutylammonium fluoride in tetrahydrofuran (1 mL) was added dropwise in an ice bath. After addition, the reaction mixture was stirred at room temperature for 1.5 h and concentrated under reduced pressure. Saturated sodium bicarbonate solution (5 mL) was added, followed by the extraction with ethyl acetate (5 mL×3). The organic phases were combined, washed with saturated sodium chloride solution (5 mL), dried over anhydrous sodium sulfate, and filtered. The filtrate was concentrated under reduced pressure, and the resulting residue was purified by column chromatography with developing solvent system B to give the title compound 13 (11 mg, 42% yield).

MS m/z (ESI): 495.2 [M+1].

$^1$H NMR (400 MHz, CD$_3$OD) 7.80 (d, 1H), 7.04 (d, 1H), 6.94 (dd, 1H), 6.61 (s, 1H), 6.19 (s, 1H), 4.64 (br, 2H), 4.54-4.52 (m, 1H), 4.45-4.42 (m, 1H), 4.15-4.10 (m, 1H), 3.85-3.83 (m, 2H), 3.76-3.68 (m, 1H), 3.64-3.56 (m, 1H), 3.14-2.97 (m, 4H), 2.78-2.68 (m, 3H), 2.59-2.52 (m, 1H), 1.84-1.74 (m, 2H), 1.05 (d, 3H).

Example 14

2,2-Difluoro-3-((5S,7R)-5-(5-((1-(3-fluoropropyl) azetidin-3-yl)amino)pyridin-2-yl)-7-methyl-7,8-di- hydro-[1,3]dioxolo[4,5-g]isoquinolin-6(5H)-yl)pro- pan-1-ol 14

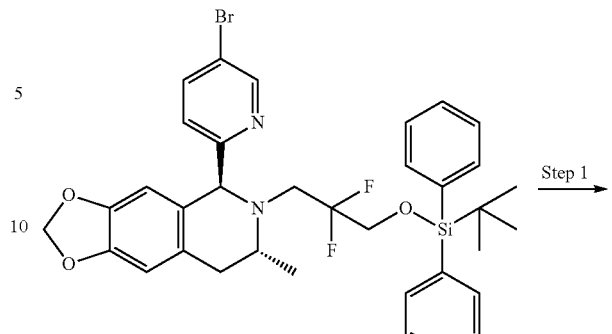

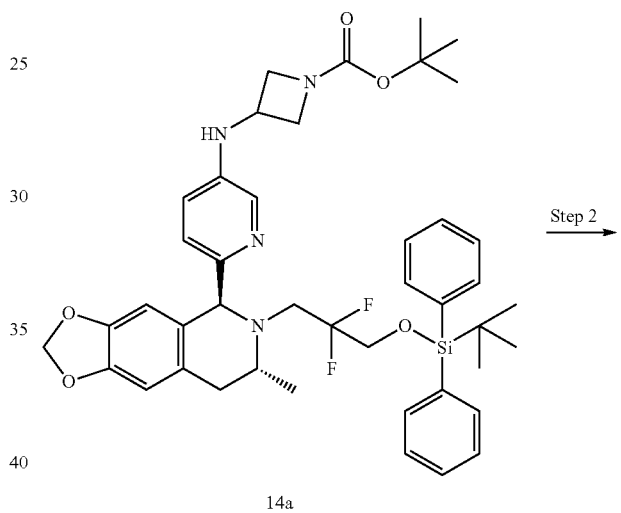

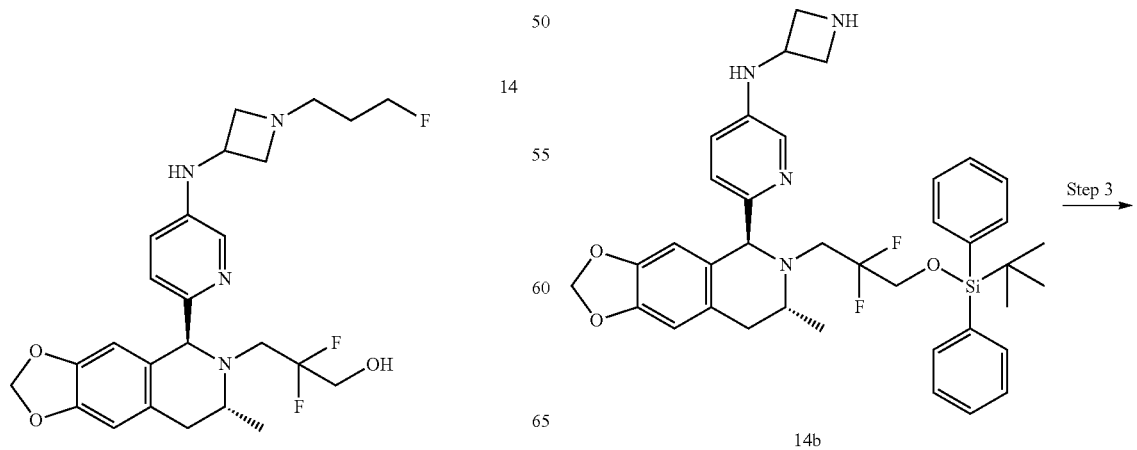

-continued

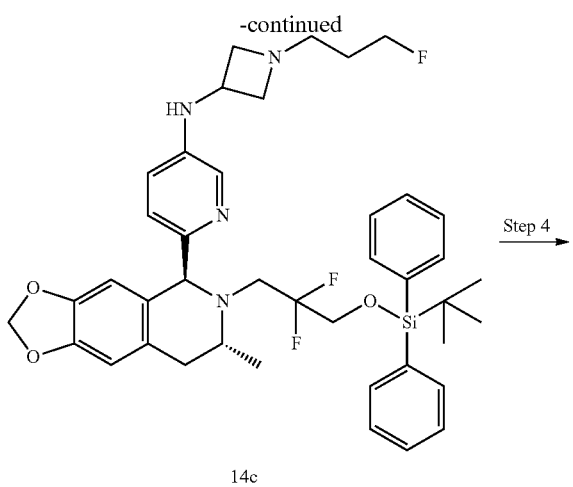

14c

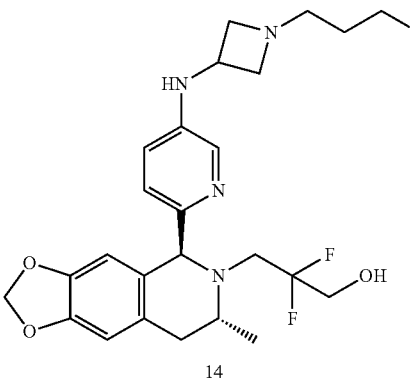

14

Step 1 tert-Butyl 3-((6-((5S,7R)-6-(3-((tert-butyldiphenylsi-lyl)oxy)-2,2-difluoropropyl)-7-methyl-5,6,7,8-tetra-hydro-[1,3]dioxolo[4,5-g]isoquinolin-5-yl)pyridin-3-yl)amino)azetidine carboxylate 14a Compound 4b (1.8 g, 2.65 mmol) was dissolved in toluene (50 mL), and tert-butyl 3-aminoazetidine-1-car-boxylate (0.9 g, 5.21 mmol), 2,2'-bis-(diphenylphosphino)-1,1'-binaphthyl (165 mg, 0.26 mmol), tris(dibenzylideneac-etone)dipalladium(0) (243 mg, 0.26 mmol) and sodium tert-butoxide (763 mg, 7.95 mmol) were added. The reaction mixture was stirred in an oil bath at 80° C. in an argon atmosphere for 16 h, and the reaction was terminated. The reaction mixture was cooled and concentrated. Saturated sodium bicarbonate solution (50 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 14a (1.2 g, 59% yield).

MS m/z (ESI): 771.2 [M+1].

Step 2

N-(azetidin-3-yl)-6-((5S,7R)-6-(3-((tert-butyldiphe-nylsilyl)oxy)-2,2-difluoropropyl)-7-methyl-5,6,7,8-tetrahydro-[1,3]dioxolo[4,5-g]isoquinolin-5-yl)pyri-din-3-amine 14b Compound 14a (1.2 g, 1.56 mmol) was dissolved in dichloromethane (25 mL), and a 4 M solution of hydrogen chloride in 1,4-dioxane (2 mL) was added dropwise in an ice bath. After addition, the reaction mixture was stirred at room temperature for 1.5 h and concentrated under reduced pressure. Saturated sodium bicarbonate solution (15 mL) was added, followed by the extraction with ethyl acetate (15 mL×3). The organic phases were combined, washed with saturated sodium chloride solution (15 mL), dried over anhydrous sodium sulfate, and filtered. The filtrate was concentrated under reduced pressure to give the title compound 14b (0.85 g, 81% yield).

Step 3

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl)-N-(1-(3-fluoropro-pyl)azetidin-3-yl)pyridin amine 14c Compound 14b (0.82 g, 1.22 mmol) was dissolved in N,N-dimethylformamide (10 mL), and diisopropylethylam-ine (0.48 mg, 3.68 mmol) was added, followed by the dropwise addition of 1-fluoro-3-iodopropane (0.35 mg, 1.84 mmol). The reaction mixture was stirred for 12 h. Water (15 mL) was added, followed by the extraction with ethyl acetate (15 mL×3). The organic phases were combined, washed with water (15 mL×2) and saturated sodium chloride solution (15 mL), dried over anhydrous sodium sulfate, and filtered. The filtrate was concentrated under reduced pressure, and the resulting residue was purified by column chromatography with developing solvent system B to give the title compound 14c (0.7 g, 78% yield).

Step 4

2,2-Difluoro-3-((5S,7R)-5-(5-((1-(3-fluoropropyl)azetidin-3-yl)amino)pyridin-2-yl)-7-methyl-7,8-di-hydro-[1,3]dioxolo[4,5-g]isoquinolin-6(5H)-yl)pro-pan-1-ol 14

Compound 14c (200 mg, 0.4 mmol) was dissolved in tetrahydrofuran (25 mL), and a 1 M solution of n-tetrabuty-lammonium fluoride in tetrahydrofuran (2 mL) was added dropwise in an ice bath. After addition, the reaction mixture was stirred at room temperature for 1.5 h and concentrated under reduced pressure. Saturated sodium bicarbonate solution (10 mL) was added, followed by the extraction with ethyl acetate (10 mL×3). The organic phases were combined, washed with saturated sodium chloride solution (10 mL), dried over anhydrous sodium sulfate, and filtered. The filtrate was concentrated under reduced pressure, and the resulting residue was purified by column chromatography with developing solvent system B to give the title compound 14 (50 mg, 25% yield).

MS m/z (ESI): 493.2 [M+1].

$^1$H NMR (400 MHz, CD$_3$OD) 7.80 (d, 1H), 7.05 (d, 1H), 6.93 (dd, 1H), 6.61 (s, 1H), 6.20 (s, 1H), 5.85 (d, 2H), 4.77 (s, 1H), 4.54-4.52 (m, 1H), 4.45-4.43 (m, 1H), 4.15-4.12 (m, 1H), 3.88-3.85 (m, 2H), 3.76-3.57 (m, 3H), 3.14-3.05 (m, 4H), 2.75-2.69 (m, 3H), 2.57-2.53 (m, 1H), 1.84-1.76 (m, 2H), 1.06 (d, 3H).

Example 15
(5S,7R)-5-(2,6-difluoro-4-(((S)-1-(3-fluoropropyl)pyrrolidin-3-yl)oxy)phenyl)-7-methyl (2,2,2-trifluoroethyl)-5,6,7,8-tetrahydro-[1,3]dioxolo[4,5-g]isoquinoline 15
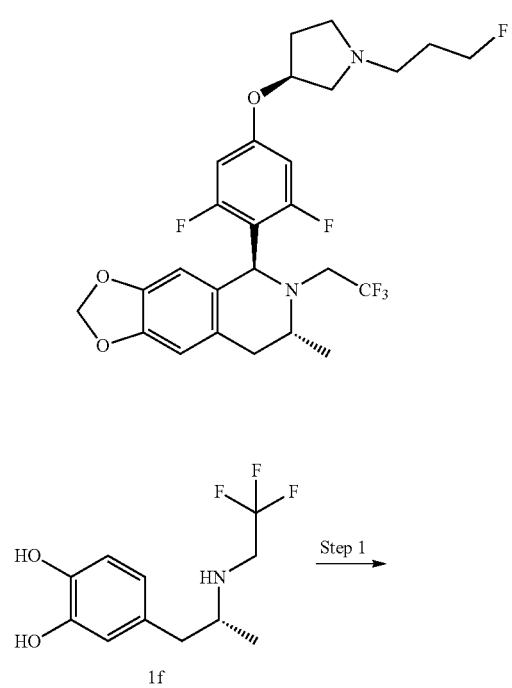
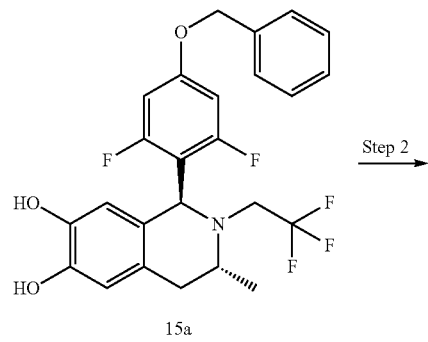
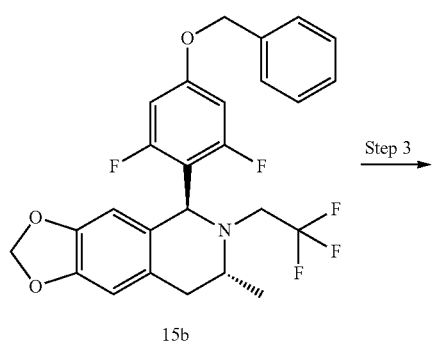
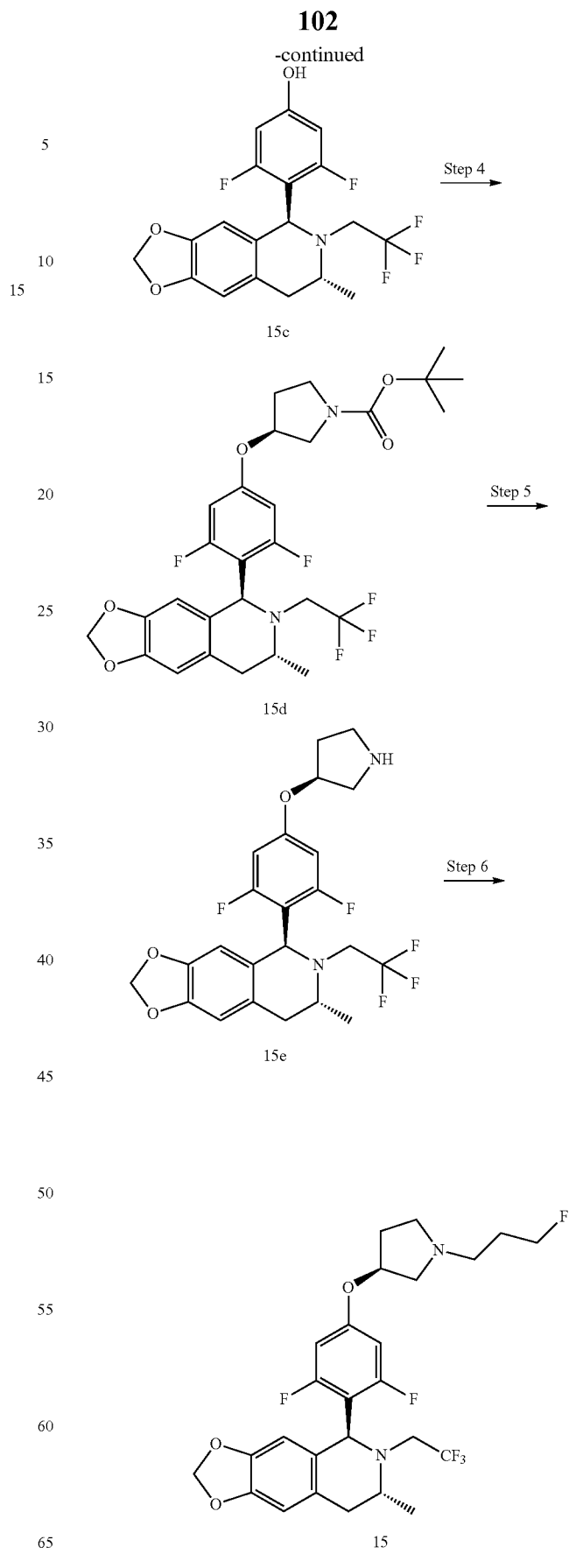

Step 1

(1S,3R)-1-(4-(benzyloxy)-2,6-difluorophenyl)-3-methyl-2-(2,2,2-trifluoroethyl)-1,2,3,4-tetrahydroisoquinoline-6,7-diol 15a Compound 1f (167 mg, 0.7 mmol) was dissolved in toluene (100 mL), and trifluoroacetic acid (115 mg, 1.0 mmol) and 4-(benzyloxy)-2,6-difluorobenzaldehyde (250 mg, 1.0 mmol, prepared as disclosed in "Example 5 on page 61 of the specification of Patent Application WO2008080001") were added. The reaction mixture was stirred in an oil bath at 80° C. for 16 h, and the reaction was terminated. The reaction mixture was cooled and concentrated under reduced pressure. Water (100 mL) was added, and the aqueous phase was adjusted to about pH 8 by adding saturated sodium bicarbonate solution (200 mL) and extracted with ethyl acetate (100 mL×2). The organic phases were combined, dried over anhydrous sodium sulfate, and filtered. The filtrate was concentrated under reduced pressure, and the resulting residue was purified by column chromatography with developing solvent system B to give the title compound 15a (235 mg, 73% yield).

MS m/z (ESI): 480.1 [M+1].

Step 2

(5S,7R)-5-(4-(benzyloxy)-2,6-difluorophenyl)-7-methyl-6-(2,2,2-trifluoroethyl)-5,6,7,8-tetrahydro-[1,3]dioxolo[4,5-g]isoquinoline 15b Compound 15a (580 mg, 1.2 mmol) was dissolved in N,N-dimethylformamide (10 mL), and dibromomethane (421 g, 2.4 mmol) and cesium carbonate (1.2 g, 3.6 mmol) were added. The reaction mixture was stirred in an oil bath at 70° C. for 16 h, and the reaction was terminated. The reaction mixture was cooled and concentrated under reduced pressure. Water (10 mL) was added, followed by the extraction with ethyl acetate (100 mL×2). The organic phases were combined, dried over anhydrous sodium sulfate, and filtered. The filtrate was concentrated under reduced pressure, and the resulting residue was purified by column chromatography with developing solvent system B to give the title compound 15b (458 mg, 77% yield).

MS m/z (ESI): 492.1 [M+1].

Step 3

3,5-difluoro-4-((5S,7R)-7-methyl-6-(2,2,2-trifluoroethyl)-5,6,7,8-tetrahydro-[1,3]dioxolo[4,5-g]isoquinolin-5-yl)phenol 15c Compound 15b (450 mg, 0.9 mmol) was dissolved in methanol (10 mL), and palladium hydroxide on carbon (0.1 g) was added in an argon atmosphere. The reaction mixture was stirred under hydrogen balloon for 3 h, and filtered. The filtrate was concentrated under reduced pressure to give the title compound 15c (0.3 g, 93% yield).

MS m/z (ESI): 402.1 [M+1].

Step 4 tert-Butyl (S)-3-(3,5-difluoro-4-((5S,7R)-7-methyl-6-(2,2,2-trifluoroethyl)-5,6,7,8-tetrahydro-[1,3]dioxolo[4,5-g]isoquinolin-5-yl)phenoxy)pyrrolidine-1-carboxylate 15d tert-Butyl (R)-3-hydroxypyrrolidine-1-carboxylate (82 mg, 0.4 mmol) was dissolved in a dry tetrahydrofuran (5 mL) solution, and tri-n-butylphosphine (240 mg, 1.2 mmol) and azodicarboxylic acid dipiperidide compound (300 mg, 1.2 mmol) were successively added in an ice bath. After stirring for 1 h, compound 15c (159 mg, 0.4 mmol) was added. The reaction mixture was stirred in an argon atmosphere for another 3 h and filtered. The filtrate was concentrated under reduced pressure, and the resulting residue was purified by column chromatography with developing solvent system B to give the title compound 15d (153 mg, 67% yield).

MS m/z (ESI): 571.0 [M+1].

Step 5

(5S,7R)-5-(2,6-difluoro-4-(((S)-pyrrolidin-3-yl)oxy)phenyl)-7-methyl-6-(2,2,2-trifluoroethyl)-5,6,7,8-tetrahydro-[1,3]dioxolo[4,5-g]isoquinoline 15e Compound 15d (240 mg, 0.4 mmol) was dissolved in dichloromethane (5 mL), and a 5 M solution of hydrogen chloride in 1,4-dioxane (1 mL) was added dropwise in an ice bath. After addition, the reaction mixture was stirred at room temperature for 1.5 h and concentrated under reduced pressure. Saturated sodium bicarbonate solution (5 mL) was added, followed by the extraction with ethyl acetate (5 mL×3). The organic phases were combined, washed with saturated sodium chloride solution (5 mL), dried over anhydrous sodium sulfate, and filtered. The filtrate was concentrated under reduced pressure to give the title compound 15e (220 mg, 90% yield).

Step 6

(5S,7R)-5-(2,6-difluoro-4-(((S)-1-(3-fluoropropyl)pyrrolidin-3-yl)oxy)phenyl)-7-methyl-6-(2,2,2-trifluoroethyl)-5,6,7,8-tetrahydro-[1,3]dioxolo[4,5-g]isoquinoline 15

Compound 15e (200 mg, 0.4 mmol) was dissolved in N,N-dimethylformamide (5 mL), and diisopropylethylamine (44 mg, 0.4 mmol) was added, followed by the dropwise addition of 1-fluoro-3-iodopropane (160 mg, 0.9 mmol). The reaction mixture was stirred for 12 h. Water (5 mL) was added, followed by the extraction with ethyl acetate (5 mL×3). The organic phases were combined, washed with water (5 mL×2) and saturated sodium chloride solution (5 mL), dried over anhydrous sodium sulfate, and filtered. The filtrate was concentrated under reduced pressure, and the resulting residue was purified by column chromatography with developing solvent system B to give the title compound 15 (50 mg, 22% yield).

MS m/z (ESI): 531.1 [M+1].

$^1$H NMR (400 MHz, CD$_3$OD) 6.59 (s, 1H), 6.52-6.49 (m, 2H), 6.18 (s, 1H), 5.85 (d, 2H), 5.15 (s, 1H), 4.91-4.89 (m, 1H), 4.56-4.53 (m, 1H), 4.46-4.44 (m, 1H), 3.49-3.47 (m, 1H), 3.20-3.16 (m, 1H), 2.93-2.88 (m, 4H), 2.67-2.63 (m, 2H), 2.56-2.51 (m, 2H), 2.40-2.36 (m, 1H), 1.98-1.89 (m, 4H), 1.08 (d, 3H).

Example 16

1-(3-Fluoropropyl)-N-(4-((5R,7R)-7-methyl-6-(2,2,2-trifluoroethyl)-5,6,7,8-tetrahydro-[1,3]dioxolo[4,5-g]isoquinolin-5-yl)phenyl)azetidin-3-amine 16

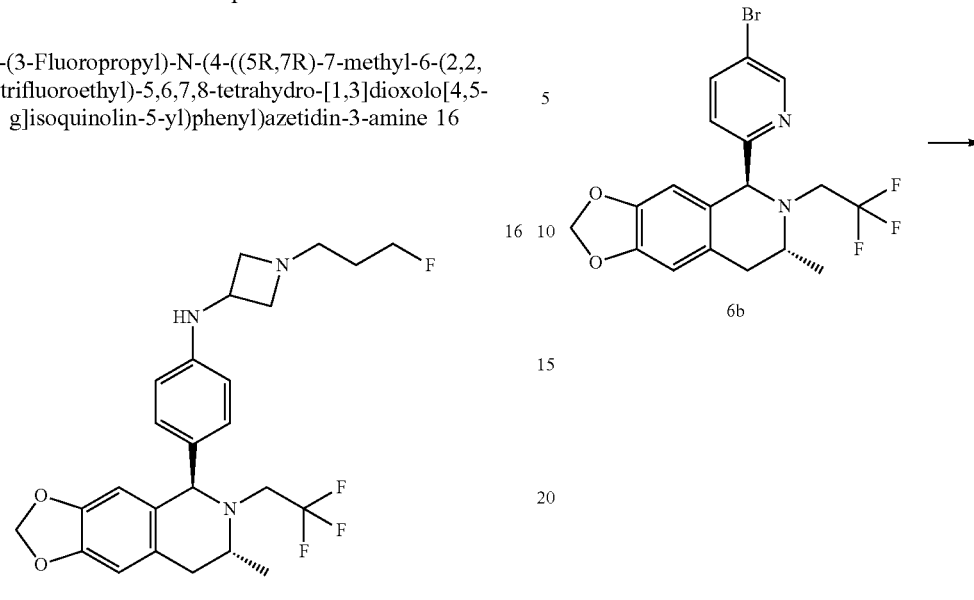

The title compound 16 (27 mg, 41% yield) was obtained by following the synthesis scheme of Example 1 with the compound 1c in step 7 replaced by 1-(3-fluoropropyl)azetidin-3-amine (prepared as disclosed in "Example 1 on page 50 of the specification of Patent Application WO2019228443").

MS m/z (ESI): 480.1 [M+1].

$^1$H NMR (400 MHz, CD$_3$OD) 7.04 (d, 2H), 6.64 (s, 1H), 6.61-6.52 (m, 2H), 6.31 (s, 1H), 5.87 (d, 2H), 4.69-4.61 (m, 2H), 4.53-4.39 (m, 3H), 4.18-4.16 (m, 1H), 3.94-3.90 (m, 1H), 3.48-3.37 (m, 4H), 3.10-3.05 (m, 1H), 2.87-2.82 (m, 1H), 2.61-2.56 (m, 1H), 2.07-1.96 (m, 3H), 1.09 (d, 3H).

Example 17

N-(1-(3-fluoropropyl)azetidin-3-yl)-6-((5S,7R)-7-methyl-6-(2,2,2-trifluoroethyl)-5,6,7,8-tetrahydro-[1,3]dioxolo[4,5-g]isoquinolin-5-yl)pyridin-3-amine 17

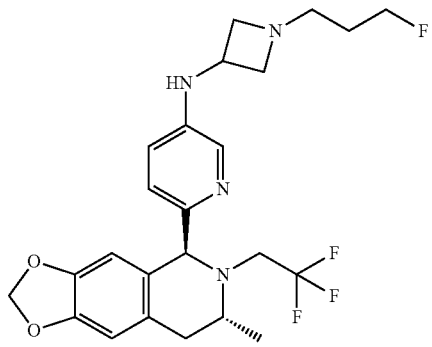

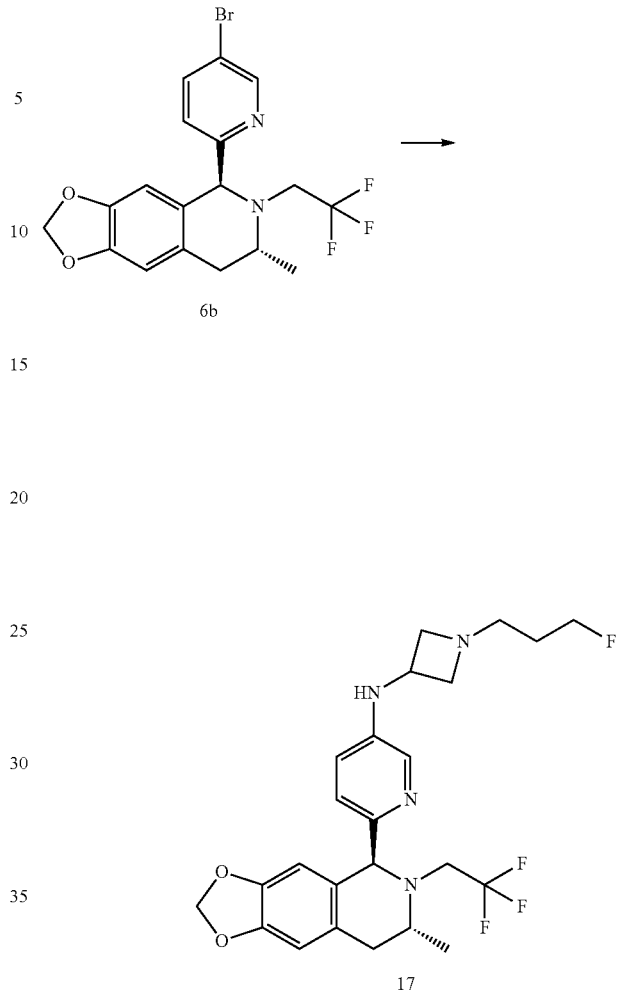

Compound 6b (100 mg, 0.2 mmol) was dissolved in dioxane (5 mL), and the compound 1-(3-fluoropropyl)azetidin-3-amine (47 mg, 0.4 mmol, prepared as disclosed in "Example 1 on page 50 of the specification of Patent Application WO2019228443"), 2-dicyclohexylphosphine-2',6'-bis(N,N-dimethylamino)-1,1'-biphenyl (3 mg, 0.007 mmol), tris(dibenzylideneacetone)dipalladium(0) (20 mg, 0.02 mmol) and sodium tert-butoxide (48 mg, 0.5 mmol) were added. The reaction mixture was stirred in an oil bath at 105° C. in an argon atmosphere for 16 h, and the reaction was terminated. The reaction mixture was cooled and concentrated. Saturated sodium bicarbonate solution (20 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 17 (25 mg, 22% yield).

MS m/z (ESI): 481.2 [M+1].

$^1$H NMR (400 MHz, CD$_3$OD) 7.78 (s, 1H), 7.14 (d, 1H), 6.98 (d, 1H), 6.60 (s, 1H), 6.20 (s, 1H), 5.83 (d, 2H), 4.76 (s, 1H), 4.54-4.52 (m, 1H), 4.44-4.42 (m, 1H), 4.13-4.09 (m, 1H), 3.84-3.81 (m, 2H), 3.47-3.45 (m, 1H), 3.30-2.90 (m, 4H), 2.71-2.53 (m, 4H), 1.82-1.74 (m, 2H), 1.08 (d, 3H).

Example 18

2,2-Difluoro-3-((5R,7R)-5-(4-((1-(3-fluoropropyl)azetidin-3-yl)amino)phenyl)-7-methyl-7,8-dihydro-[1,3]dioxolo[4,5-g]isoquinolin-6(5H)-yl)propan-1-ol

18

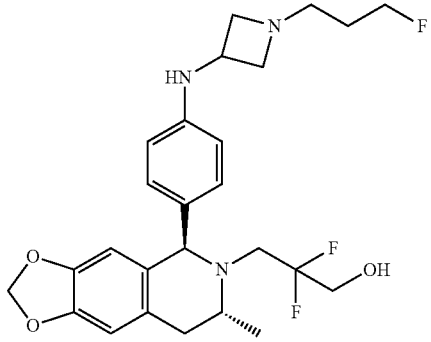

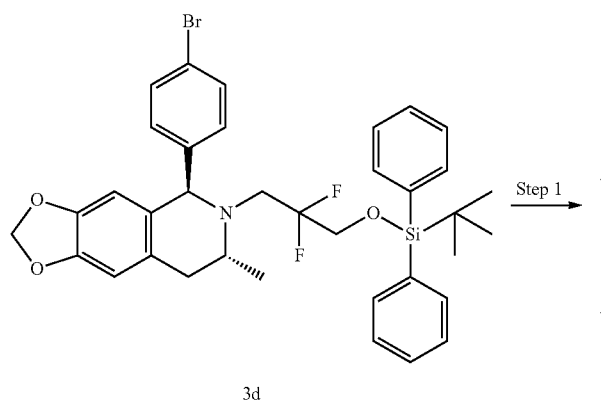

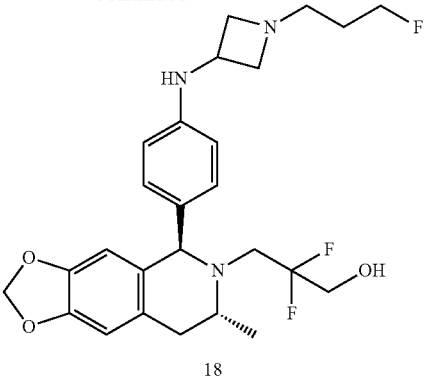

Step 1

3-((5R,7R)-5-(4-bromophenyl)-7-methyl-7,8-dihydro-[1,3]dioxolo[4,5-g]isoquinolin-6(5H)-yl)-2,2-difluoropropan-1-ol 18a Compound 3d (300 mg, 0.4 mmol) was dissolved in dichloromethane (10 mL), and a 1 M solution of n-tetrabutylammonium fluoride in tetrahydrofuran (2 mL) was added dropwise in an ice bath. After addition, the reaction mixture was stirred at room temperature for 1.5 h and concentrated under reduced pressure. Saturated sodium bicarbonate solution (10 mL) was added, followed by the extraction with ethyl acetate (10 mL×3). The organic phases were combined, washed with saturated sodium chloride solution (10 mL), dried over anhydrous sodium sulfate, and filtered. The filtrate was concentrated under reduced pressure, and the resulting residue was purified by column chromatography with developing solvent system B to give the title compound 18a (84 mg, 43% yield).

Step 2

2,2-Difluoro-3-((5R,7R)-5-(4-((1-(3-fluoropropyl)azetidin-3-yl)amino)phenyl)-7-methyl-7,8-dihydro-[1,3]dioxolo[4,5-g]isoquinolin-6(5H)-yl)propan-1-ol 18

Compound 18a (150 mg, 0.34 mmol) was dissolved in dioxane (5 mL), and the compound 1-(3-fluoropropyl)azetidin-3-amine (90 mg, 0.68 mmol, prepared as disclosed in "Example 1 on page 50 of the specification of Patent Application WO2019228443"), 4,5-bis(diphenylphosphino)-9,9-dimethylxanthene (20 mg, 0.03 mmol), palladium acetate (4 mg, 0.02 mmol) and cesium carbonate (222 mg, 0.68 mmol) were added. The reaction mixture was stirred in an oil bath at 105° C. in an argon atmosphere for 16 h, and the reaction was terminated. The reaction mixture was cooled and concentrated. Saturated sodium bicarbonate solution (20 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 18 (25 mg, 15% yield).

MS m/z (ESI): 492.2 [M+1].

$^1$H NMR (400 MHz, CD$_3$OD) 6.95 (d, 2H), 6.61 (s, 1H), 6.50 (d, 2H), 6.28 (s, 1H), 5.87 (d, 2H), 4.78 (s, 1H),

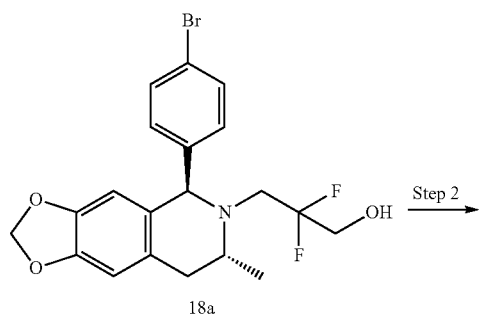

4.52-4.51 (m, 1H), 4.44-4.42 (m, 1H), 4.10-4.09 (m, 1H), 3.86-3.78 (m, 3H), 3.71-3.66 (m, 1H), 3.29-3.28 (m, 1H), 3.11-2.98 (m, 3H), 2.75-2.67 (m, 4H), 2.54-2.49 (m, 1H), 1.82-1.74 (m, 2H), 1.04 (d, 3H).

Example 19

2,2-Difluoro-3-((5R,7R)-5-(4-(((S)-1-(3-fluoropropyl)pyrrolidin-3-yl)amino)phenyl)-7-methyl-7,8-dihydro-[1,3]dioxolo[4,5-g]isoquinolin-6(5H)-yl-2,2-th)propan-1-ol 19

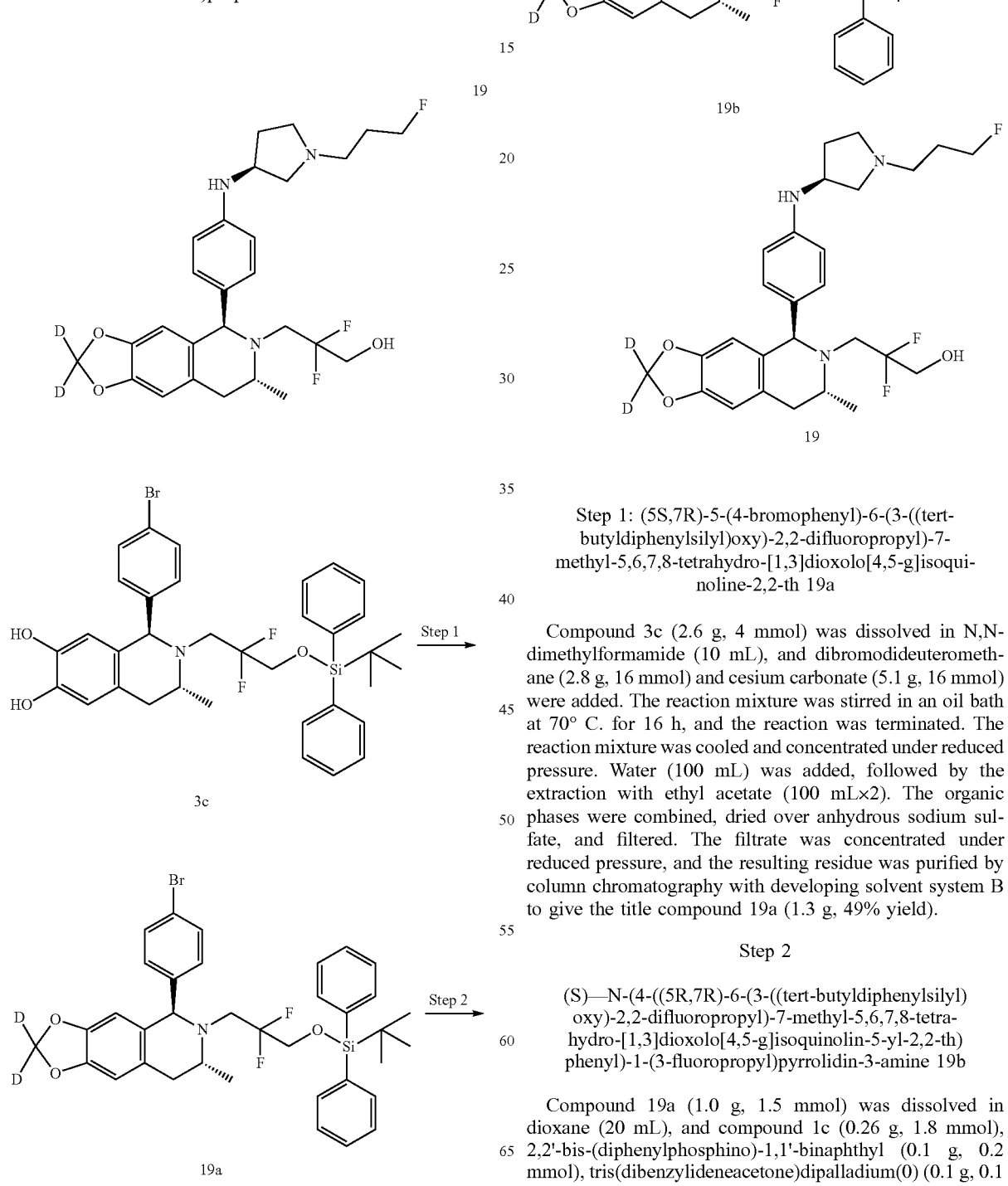

Step 1: (5S,7R)-5-(4-bromophenyl)-6-(3-((tert-butyldiphenylsilyl)oxy)-2,2-difluoropropyl)-7-methyl-5,6,7,8-tetrahydro-[1,3]dioxolo[4,5-g]isoquinoline-2,2-th 19a Compound 3c (2.6 g, 4 mmol) was dissolved in N,N-dimethylformamide (10 mL), and dibromodideuteromethane (2.8 g, 16 mmol) and cesium carbonate (5.1 g, 16 mmol) were added. The reaction mixture was stirred in an oil bath at 70° C. for 16 h, and the reaction was terminated. The reaction mixture was cooled and concentrated under reduced pressure. Water (100 mL) was added, followed by the extraction with ethyl acetate (100 mL×2). The organic phases were combined, dried over anhydrous sodium sulfate, and filtered. The filtrate was concentrated under reduced pressure, and the resulting residue was purified by column chromatography with developing solvent system B to give the title compound 19a (1.3 g, 49% yield).

Step 2

(S)—N-(4-((5R,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl-2,2-th)phenyl)-1-(3-fluoropropyl)pyrrolidin-3-amine 19b Compound 19a (1.0 g, 1.5 mmol) was dissolved in dioxane (20 mL), and compound 1c (0.26 g, 1.8 mmol), 2,2'-bis-(diphenylphosphino)-1,1'-binaphthyl (0.1 g, 0.2 mmol), tris(dibenzylideneacetone)dipalladium(0) (0.1 g, 0.1 mmol) and sodium tert-butoxide (0.3 g, 3.0 mmol) were added. The reaction mixture was stirred in an oil bath at 80° C. in an argon atmosphere for 16 h, and the reaction was terminated. The reaction mixture was cooled and concentrated. Saturated sodium bicarbonate solution (20 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 19b (0.6 g, 52% yield).

Step 3

2,2-Difluoro-3-((5R,7R)-5-(4-(((S)-1-(3-fluoropropyl)pyrrolidin-3-yl)amino)phenyl)-7-methyl-7,8-dihydro-[1,3]dioxolo[4,5-g]isoquinolin-6(5H)-yl-2,2-th)propan-1-ol 19

Compound 19b (0.3 g, 0.4 mmol) was dissolved in dichloromethane (5 mL), and a 1 M solution of n-tetrabutylammonium fluoride in tetrahydrofuran (2 mL) was added dropwise in an ice bath. After addition, the reaction mixture was stirred at room temperature for 1.5 h and concentrated under reduced pressure. Saturated sodium bicarbonate solution (10 mL) was added, followed by the extraction with ethyl acetate (10 mL×3). The organic phases were combined, washed with saturated sodium chloride solution (20 mL), dried over anhydrous sodium sulfate, and filtered. The filtrate was concentrated under reduced pressure, and the resulting residue was purified by column chromatography with developing solvent system B to give the title compound 19 (63 mg, 31% yield).

MS m/z (ESI): 508.0 [M+1].

$^1$H NMR (400 MHz, CD$_3$OD) 6.95 (d, 2H), 6.61 (s, 1H), 6.56 (d, 2H), 6.29 (s, 1H), 4.78 (s, 1H), 4.56-4.54 (m, 1H), 4.47-4.44 (m, 1H), 4.05-4.01 (m, 1H), 3.86-3.64 (m, 3H), 3.11-2.96 (m, 2H), 2.84-2.53 (m, 8H), 2.37-2.32 (m, 1H), 1.99-1.90 (m, 2H), 1.77-1.72 (m, 1H), 1.04 (d, 3H).

Example 20 (Comparative Example)

(7R,9S)-8-(2,2-difluoro-3-hydroxypropyl)-9-(5-((1-(3-fluoropropyl)azetidin yl)amino)pyridin-2-yl)-7-methyl-6,7,8,9-tetrahydro-1H-pyrrolo[3,4-h]isoquinoline-1,3(2H)-dione 20

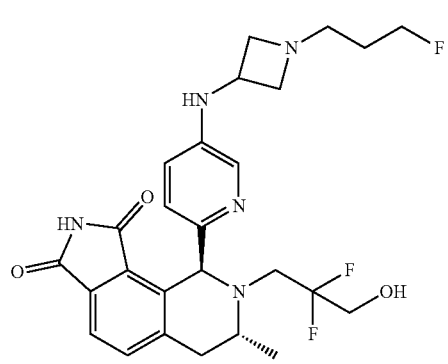

20

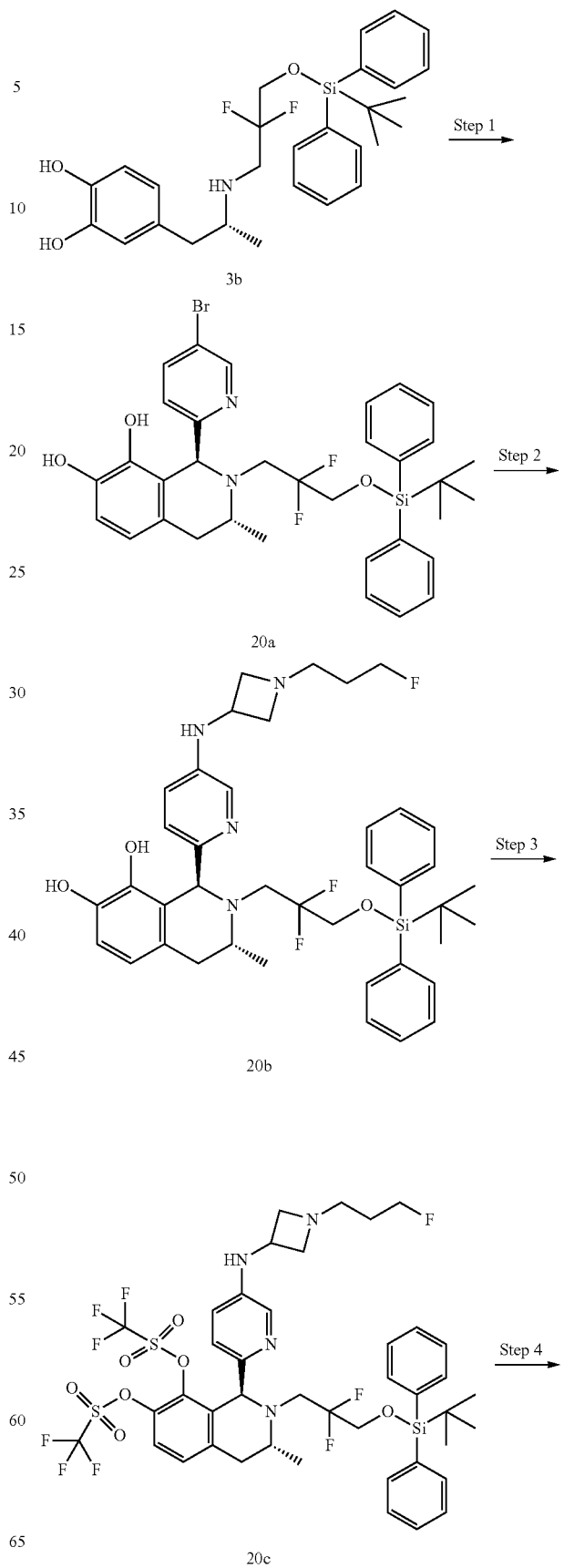

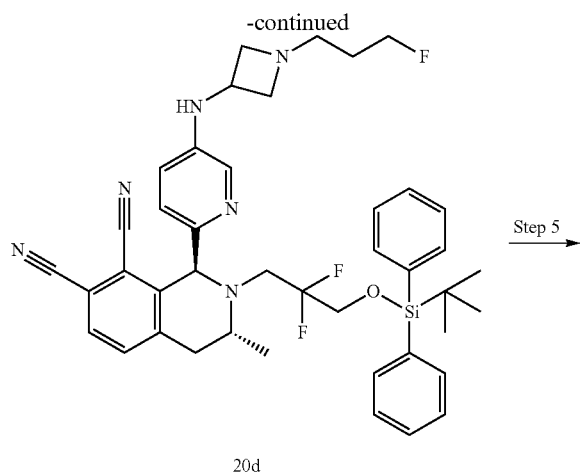

20d

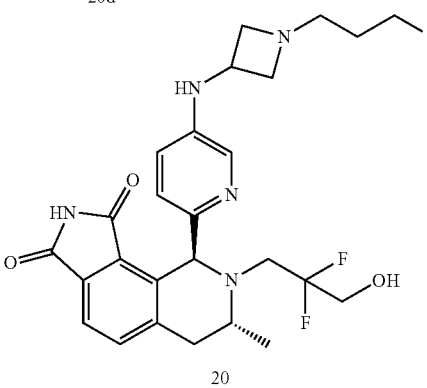

20

Step 1

(1S,3R)-1-(5-bromopyridin-2-yl)-2-(3-((tert-butyldiphenylsilyl)oxy)-2,2-difluoropropyl)-3-methyl-1,2,3,4-tetrahydroisoquinoline-7,8-diol 20a Compound 3b (0.8 g, 1.6 mmol) was dissolved in toluene (10 mL), and acetic acid (0.2 g, 3.2 mmol) and 5-bromopyridylaldehyde (0.6 g, 3.2 mmol) were added. The reaction mixture was stirred in an oil bath at 80° C. for 16 h, and the reaction was terminated. The reaction mixture was cooled and concentrated under reduced pressure. Water (20 mL) was added, and the reaction mixture was adjusted to about pH 8 by slowly adding saturated sodium bicarbonate solution (20 mL) and extracted with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 20a (0.3 g, 28% yield).

Step 2

(1S,3R)-2-(3-((tert-butyldiphenylsilyl)oxy)-2,2-difluoropropyl)-1-(5-((1-(3-fluoropropyl)azetidin-3-yl)amino)pyridin-2-yl)-3-methyl-1,2,3,4-tetrahydroisoquinoline-7,8-diol 20b Compound 20a (300 mg, 0.28 mmol) was dissolved in dioxane (10 mL), and 1-(3-fluoropropyl)azetidin-3-amine (111 mg, 0.84 mmol), 2-dicyclohexylphosphine-2',6'-bis(N,N-dimethylamino)-1,1'-biphenyl (15 mg, 0.04 mmol), tris(dibenzylideneacetone)dipalladium(0) (56 mg, 0.06 mmol) and sodium tert-butoxide (269 mg, 2.8 mmol) were added. The reaction mixture was stirred in an oil bath at 105° C. in an argon atmosphere for 16 h, and the reaction was terminated. The reaction mixture was cooled and concentrated under reduced pressure. Saturated sodium bicarbonate solution (20 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 20b (109 mg, 54% yield).

Step 3

(1S,3R)-2-(3-((tert-butyldiphenylsilyl)oxy)-2,2-difluoropropyl)-1-(5-((1-(3-fluoropropyl)azetidin-3-yl)amino)pyridin-2-yl)-3-methyl-1,2,3,4-tetrahydroisoquinoline-7,8-diyl bis(trifluoromethylsulfonate) 20c Compound 20b (400 mg, 0.56 mmol) was dissolved in dichloromethane (25 mL), and triethylamine (170 mg, 1.68 mmol), N,N-dimethylpyridin-4-amine (7 mg, 0.06 mmol) and N-phenylbis(trifluoromethylsulfonimide) (500 mg, 1.40 mmol) were added. The reaction mixture was allowed to react at room temperature for 3 h, and the reaction was terminated. The reaction mixture was cooled and concentrated under reduced pressure. Saturated sodium bicarbonate solution (20 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 20c (450 mg, 82% yield).

Step 4

(1S,3R)-2-(3-((tert-butyldiphenylsilyl)oxy)-2,2-difluoropropyl)-1-(5-((1-(3-fluoropropyl)azetidin-3-yl)amino)pyridin-2-yl)-3-methyl-1,2,3,4-tetrahydroisoquinoline-7,8-dinitrile 20d Compound 20c (30 mg, 0.03 mmol) was dissolved in N,N-dimethylformamide (5 mL), and zinc cyanide (11 mg, 0.1 mmol), tris(dibenzylideneacetone)dipalladium(0) (3 mg, 0.003 mmol) and 1,1'-bis(diphenylphosphino)ferrocene (2 mg, 0.004 mmol) were added. The reaction mixture was stirred in an oil bath at 100° C. in an argon atmosphere for 3 h, and the reaction was terminated. The reaction mixture was cooled and concentrated under reduced pressure. Saturated sodium bicarbonate solution (20 mL) was added, followed by the extraction with ethyl acetate (50 mL×2). The organic phases were combined, dried over anhydrous sodium sulfate, and filtered. The filtrate was concentrated under reduced pressure, and the resulting residue was purified by column chromatography with developing solvent system B to give the title compound 20d (16 mg, 72% yield).
MS m/z (ESI): 737.3 [M+1].

Step 5

(7R,9S)-8-(2,2-difluoro-3-hydroxypropyl)-9-(5-((1-(3-fluoropropyl)azetidin-3-yl)amino)pyridin-2-yl)-7-methyl-6,7,8,9-tetrahydro-1H-pyrrolo[3,4-h]isoquinoline-1,3(2H)-dione 20

Compound 20d (16 mg, 0.02 mmol) was dissolved in sulfuric acid (30 mg, 0.3 mmol). The solution was stirred in an oil bath at 90° C. for 2 h, and the reaction was terminated. The reaction mixture was cooled and concentrated under reduced pressure. Saturated sodium bicarbonate solution (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 20 (3 mg, 29% yield).

MS m/z (ESI): 518.2 [M+1].

$^1$H NMR (400 MHz, CD$_3$OD) 7.67 (d, 1H), 7.62 (d, 1H), 7.57 (d, 1H), 7.28 (d, 1H), 6.96 (dd, 1H), 5.93 (s, 1H), 4.53-4.51 (m, 1H), 4.43-4.41 (m, 1H), 4.10-4.05 (m, 1H), 3.94-3.88 (m, 2H), 3.81-3.78 (m, 2H), 3.30-3.26 (m, 2H), 2.98-2.95 (m, 2H), 2.81-2.63 (m, 5H), 1.83-1.77 (m, 2H), 1.13 (d, 3H).

Example 21 (Comparative Example)

(8R,10S)-9-(2,2-difluoro-3-hydroxypropyl)-10-(5-((1-(3-fluoropropyl)azetidin-3-yl)amino)pyridin-2-yl)-8-methyl-2,3,7,8,9,10-hexahydropyrrolophthalazine-1,4-dione 21

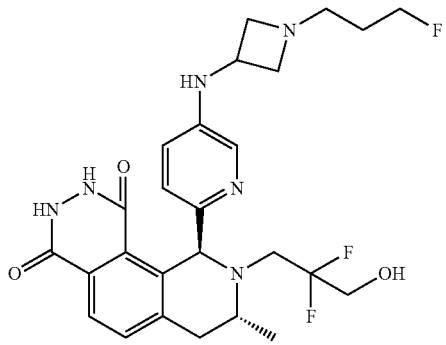

Compound 20 (6 mg, 0.01 mmol) was dissolved in ethanol (5 mL), and hydrazine hydrate (5 mg, 0.1 mmol) was added. The reaction mixture was stirred in an oil bath at 80° C. for 24 h, and the reaction was terminated. The reaction mixture was cooled and concentrated under reduced pressure. Saturated sodium bicarbonate solution (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 21 (3 mg, 49% yield).

MS m/z (ESI): 533.2 [M+1].

$^1$H NMR (400 MHz, CD$_3$OD) 8.08 (d, 1H), 7.71 (d, 1H), 7.55 (d, 1H), 7.27 (d, 1H), 6.97 (dd, 1H), 6.65 (s, 1H), 4.55-4.53 (m, 1H), 4.45-4.43 (m, 1H), 4.18-4.11 (m, 1H), 3.97-3.91 (m, 4H), 3.29-3.15 (m, 4H), 2.87-2.81 (m, 4H), 2.71-2.63 (m, 1H), 1.86-1.78 (m, 2H), 1.11 (d, 3H).

Biological Evaluation

The present disclosure is further described and explained below with reference to test examples, but these examples are not intended to limit the scope of the present disclosure.

Test Example 1. Inhibition of Binding of E to ER by Compounds Disclosed Herein

The compounds of the present disclosure can inhibit the binding of E (estrogen) to ER (estrogen receptor), thereby blocking the binding of the complex of E and ER to ERE (estrogen response element), and consequently the expression of downstream luciferase proteins. The inhibitory effects of the compounds of the present disclosure on the binding of E to ER was tested by using the following method.

1. Objective

This experiment is intended to test the inhibitory effects of the compounds on the binding of E to ER, and to evaluate the in vitro activity of the compounds according to the IC$_{50}$ values.

2. Method

An ERE was cloned upstream of the luciferase gene, and MCF-7/ERE-luciferase monoclonal cells were selected by transfection of MCF-7 (TCHu74, National Collection of Authenticated Cell Cultures). The MCF-7/ERE-luciferase cells were seeded into a 96-well plate with an MEM (hyclone, SH30024.01B) medium containing 10% charcoal stripped FBS (Moregate, FBSF), 1% sodium pyruvate (sigma, S8636), 1% non-essential amino acids (sigma, M7145) and 500 µg/mL G418 at a density of 30,000 cells/well and cultured at 37° C. with 5% CO$_2$. 20 mM stock solutions of the drugs are prepared, serially diluted 10-fold with 100% DMSO, and then diluted 20-fold with the medium. After the cells were cultured for 24 h, the medium was removed. 0.1 nM estradiol (sigma, E2758) and 10 µL of a medium-diluted drug were added to each well, and DMSO was added to the control group. The mixtures were well mixed by gentle shaking. The cells were cultured in an incubator at 37° C. with 5% CO$_2$ for 24 h, and then the cell culture liquid was removed, followed by the addition of 50 µL of a luciferase substrate (Promega, E6110) to each well. The plate was let stand at room temperature in the dark for 10-15 min, and the chemiluminescence signal values were determined.

3. Results

The inhibitory effects of the compounds of the present disclosure on the binding of E to ER were tested through the above experiment. The chemiluminescence signal value was plotted against the compound concentration (in log form) using Graphpad Prism, and the IC$_{50}$ values of the compounds were obtained. The results are shown in Table 1.

TABLE 1

| Inhibitory effects of the compounds disclosed herein on the binding of E to ER | |
|---|---|
| Example | IC$_{50}$ (nM) |
| 1 | 0.14 |
| 2 | 0.10 |
| 3 | 0.44 |
| 4 | 0.37 |
| 5 | 0.05 |
| 6 | 0.27 |
| 9 | 0.46 |
| 11 | 0.35 |

TABLE 1-continued

Inhibitory effects of the compounds disclosed
herein on the binding of E to ER

| Example | IC$_{50}$ (nM) |
| --- | --- |
| 12 | 1.13 |
| 13 | 0.69 |
| 14 | 0.5 |
| 15 | 0.19 |
| 16 | 0.27 |
| 17 | 0.43 |
| 18 | 0.07 |
| 19 | 0.07 |

Conclusion: The compounds claimed by the present disclosure had significant inhibitory effects on the binding of E to ER.

Test Example 2. Inhibitory Effects of Compounds Disclosed Herein on Proliferation of MCF-7 Cells

1. Objective

This experiment was intended to test the inhibitory effects of the compounds disclosed herein on the proliferation of MCF-7 Cells by using the ATP method, and to evaluate the in vitro activity of the compounds according to the IC$_{50}$ values.

2. Method

MCF-7 cells (TCHu74, National Collection of Authenticated Cell Cultures) were seeded into a 96-well plate with an MEM (hyclone, SH30024.01B) medium containing 10% FBS (Gibco, 10099-141), 1% sodium pyruvate (sigma, 58636) and 1% non-essential amino acid (sigma, M7145) at a density of 4,000 cells/well and cultured at 37° C. with 5% CO$_2$. 20 mM stock solutions of the compounds are prepared, serially diluted with 100% DMSO to a final concentration of 1000×, and then diluted 20-fold with a medium containing 2% FBS. After the cells were cultured for 24 h, the medium was removed. 90 µL of the medium containing 2% FBS and 10 µL of a drug were added to each well, and 10 µL of DMSO was added to the control group. The mixtures were well mixed by gentle shaking. The blank group contained only 100 µL of the medium containing 2% FBS. The cells were cultured in an incubator at 37° C. with 5% CO$_2$ for 72 h, and then 50 µL of mixed Cell Titer-Glo (Promega, G7571) was added to each well. The mixtures were well mixed by shaking and let stand at room temperature for 10 min, and the chemiluminescence signal values were determined.

3. Data Analysis

The chemiluminescence signal value was plotted against the compound concentration (in log form) using Graphpad Prism, and the IC$_{50}$ values of the compounds were obtained. The results are shown in Table 2.

TABLE 2

Inhibitory effects of the compounds disclosed
herein on proliferation of MCF-7 cells

| Example | IC$_{50}$ (nM) |
| --- | --- |
| 1 | 0.31 |
| 2 | 0.17 |
| 3 | 0.15 |
| 4 | 0.28 |
| 5 | 0.03 |
| 6 | 0.34 |
| 9 | 0.35 |
| 11 | 0.23 |
| 12 | 1.12 |
| 13 | 0.29 |
| 14 | 0.36 |
| 15 | 0.3 |
| 17 | 0.44 |
| 18 | 0.07 |
| 19 | 0.07 |
| 20 | >10000 |
| 21 | >10000 |

Note: Examples 20 and 21 are comparative examples.

Conclusion: The compounds claimed by the present disclosure had significant inhibitory effects on the proliferation of MCF-7 cells, and Comparative Examples 20 and 21 showed no activity.

Test Example 3. Biological Evaluation of Inhibition of Proliferation of ERα Mutant-Expressing MCF7 Cells by Compounds Disclosed Herein

1. Objective

This experiment was intended to test the inhibitory activity of the compounds disclosed herein against the proliferation of ERα mutant-expressing MCF7 cells.

2. Method

Site-Directed Mutagenesis and Cell Line Construction

The mutant estrogen receptor α (ERα) Y537S of human ERα protein was obtained by site-directed mutagenesis in a two-primer PCR manner using the cDNA of wild-type ESR1 gene (Accession No. NM000125) as a template. The sequences of the primers used in the mutation are as follows (the underlined nucleotides are the sites of mutation): Y537S: F-AAG AAC GTG GTG CCC CTC TCT GAC CTG CTG CTG GAG ATG (SEQ ID NO: 1); R-CAT CTC CAG CAG CAG GTC AGA GAG GGG CAC CAC GTT CTT (SEQ ID NO: 2). The cDNA of the mutant ESR1 was cloned into the lentiviral vector of interest pCDH-CMV-MCS-EF1-Puro. The lentiviral plasmid bearing the mutant ESR1 gene sequence and the lentiviral packaging plasmid were then transfected into HEK-293T cells (ATCC, CRL-3216) by using Lipofectamine 3000 Transfection Reagent (ThermoFisher Scientific, Cat #L3000075). Forty-eight hours after transfection, the virus-bearing medium supernatant was filtered and ultracentrifuged to obtain a virus precipitate, which was then resuspended in an appropriate amount of medium. The suspension was added to MCF7 cells (ATCC, HTB-22), followed by the addition of polybrene at a final concentration of 8 µg/mL. The mixture was incubated overnight. Two days after transfection, 1 µg/mL puromycin was added to the cell culture liquid for resistance screening. About two weeks later, an MCF7 cell line capable of stably expressing the ERαY537S mutant was obtained.

Cell Proliferation Inhibition Assay

The ERα mutant-expressing MCF7 cells were cultured in an MEM (GE Healthcare, SH30024.01) complete medium containing 10% fetal bovine serum. On the first day of the experiment, the cells were seeded into a 96-well plate with complete medium at a density of 3,000 cells/well to form 100 μL of cell suspension per well. The plate was incubated overnight in a cell incubator at 37° C. with 5% $CO_2$. The following day the medium was removed, and 135 μL of an MEM incomplete medium containing 2% fetal bovine serum, and 15 μL of a test compound prepared at different concentrations with the incomplete medium were added to each well. The final concentrations of the compound were 9 concentration points obtained by 4-fold serial dilution from 100 nM. A blank control containing 0.5% DMSO was set. The plate was incubated in a cell incubator at 37° C. with 5% $CO_2$ for 144 h. On day 8, the 96-well cell culture plate was taken out. 150 μL of CellTiter-Glo® Luminescent Cell Viability Assay (Promega, G7573) was added to each well. The plate was let stand at room temperature for 10 min, and the luminescence signal values was read using a multilabel microplate reader (PerkinElmer, VICTOR 3). The $IC_{50}$ values for the inhibitory activity of the compounds were calculated according to the compound concentrations and the luminescence signal values and are shown in Table 3.

3. Results

TABLE 3

$IC_{50}$ values for the inhibitory effects of the compounds disclosed herein on the proliferation of ERα mutant-expressing MCF7 cells

| Example | $IC_{50}$ (nM) |
|---|---|
| 1 | 1.38 |
| 2 | 0.78 |
| 3 | 0.43 |
| 4 | 0.89 |
| 5 | 0.07 |
| 6 | 0.82 |
| 9 | 1.35 |
| 11 | 0.71 |
| 12 | 3.49 |
| 13 | 1.36 |
| 14 | 1.27 |
| 15 | 0.68 |
| 17 | 2.19 |
| 18 | 0.25 |
| 19 | 0.43 |

Conclusion: The compounds claimed by the present disclosure had significant inhibitory effects on the proliferation of ERα mutant-expressing MCF7 cells.

Test Example 4. Degradation of ERα by Compounds Disclosed Herein

1. Objective

This experiment was intended to test the degradation of ERα by the compounds disclosed herein. This method was used to test the degradation of ERα by the compounds disclosed herein.

2. Method

ERα-positive breast cancer cell line MCF-7 cells were cultured in a DMEM/F12 medium (HyClone, SH30023.01) containing 10% fetal bovine serum (Corning, 35-010-CV). On the first day of the experiment, after being digested, the cells were washed once with a phenol red-free DMEM/F12 medium (ThermoFisher, 11039-021) containing 5% charcoal stripped fetal bovine serum (BIOSUN, BS-0004-500), then resuspended, and counted, and the cell density was adjusted to $1.79 \times 10^5$ cells/mL. 280 μL of the cell suspension was added to each well of a 48-well plate (Corning, 3548), and the cells were cultured overnight in an incubator at 37° C. with 5% $CO_2$. The following day the compounds were serially diluted with DMSO and further diluted with the phenol red-free DMEM/F12 medium containing 5% charcoal-stripped fetal bovine serum. 20 μL of a diluted compound was added to each well of the 48-well plate at final concentrations of 3000, 300, 30, 3, 0.3, 0.03 and 0.003 nM. The 48-well plate was placed in the incubator for 16 to 18 h. A 96-well plate was coated with the capture antibody from the human ERα/NR3A1 total protein assay kit (R&D, DYC5715-5). 1 μg/mL capture antibody was prepared in PBS, and 100 μL of the antibody was added to each well of the 96-well plate (Corning, 3590). The plate was placed in an incubator at 26° C. overnight. On day 3, the antibody-coated 96-well plate was washed once with PBS, and 200 μL of PBS containing 1% BSA was added to each well. The plate was incubated in an incubator at 37° C. for 1.5 h to be blocked. The cell culture medium supernatant was discarded. The cells were washed once with PBS, and 60 μL of a cell lysis buffer was added to each well. The cell lysis buffer was PBS containing 6 M urea, 1 mM EDTA, 0.5% TritonX-100, 1 mM PMSF and a protease inhibitor (Roche, 04693159001). The cells were lysed on ice for 15 min, and 300 μL of PBS containing 1 mM EDTA and 0.5% TritonX-100 was added to each well to dilute the urea to 1 M. The blocking buffer in the blocked 96-well plate was discarded, and 100 μL of diluted cell lysis buffer was added to each well. The plate was incubated in an incubator at 37° C. for 2 h and washed 5 times with PBS. A biotinylated assay antibody was diluted to 0.4 μg/mL with PBS containing 1% BSA, and then 100 μL of the assay antibody was added to each well. The plate was incubated in an incubator at 37° C. for 1 h. The plate was then washed five more times, and 100 μL of avidin-HRP diluted 200-fold with PBS containing 1% BSA was added to each well. The plate was incubated at 37° C. for 30 min. The plate was washed five more times, and 100 μL of TMB substrate was added to each well. The plate was incubated at room temperature until blue color appeared, and 100 μL of stop solution was added to each well. OD450 signal values were read using a PHERAstar multi-mode microplate reader. The $IC_{50}$ values for the inhibitory activity of the compounds were calculated using Graphpad Prism software. The maximum degradation rates of the compounds are the ratios of the level of ERα remaining in the cells after the cells were treated with 3000 nM compounds to the level of ERα remaining in cells after the cells were treated with 3000 nM Fulvestrant.

3. Results

The $EC_{50}$ values determined for the compounds disclosed herein in the degradation of ERα are shown in Table 4.

TABLE 4

Degradation of ERα by the compounds disclosed herein

| Example | $EC_{50}$ (nM) | Emax degradation (%) |
|---|---|---|
| Fulvestrant | 0.06 | 100 |
| 1 | 0.32 | 94 |
| 2 | 0.24 | 104 |
| 3 | 0.19 | 129 |
| 4 | 0.21 | 115 |
| 5 | 0.04 | 108 |

TABLE 4-continued

Degradation of ERα by the compounds disclosed herein

| Example | EC$_{50}$ (nM) | Emax degradation (%) |
|---|---|---|
| 6 | 0.17 | 104 |
| 9 | 1.04 | 107 |
| 11 | 0.45 | 91 |
| 12 | 0.15 | 101 |
| 13 | 0.38 | 107 |
| 14 | 0.5 | 92 |
| 15 | 0.15 | 95 |
| 17 | 1.24 | 104 |
| 18 | 0.1 | 106 |
| 19 | 0.13 | 100 |
| 20 | >10000 | — |
| 21 | >10000 | — |

Note: Examples 20 and 21 are comparative examples.

Conclusion: The compounds claimed by the present disclosure significantly degraded ERα, and Comparative Examples 20 and 21 showed no activity.

Test Example 5. Inhibition of Enzymatic Activity of Site of Metabolism of Midazolam in Human Liver Microsome CYP3A4 by Compounds Disclosed Herein The inhibition of the enzymatic activity of the site of metabolism of midazolam in human liver microsome CYP3A4 by the compounds disclosed herein was tested by using the following method.

I. Materials and Instruments

1. Phosphate buffer (20×PBS, purchased from Sangon);
2. NADPH (ACROS, A2646-71-1);
3. Human liver microsome (Corning Gentest, Cat No. 452161, Lot No. 9050002, Donor, 36);
4. ABI QTrap 4000 LC-MS System (AB Sciex);
5. ZORBAX Extend-C18, 3×50 mm, 3.5 μm (Agilent, USA);
6. CYP probe substrate (midazolam, TRC, M343000/3 μM) and positive control inhibitor (ketoconazole, SIGMA, Cat No. K1003-100MG).

II. Procedures

A 100 mM PBS buffer was prepared. A 0.25 mg/mL microsome solution, a 7.5 mM MgCl$_2$ and a 5 mM NADPH solution were prepared using the buffer. A 30 mM stock solution was diluted with DMSO to obtain 30 mM, 10 mM, 3 mM, 1 mM, 0.3 mM, 0.03 mM, 0.003 mM and 0 mM serial solutions I, which were further diluted 200-fold with phosphate buffer (PBS) to obtain serial test solutions II (150, 50, 15, 5, 1.5, 0.15, 0.015 and 0 μM). A midazolam working solution was diluted with PBS to 15 μM.

40 μL of a 0.25 mg/mL microsome solution prepared in 7.5 mM MgCl$_2$ and 20 μL of each of the 15 μM midazolam working solution and the compound working solutions (150, 50, 15, 5, 1.5, 0.15, 0.015 and 0 μM) were measured out and well mixed. Ketoconazole at the same concentration was used in place of the compounds as a positive control group. The mixtures were pre-incubated with 5 mM NADPH solution at 37° C. for 5 min at the same time. After 5 minutes, 20 μL of NADPH was added to each well to start reactions. The mixtures were incubated for 30 min. Duplicate samples were set for all of the incubated samples. After 30 minutes, 250 μL of internal standard-containing acetonitrile was added to all the samples. The mixtures were well mixed, shaken at 800 rpm for 10 min, and then centrifuged at 3700 rpm for 10 min. 100 μL of the supernatant and 80 μL of ultrapure water were well mixed and subjected to LC-MS/MS analysis.

The IC$_{50}$ values of the drugs for the site of metabolism of midazolam in CYP3A4 were calculated using Graphpad Prism and are shown in Table 5.

TABLE 5

IC$_{50}$ values of the compounds disclosed herein for the site of metabolism of midazolam in human liver microsome CYP3A4

| Example | IC$_{50}$ (μM) |
|---|---|
| 1 | 15.76 |
| 2 | >30 |
| 3 | 10 |
| 12 | 8.18 |
| 13 | 15.38 |

Conclusion: The compounds claimed by the present disclosure had weak inhibitory effects on the site of metabolism of midazolam in human liver microsome CYP3A4, showing better safety, suggesting that metabolic drug interaction based on the site of metabolism of midazolam in CYP3A4 does not occur.

Test Example 6. Inhibition of Enzymatic Activity of Site of Metabolism of Testosterone in Human Liver Microsome CYP3A4 by Compounds Disclosed Herein The inhibition of the enzymatic activity of the site of metabolism of testosterone in human liver microsome CYP3A4 by the compounds disclosed herein was tested by using the following method.

I. Materials and Instruments

1. Phosphate buffer (20×PBS, purchased from Sangon);
2. NADPH (ACROS, A2646-71-1);
3. Human liver microsome (Corning Gentest, Cat No. 452161, Lot No. 905002, Donor36);
4. ABI QTrap 4000 LC-MS System (AB Sciex);
5. ZORBAX Extend-C18, 3×50 mm, 3.5 μm (Agilent, USA);
6. CYP probe substrate (testosterone, Vocko, CAS No. [58-22-0]/75 μM) and positive control inhibitor (ketoconazole, SIGMA, Cat No. K1003-100MG).

II. Procedures

A 100 mM PBS buffer was prepared. A 100 mM PBS buffer was prepared. A 0.25 mg/mL microsome solution, a 7.5 mM MgCl$_2$ and a 5 mM NADPH solution were prepared using the buffer. A 30 mM stock solution was diluted with DMSO to obtain 30 mM, 10 mM, 3 mM, 1 mM, 0.3 mM, 0.03 mM, 0.003 mM and 0 mM serial solutions I, which were further diluted 200-fold with phosphate buffer (PBS) to obtain serial test solutions II (150, 50, 15, 5, 1.5, 0.15, 0.015 and 0 μM). A testosterone working solution was diluted with PBS to 375 μm.

40 μL of a 0.25 mg/mL microsome solution prepared in 7.5 mM MgCl$_2$ and 20 μL of each of the 375 μM testosterone working solution and the compound working solutions (150, 50, 15, 5, 1.5, 0.15, 0.015 and 0 μM) were measured out and well mixed. Ketoconazole at the same concentration was used in place of the compounds as a positive control group. The mixtures were pre-incubated with 5 mM NADPH solution at 37° C. for 5 min at the same time. After 5 minutes, 20 μL of NADPH was added to each well to start reactions. The mixtures were incubated for 30 min. After 30 minutes, 250 μL of internal standard-containing acetonitrile was added to all the samples. The mixtures were well mixed, shaken at 800 rpm for 10 min, and then centrifuged at 3700 rpm for 10 min. 100 μL of the supernatant and 80 μL of ultrapure water were well mixed and subjected to LC-MS/MS analysis.

The $IC_{50}$ values of the drugs for the site of metabolism of testosterone in CYP3A4 were calculated using Graphpad Prism and are shown in Table 6.

TABLE 6

$IC_{50}$ values of the compounds disclosed herein for the site of metabolism of testosterone in human liver microsome CYP3A4

| Example | $IC_{50}$ (μM) |
| --- | --- |
| 1 | 7.31 |
| 2 | >30 |
| 3 | 14.57 |
| 4 | 15.50 |
| 12 | 23.77 |
| 13 | >30 |

Conclusion: The compounds claimed by the present disclosure had weak inhibitory effects on the site of metabolism of testosterone in human liver microsome CYP3A4, showing better safety.

Test Example 7. Time-Dependent Inhibition of Enzymatic Activity of Site of Metabolism of Midazolam in Human Liver Microsome CYP3A4 by Compounds Disclosed Herein The time-dependent inhibition of the CYP enzymatic activity of the site of metabolism of midazolam in human liver microsome CYP3A4 by the compounds disclosed herein was tested by using the following method.

I. Materials and Instruments

1. Phosphate buffer (20×PBS, purchased from Sangon);
2. NADPH (ACROS, A2646-71-1);
3. Human liver microsome (Corning Gentest, Cat No, 452161, Lot No. 9050002, Donor, 36);
4. ABI QTrap 4000 LC-MS System (AB Sciex);
5. ZORBAX Extend-C18, 3×50 mm, 3.5 μm (Agilent, USA);
6. CYP probe substrate (midazolam, TRC, M343000/3 μM) and positive control inhibitor (verapamil, Adamas Reagent Co, Ltd, Cat No. 25904A).

II. Procedures

A 100 mM PBS buffer was prepared. A 0.25 mg/mL microsome solution, a 7.5 mM $MgCl_2$ and a 5 mM NADPH solution were prepared using the buffer. A 30 mM stock solution was diluted with DMSO to obtain 30 mM, 10 mM, 3 mM, 1 mM, 0.3 mM, 0.1 mM, 0.03 mM and 0 mM serial solutions I, which were further diluted 200-fold with phosphate buffer (PBS) to obtain serial test solutions II (150, 50, 15, 5, 1.5, 0.5, 0.15 and 0 μM). A midazolam working solution was diluted with PBS to 15 μM.

The serial test solutions prepared above were well mixed by shaking and aliquoted in 20 μL portions into corresponding reaction plates (+NADPH, T0 and −NADPH groups were set). Three parallel tests were set. 40 μL of the liver microsome working solution was added to each 96-well plate. 20 μL of a corresponding substrate solution was added to the T0 plate. 20 μL of NADPH was added to the T0 plate and +NADPH group. A timer was started, and the plates were incubated in a water bath at 37° C. After 30 min of incubation, the T0 plate was taken out, and the reaction was terminated with 250 μL of an internal standard-containing ACN solution. The +NADPH group was supplemented with 20 μL of the corresponding substrate solution, and the −NADPH group was supplemented with 20 μL of the corresponding substrate solution and 20 μL of NADPH. A timer was started, and the plates were incubated in a water bath at 37° C. After 30 min of incubation, the plates were taken out, and the reactions were terminated with 250 μL of an internal standard-containing ACN solution. Then the plates were shaken on a shaker at 800 rpm for 10 min and centrifuged at 4000 rpm for 15 min. 100 μL of the supernatant and 80 μL of ultrapure water were well mixed and subjected to LC-MS/MS analysis.

The $IC_{50}$ values of the drugs for the site of metabolism of midazolam in CYP3A4 were calculated using Graphpad Prism and are shown in Table 7.

TABLE 7

$IC_{50}$ values and $IC_{50}$ shifts of the compounds disclosed herein for the site of metabolism of midazolam in human liver microsome CYP3A4

| Example | (+)NADPH $IC_{50}$ (μM) | (−)NADPH $IC_{50}$ (μM) | $IC_{50}$ Shift |
| --- | --- | --- | --- |
| 4 | 2.43 | 2.47 | 1.0 |
| 12 | 9.16 | 10.17 | 0.9 |
| 13 | 13.11 | 19.59 | 0.7 |

Conclusion: The compounds claimed by the present disclosure had weak inhibitory effects on the site of metabolism of midazolam in human liver microsome CYP3A4, showing better safety, suggesting that metabolic drug interaction based on the site of metabolism of midazolam in CYP3A4 does not occur.

Test Example 8. Time-Dependent Inhibition of Enzymatic Activity of Site of Metabolism of Testosterone in Human Liver Microsome CYP3A4 by Compounds Disclosed Herein The time-dependent inhibition of the enzymatic activity of the site of metabolism of testosterone in human liver microsome CYP3A4 by the compounds disclosed herein was tested by using the following method.

I. Materials and Instruments

1. Phosphate buffer (20×PBS, purchased from Sangon);
2. NADPH (ACROS, A2646-71-1);
3. Human liver microsome (Corning Gentest, Cat No, 452161, Lot No. 905002, Donor36);
4. ABI QTrap 4000 LC-MS System (AB Sciex);
5. ZORBAX Extend-C18, 3×50 mm, 3.5 μm (Agilent, USA);
6. CYP probe substrate (testosterone, Vocko, CAS No. [58-22-0]/75 μM) and positive control inhibitor (verapamil, Adamas Reagent Co Ltd, Cat No. 25904A).

II. Procedures

A 100 mM PBS buffer was prepared. A 0.25 mg/mL microsome solution, a 7.5 mM $MgCl_2$ and a 5 mM NADPH solution were prepared using the buffer. A 30 mM stock solution was diluted with DMSO to obtain 30 mM, 10 mM, 3 mM, 1 mM, 0.3 mM, 0.1 mM, 0.03 mM and 0 mM serial solutions I, which were further diluted 200-fold with phosphate buffer (PBS) to obtain serial test solutions II (150, 50, 15, 5, 1.5, 0.5, 0.15 and 0 μM). A midazolam working solution was diluted with PBS to 15 μM.

The serial test solutions prepared above were well mixed by shaking and aliquoted in 20 μL portions into corresponding reaction plates (+NADPH, T0 and −NADPH groups were set). Three parallel tests were set. 40 μL of the liver microsome working solution was added to each 96-well plate. 20 μL of a corresponding substrate solution was added to the T0 plate. 20 μL of NADPH was added to the T0 plate and +NADPH group. A timer was started, and the plates were incubated in a water bath at 37° C. After 30 min of incubation, the T0 plate was taken out, and the reaction was terminated with 250 μL of an internal standard-containing ACN solution. The +NADPH group was supplemented with 20 μL of the corresponding substrate solution, and the −NADPH group was supplemented with 20 μL of the corresponding substrate solution and 20 μL of NADPH. A timer was started, and the plates were incubated in a water bath at 37° C. After 30 min of incubation, the plates were taken out, and the reactions were terminated with 250 μL of an internal standard-containing ACN solution. Then the plates were shaken on a shaker at 800 rpm for 10 min and centrifuged at 4000 rpm for 15 min. 100 μL of the supernatant and 80 μL of ultrapure water were well mixed and subjected to LC-MS/MS analysis.

The $IC_{50}$ values of the drugs for the site of metabolism of testosterone in CYP3A4 were calculated using Graphpad Prism and are shown in Table 8.

TABLE 8

$IC_{50}$ values and $IC_{50}$ shifts of the compounds disclosed herein for the site of metabolism of testosterone in human liver microsome CYP3A4

| Example | (+)NADPH $IC_{50}$ (μM) | (−)NADPH $IC_{50}$ (μM) | $IC_{50}$ Shift |
|---|---|---|---|
| 4 | 2.4 | 2.5 | 1.0 |
| 12 | 11.6 | 25.2 | 0.5 |
| 13 | >30 | >30 | No TDI |

Conclusion: The compounds claimed by the present disclosure had weak inhibitory effects on the site of metabolism of testosterone in human liver microsome CYP3A4, showing better safety, suggesting that metabolic drug interaction based on CYP3A4 does not occur.

Test Example 9

1. Objective

The blocking of hERG potassium currents by the compounds disclosed herein was tested in a stable cell strain transfected with hERG potassium channels using automated patch clamp.

2. Method

2.1. Materials and Instruments

2.1.1. Materials:

| Reagent | Supplier | Cat. No. |
|---|---|---|
| FBS | GIBCO | 10099 |
| Sodium pyruvate solution | sigma | S8636-100ML |
| MEM non-essential amino acid solution (100×) | sigma | M7145-100ML |
| G418 sulfate | Enzo | ALX-380-013-G005 |
| MEM | Hyclone | SH30024.01B |
| hERG cDNA | Synthesized by GENEWIZ | Gene sequence NM_000238.4- |

2.1.2. Instruments:

| Instrument | Supplier | Model |
|---|---|---|
| Patchliner 4 channel | nanion | 2-03-03100-002 |
| Patchliner cleaning station | nanion | 2-02-03201-005 |
| Patchliner cell bank | nanion | 2-02-03105-000 |
| Elektrodenchloridierer Patchliner | nanion | 3-02-03533-000 |
| HEAK EPC10 patch clamp amplifier | nanion | 1-01-10012-000 |
| Osmometer | Gonoter | Gonoter 030 |
| pH meter | Mettle Toledo | FE20 |

2.2. Procedures of Automated Patch Clamp

An HEK293-hERG stable cell strain was subcultured in an MEM/EBSS medium (10% FBS, 400 μg/mL G418, 1% MEM non-essential amino acid solution (100×), 1% sodium pyruvate solution) at a density of 1:4, and an automated patch clamp experiment was conducted between hour 48 and hour 72 after the start of the culture. On the day of the experiment, the cells were digested with 0.25% trypsin, then centrifuged, collected, and resuspended in an extracellular fluid (140 mM NaCl, 4 mM KCl, 1 mM $MgCl_2$, 2 mM $CaCl_2$, 5 mM D-glucose monohydrate, 10 mM Hepes, pH 7.4, 298 mOsm) to form a cell suspension. The cell suspension was placed on the cell bank of the Patchliner instrument, which then applied the cells to a chip (NPC-16) by means of a negative pressure controller. The negative pressure drew individual cells to the wells of the chip. When a whole-cell configuration was formed, the instrument was given hERG currents according to a set hERG current-voltage program and then automatically performed compound perfusion from low concentrations to high concentrations. Data were recorded and analyzed using the HEAK Patchmaster, HEAK EPC10 patch clamp amplifier (Nanion), Pathliner software and Pathcontrol HT software, and the currents of the compounds at each concentration and the current of the blank control were analyzed.

2.3. Results

The blocking of hERG potassium currents by the compounds disclosed herein was tested through the above assay, and the $IC_{50}$ values determined are shown in Table 9.

TABLE 9

IC$_{50}$ of the compounds disclosed herein for the blocking of hERG potassium currents

| Example | IC$_{50}$ (μM) |
|---------|----------------|
| 11 | >30 |
| 12 | >30 |
| 13 | >30 |

Note: IC$_{50}$≥30 μM indicates no inhibitory activity; 30>IC$_{50}$≥10 μM indicates weak inhibitory activity; 10>IC$_{50}$≥1 μM indicates moderate inhibitory activity; IC$_{50}$<1 μM indicates strong inhibitory activity.

Conclusion: The compounds claimed by the present disclosure have no inhibitory activity against hERG, showing better safety.

The invention claimed is:

1. A compound of general formula (I) or a tautomer, mesomer, racemate, enantiomer or diastereomer thereof or a mixture thereof, or a pharmaceutically acceptable salt thereof,

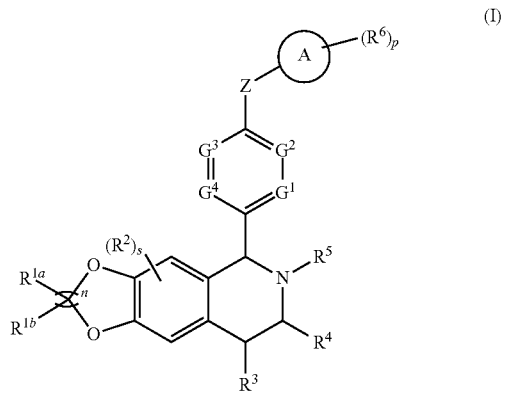

(I)

wherein:
R$^{1a}$ and R$^{1b}$ are identical or different and are each independently selected from the group consisting of H atom, deuterium atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

ring A is heterocyclyl;

Z is selected from the group consisting of O atom, S atom, NR$^7$ and CR$^9$R$^{10}$;

G$^1$, G$^2$, G$^3$ and G$^4$ are identical or different and are each independently CR$^8$ or a N atom;

R$^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

R$^3$ is selected from the group consisting of hydrogen atom, alkyl and cycloalkyl, wherein the alkyl and cycloalkyl are optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

$R^5$ is selected from the group consisting of hydrogen atom, alkyl, haloalkyl and cycloalkyl, wherein the alkyl and cycloalkyl are each independently optionally substituted with one or more substituents selected from the group consisting of halogen, alkyl, alkoxy, cyano, amino, nitro, carboxyl, hydroxy, hydroxyalkyl, cycloalkyl, heterocyclyl, aryl and heteroaryl;

$R^6$ are identical or different and are each independently selected from the group consisting of hydrogen atom, alkyl, deuterated alkyl, haloalkyl, alkoxy, cyano, amino, nitro, halogen, carboxyl, aldehyde, hydroxy, hydroxyalkyl, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^7$ is selected from the group consisting of hydrogen atom, alkyl, haloalkyl, alkenyl, propargyl, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^9$ and $R^{10}$ are identical or different and are each independently selected from the group consisting of hydrogen atom, halogen, alkyl, alkoxy, hydroxy, hydroxyalkyl, haloalkyl, alkenyl, alkynyl, cyano, cycloalkyl and heterocyclyl;

n is 1, 2 or 3;
s is 0, 1 or 2; and
p is 0, 1, 2 or 3.

2. A compound of general formula (I) or a tautomer, mesomer, racemate, enantiomer or diastereomer thereof or a mixture thereof, or a pharmaceutically acceptable salt thereof according to claim 1, wherein ring A is 3- to 6-membered heterocyclyl containing 1 to 3 heteroatoms selected from the group consisting of N atom, O atom and S atom.

3. A compound of general formula (I) or a tautomer, mesomer, racemate, enantiomer, diastereomer or a mixture thereof, or a pharmaceutically acceptable salt thereof according to claim 1, wherein $G^1$, $G^2$, $G^3$ and $G^4$ are all $CR^8$, or one of $G^1$, $G^2$, $G^3$ and $G^4$ is a N atom, and the others are $CR^8$; $R^8$ are as defined in claim 1.

4. The compound of general formula (I) or the tautomer, mesomer, racemate, enantiomer or diastereomer thereof or the mixture thereof, or the pharmaceutically acceptable salt thereof according to claim 1, wherein the compound of general formula (I) or the tautomer, mesomer, racemate, enantiomer or diastereomer thereof or the mixture thereof, or the pharmaceutically acceptable salt thereof, is a compound of general formula (II),

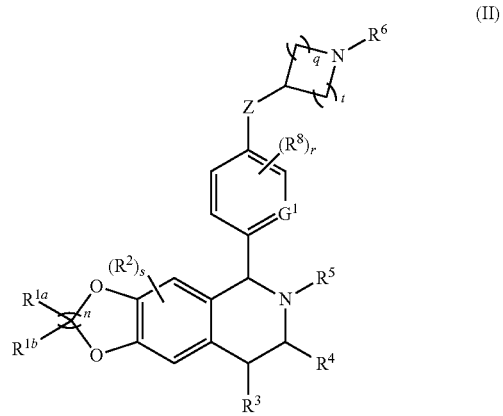

wherein:
r is 0, 1, 2 or 3;
q is 1, 2 or 3;
t is 1 or 2;
$Z$, $G^1$, $R^{1a}$, $R^{1b}$, $R^2$-$R^6$, $R^8$, n and s are as defined in claim 1.

5. The compound of general formula (I) or the tautomer, mesomer, racemate, enantiomer or diastereomer thereof or the mixture thereof, or the pharmaceutically acceptable salt thereof according to claim 1, wherein the compound of general formula (I) or the tautomer, mesomer, racemate, enantiomer or diastereomer thereof or the mixture thereof, or the pharmaceutically acceptable salt thereof, is a compound of general formula (IIG) or (IIGa),

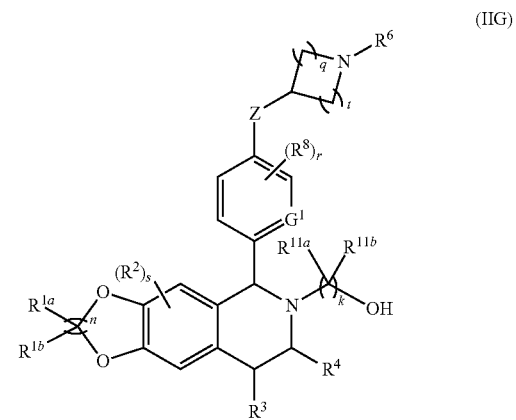

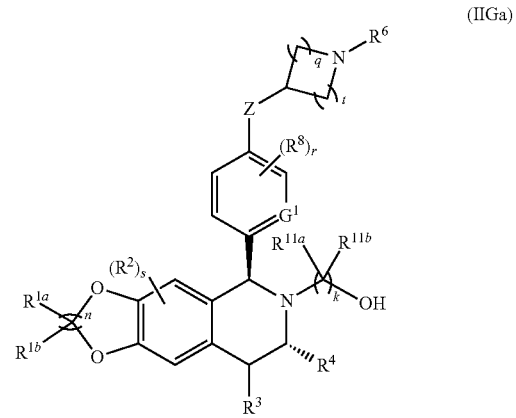

wherein:

$R^{11a}$ and $R^{11b}$ are identical or different and are each independently selected from the group consisting of hydrogen atom, halogen, alkyl, haloalkyl, hydroxyalkyl, alkoxy, cyano, amino, nitro, carboxyl, hydroxy, cycloalkyl, heterocyclyl, aryl and heteroaryl;

k is an integer from 1 to 6;

q is 1, 2 or 3;

t is 1 or 2;

r is 0, 1, 2 or 3;

$G^1$, Z, $R^{1a}$, $R^{1b}$, $R^2$-$R^4$, $R^6$, $R^8$, n and s are as defined in claim 1.

6. The compound of general formula (I) or the tautomer, mesomer, racemate, enantiomer or diastereomer thereof or the mixture thereof, or the pharmaceutically acceptable salt thereof according to claim 1, wherein Z is $NR^7$; $R^7$ is a hydrogen atom; n is 1.

7. The compound of general formula (I) or the tautomer, mesomer, racemate, enantiomer or diastereomer thereof or the mixture thereof, or the pharmaceutically acceptable salt thereof according to claim 1, wherein $G^1$ is a N atom; or $G^1$ is $CR^8$; $R^8$ is as defined in claim 1.

8. The compound of general formula (I) or the tautomer, mesomer, racemate, enantiomer or diastereomer thereof or the mixture thereof, or the pharmaceutically acceptable salt thereof according to claim 1, wherein $R^{1a}$ and $R^{1b}$ are identical or different and are each independently selected from the group consisting of H atom, deuterium atom, fluorine atom and $C_{1-6}$ alkyl; $R^2$ is a hydrogen atom: $R^3$ is a hydrogen atom: $R^4$ is a hydrogen atom or alkyl; $R^6$ is $C_{1-6}$ haloalkyl.

9. The compound of general formula (I) or the tautomer, mesomer, racemate, enantiomer or diastereomer thereof or the mixture thereof, or the pharmaceutically acceptable salt thereof according to claim 1, wherein $R^5$ is alkyl optionally substituted with one or more substituents selected from the group consisting of halogen, amino, cyano, hydroxy, alkoxy, carboxyl and cycloalkyl.

10. The compound of general formula (I) or the tautomer, mesomer, racemate, enantiomer or diastereomer thereof or the mixture thereof, or the pharmaceutically acceptable salt thereof according to claim 1, wherein the compound of general formula (I) or the tautomer, mesomer, racemate, enantiomer or diastereomer thereof or the mixture thereof, or the pharmaceutically acceptable salt, is selected from the group consisting of the following compounds:

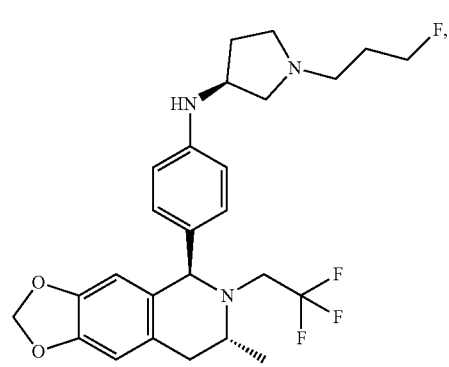

1

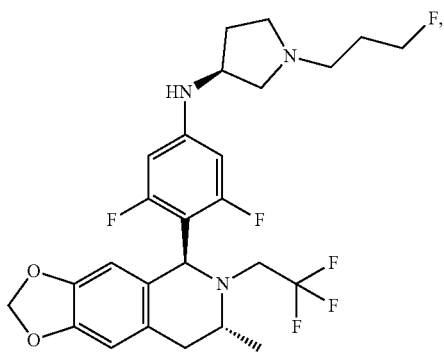

2

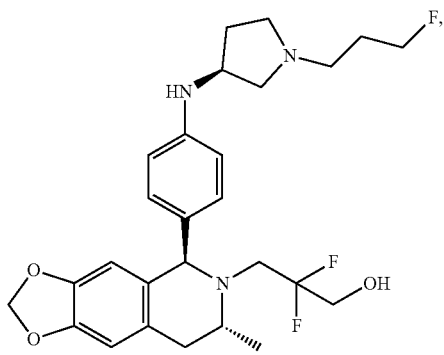

3

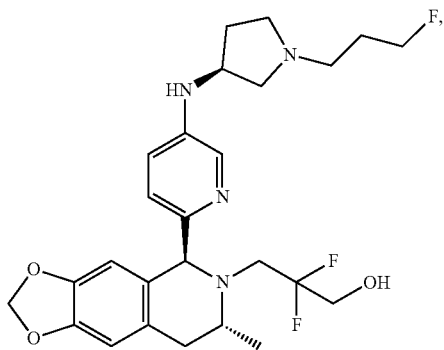

4

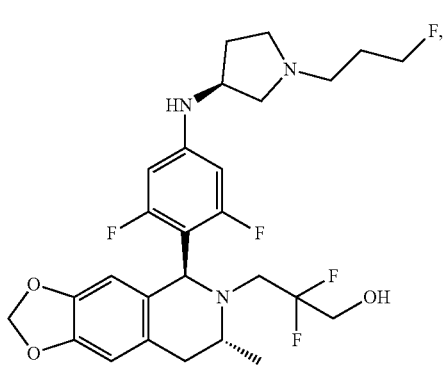

5

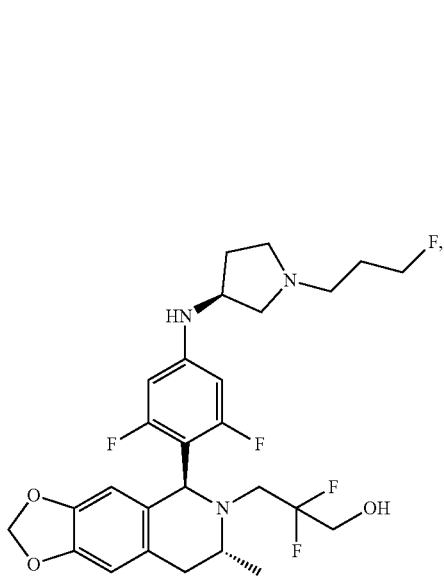

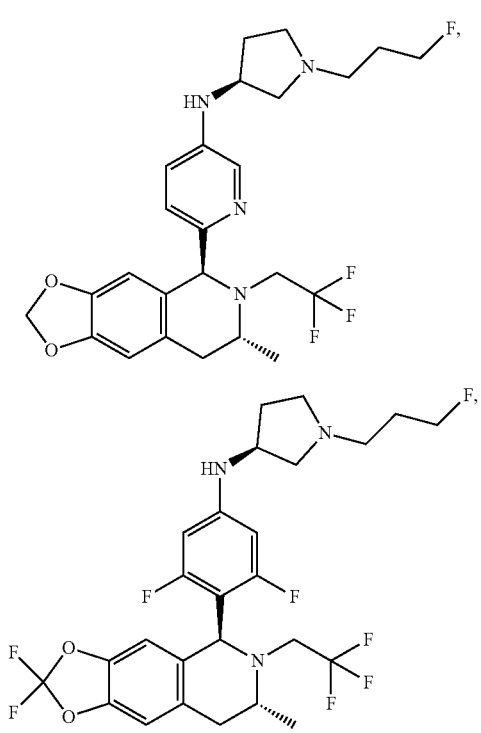
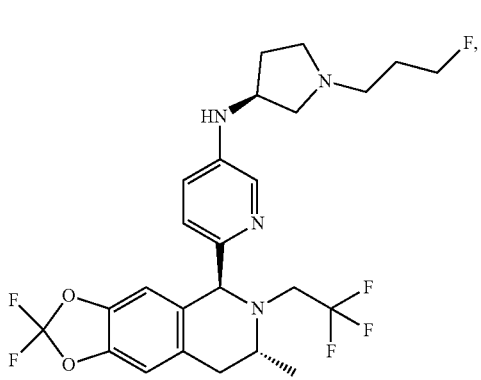
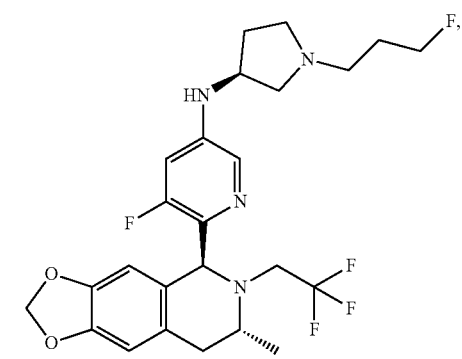
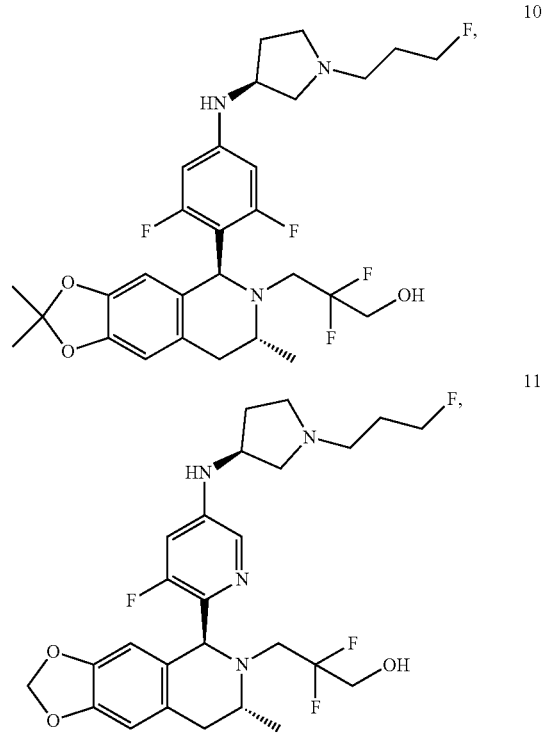
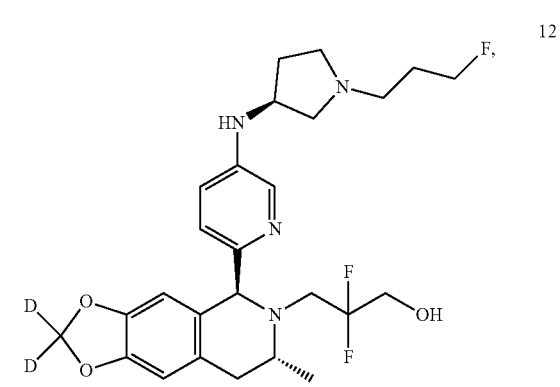
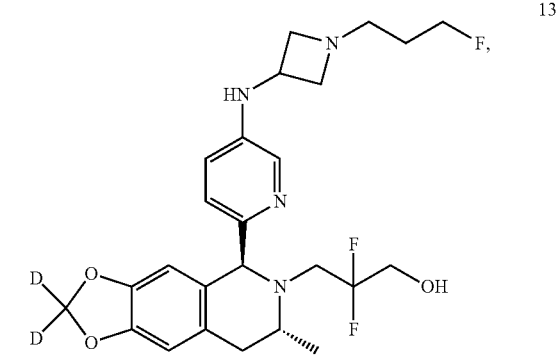

-continued
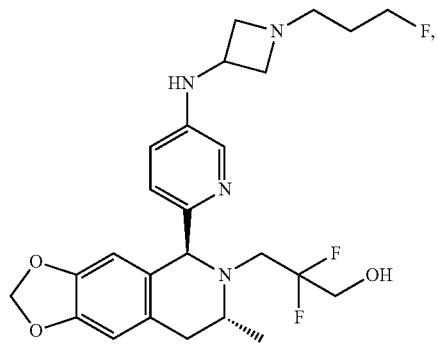
14
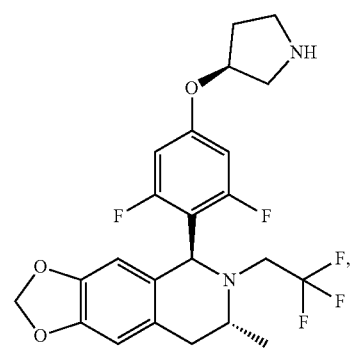
15e
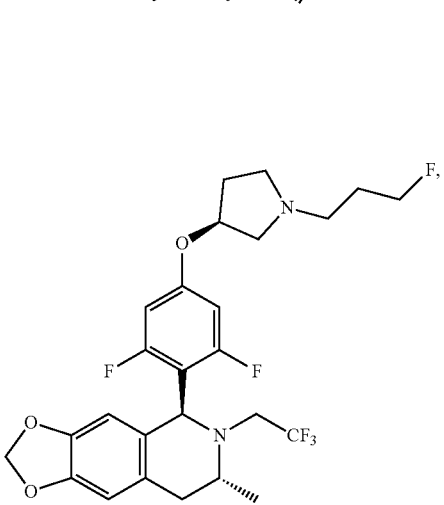
15
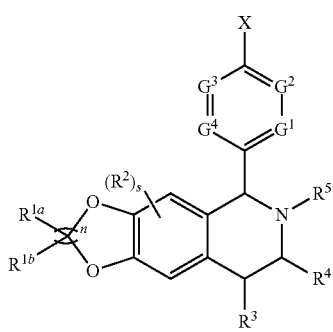
16
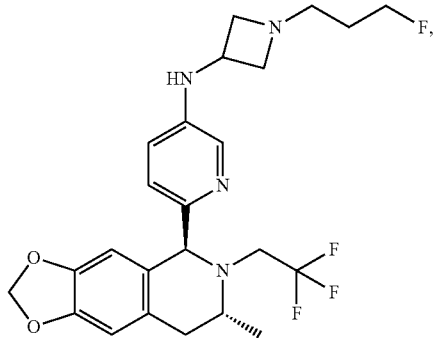
17
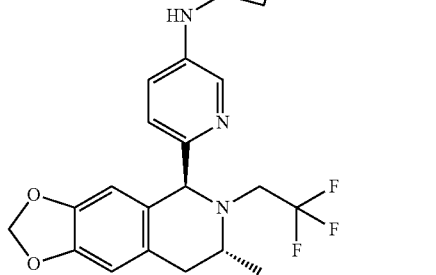
18 and
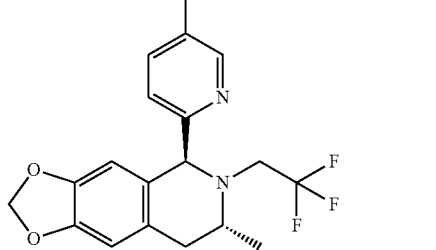
19
11. A compound of general formula (IA) or a tautomer, mesomer, racemate, enantiomer or diastereomer thereof or a mixture thereof, or a pharmaceutically acceptable salt thereof
(IA)
wherein:
R$^{1a}$ and R$^{1b}$ are identical or different and are each independently selected from the group consisting of H atom, deuterium atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

X is Br;

$G^1$, $G^2$, $G^3$ and $G^4$ are identical or different and are each independently $CR^8$ or a N atom;

$R^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

$R^3$ is selected from the group consisting of hydrogen atom, alkyl and cycloalkyl, wherein the alkyl and cycloalkyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

$R^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

$R^5$ is selected from the group consisting of alkyl, haloalkyl and cycloalkyl, wherein the alkyl and cycloalkyl are each independently optionally substituted with one or more substituents selected from the group consisting of halogen, alkyl, alkoxy, cyano, amino, nitro, carboxyl, hydroxy, hydroxyalkyl, cycloalkyl, heterocyclyl, aryl and heteroaryl;

$R^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

n is 1, 2 or 3; and s is 0, 1 or 2.

12. The compound of general formula (IA) or the tautomer, mesomer, racemate, enantiomer or diastereomer thereof or the mixture thereof, or the pharmaceutically acceptable salt thereof according to claim 11, wherein the compound of general formula (IA) or the tautomer, mesomer, racemate, enantiomer or diastereomer thereof or the mixture thereof, or the pharmaceutically acceptable salt, is selected from the group consisting of the following compounds:

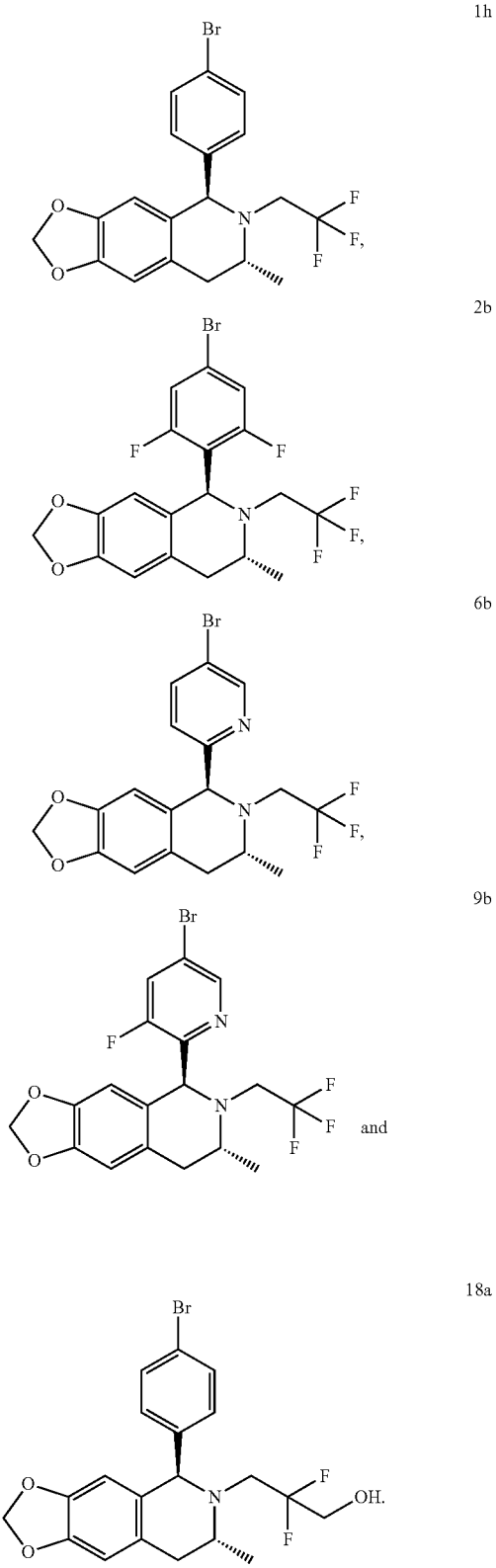

13. A compound of general formula (IIGA) or (IIGaA) or a tautomer, mesomer, racemate, enantiomer or diastereomer thereof or a mixture thereof, or a pharmaceutically acceptable salt thereof,

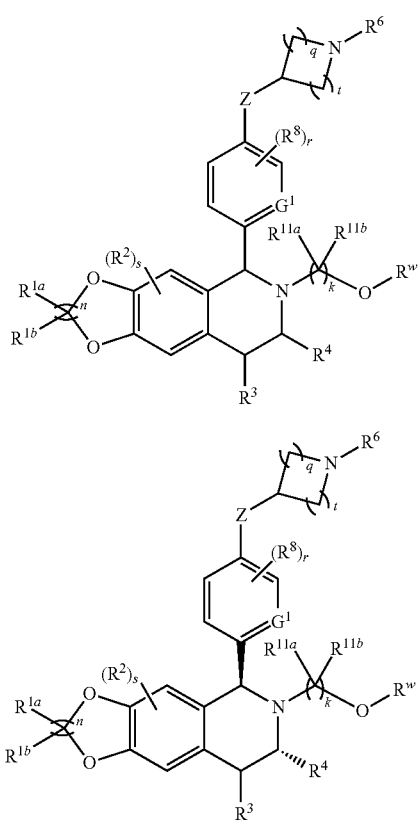

wherein:
R$^{1a}$ and R$^{1b}$ are identical or different and are each independently selected from the group consisting of H atom, deuterium atom, halogen, alkyl, deuterated alkyl, haloalkyl, alkoxy, hydroxy, hydroxyalkyl, cyano, amino, nitro, carboxyl, aldehyde, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

R$^w$ is a hydroxy protective group;

Z is selected from the group consisting of O atom, S atom, NR$^7$ and CR$^9$R$^{10}$;

G$^1$ is CR$^8$ or a N atom;

R$^2$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

R$^3$ is selected from the group consisting of hydrogen atom, alkyl and cycloalkyl, wherein the alkyl and cycloalkyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^4$ is selected from the group consisting of hydrogen atom, alkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, cyano, amino, nitro, hydroxy, hydroxyalkyl, cycloalkyl, heterocyclyl, aryl and heteroaryl;

R$^6$ is independently selected from the group consisting of hydrogen atom, alkyl, deuterated alkyl, haloalkyl, alkoxy, cyano, amino, nitro, halogen, carboxyl, carboxylate group, aldehyde, hydroxy, hydroxyalkyl, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^7$ is selected from the group consisting of hydrogen atom, alkyl, haloalkyl, alkenyl, propargyl, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^8$ are identical or different and are each independently selected from the group consisting of hydrogen atom, halogen, alkyl, alkoxy, haloalkyl, alkenyl, alkynyl, cyano, cycloalkyl and heterocyclyl, wherein the alkyl, cycloalkyl and heterocyclyl are each independently optionally substituted with one or more substituents selected from the group consisting of halogen, alkyl, alkoxy, cyano, amino, nitro, hydroxy, hydroxyalkyl, carboxyl, cycloalkyl, heterocyclyl, aryl and heteroaryl;

R$^9$ and R$^{10}$ are identical or different and are each independently selected from the group consisting of hydrogen atom, halogen, alkyl, alkoxy, hydroxy, hydroxyalkyl, haloalkyl, alkenyl, alkynyl, cyano, cycloalkyl and heterocyclyl;

R$^{11a}$ and R$^{11b}$ are identical or different and are each independently selected from the group consisting of hydrogen atom, halogen, alkyl, haloalkyl, hydroxyalkyl, alkoxy, cyano, amino, nitro, carboxyl, aldehyde, hydroxy, cycloalkyl, heterocyclyl, aryl and heteroaryl;

k is an integer from 1 to 6;

q is 1, 2 or 3;

t is 1 or 2;

n is 1, 2 or 3;

r is 0, 1, 2 or 3; and s is 0, 1 or 2.

14. The compound of general formula (IIGA) or (IIGaA) or the tautomer, mesomer, racemate, enantiomer or diastereomer thereof or the mixture thereof, or the pharmaceutically acceptable salt thereof according to claim 13, wherein the compound of general formula (IIGA) or (IIGaA) or the tautomer, mesomer, racemate, enantiomer or diastereomer thereof or the mixture thereof, or the pharmaceutically acceptable salt, is selected from the group consisting of the following compounds:

3e
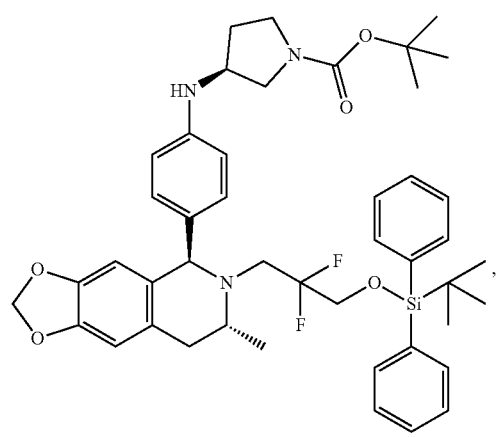
3f
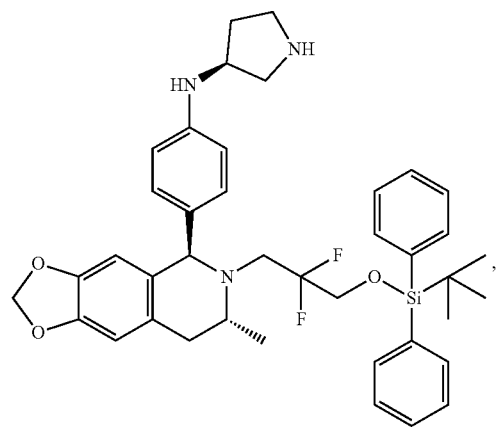
3g
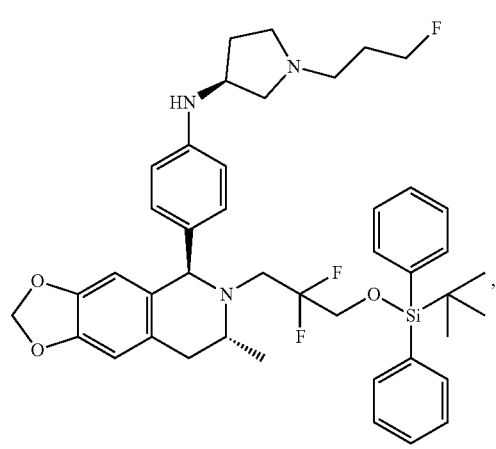
-continued
4c
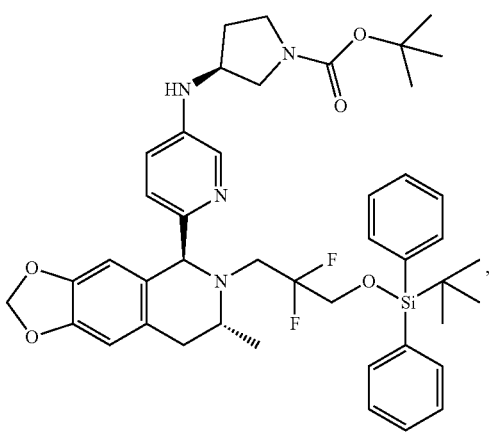
4d
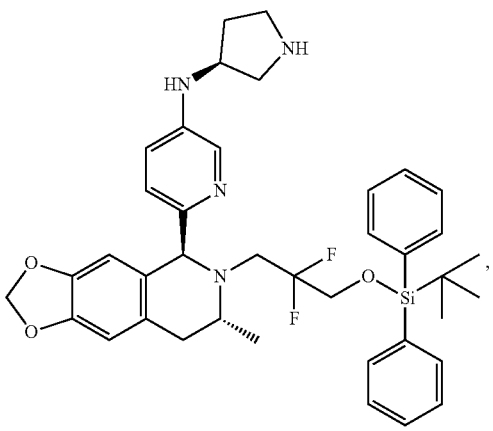
4e
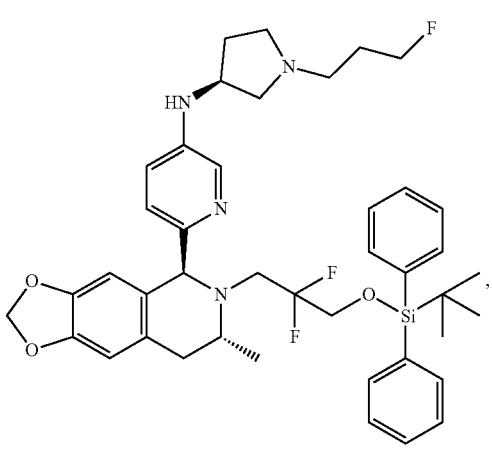

143
-continued
144
-continued
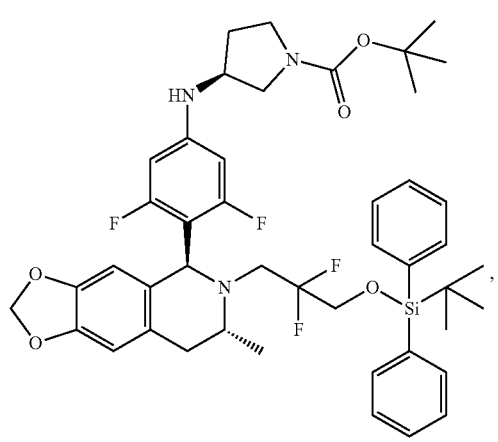
5c
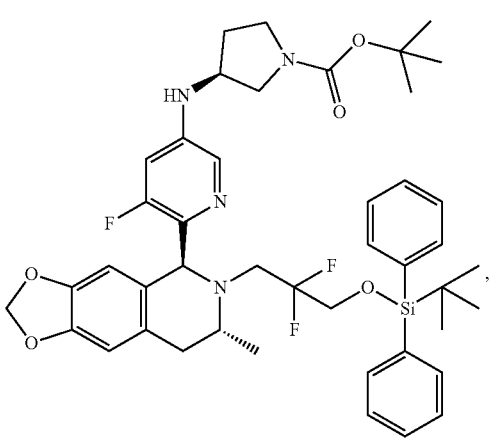
11c
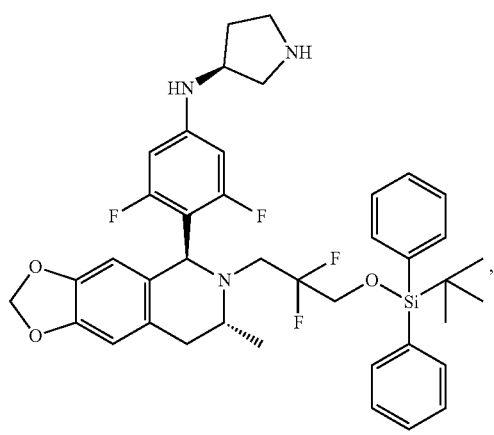
5d
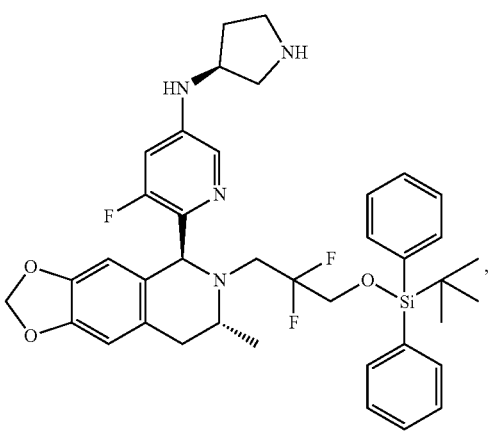
11d
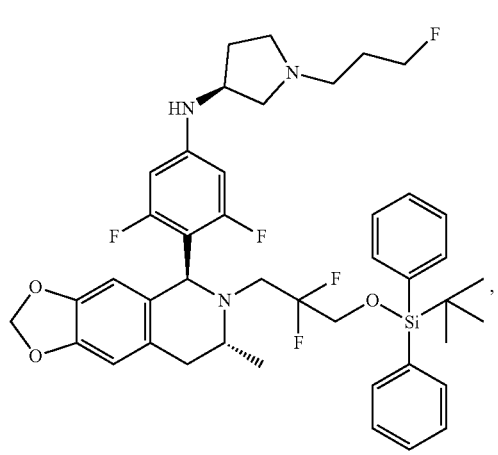
5e
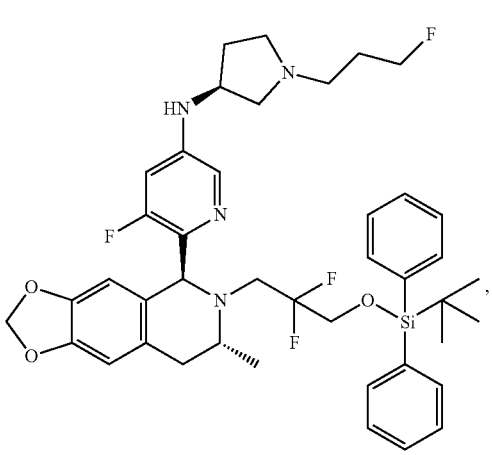
11e

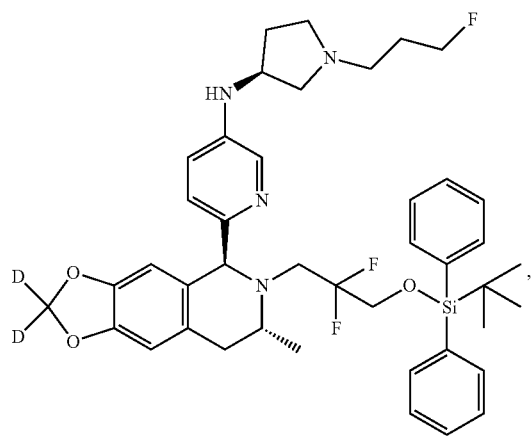
12b
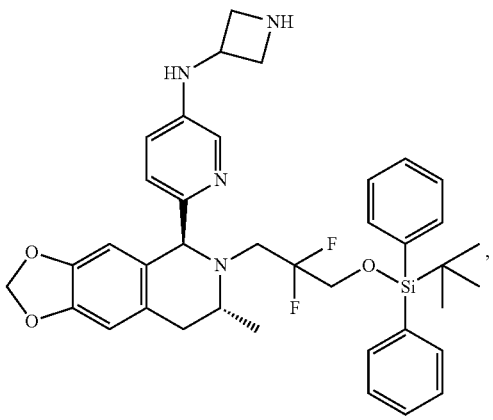
14b
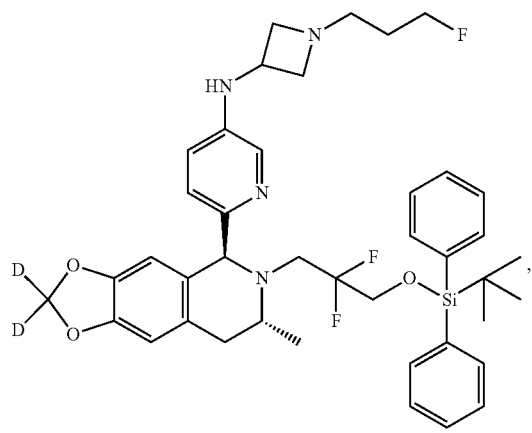
13a
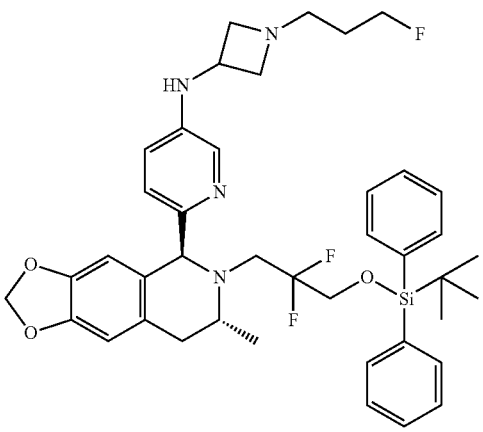
14c
and
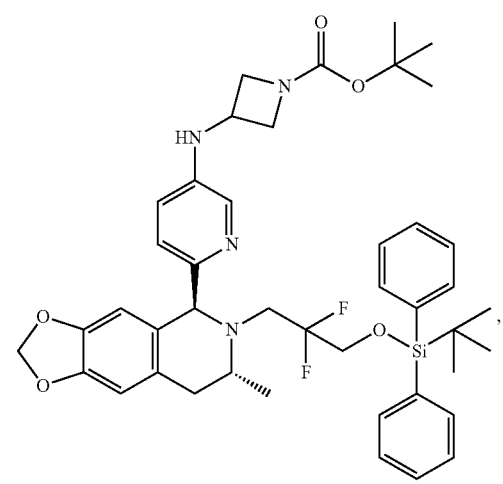
14a
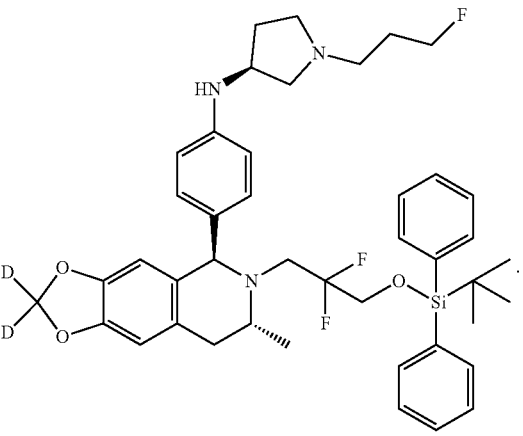
19b
15. A method for preparing the compound of general formula (I) or the tautomer, mesomer, racemate, enantiomer or diastereomer thereof or the mixture thereof, or the pharmaceutically acceptable salt thereof according to claim 1, comprising:

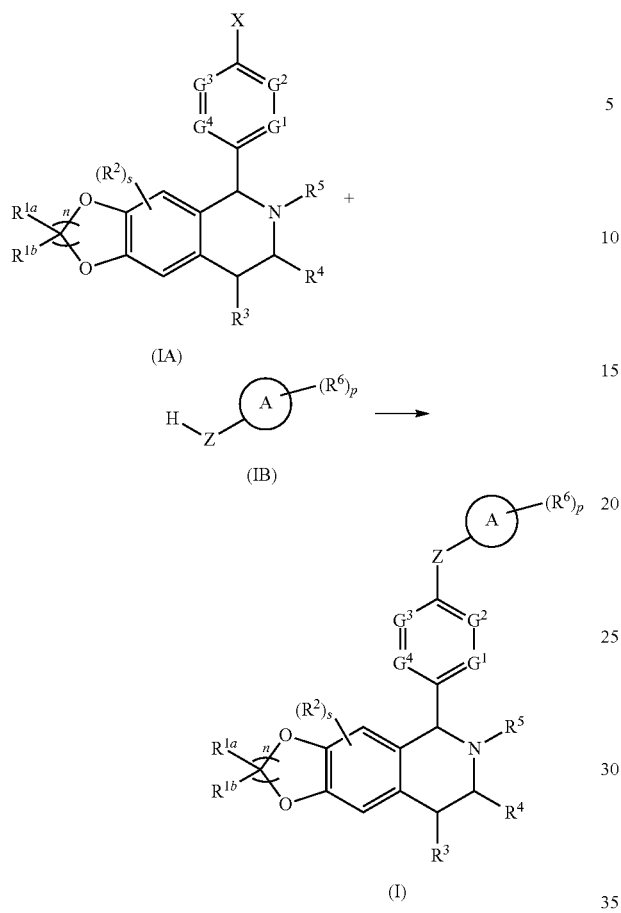

subjecting a compound of general formula (IA) and a compound of general formula (IB) to a coupling reaction to give the compound of general formula (I), wherein:

X is Br;

ring A, Z, $G^1$, $G^2$, $G^3$, $G^4$, $R^{1a}$, $R^{1b}$, $R^2$-$R^6$, n, p and s are as defined in claim 1.

16. A method for preparing the compound of general formula (JIG) or (IIGa) or the tautomer, mesomer, racemate, enantiomer or diastereomer thereof or the mixture thereof, or the pharmaceutically acceptable salt thereof according to claim 5, comprising:

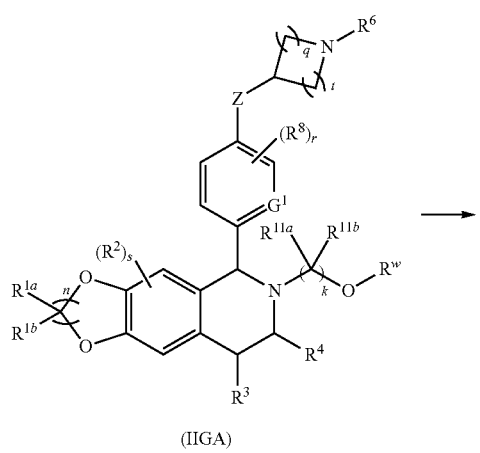

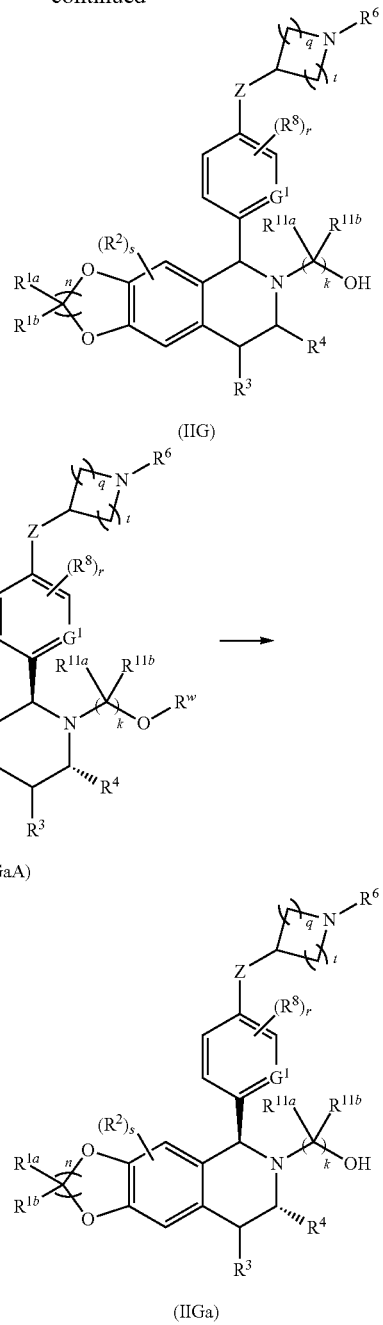

removing a hydroxy protective group from a compound of general formula (IIGA) to give the compound of general formula (JIG), or removing a hydroxy protective group from a compound of general formula (IIGaA) to give the compound of general formula (IIGa), wherein:

$R^w$ is a hydroxy protective group;

Z, $G^1$, $R^{1a}$, $R^{1b}$, $R^2$-$R^4$, $R^6$, $R^8$, $R^{11a}$, $R^{11b}$, q, t, k, r, n and s are as defined in claim 5.

17. A pharmaceutical composition comprising a therapeutically effective amount of the compound of general formula (I) or the tautomer, mesomer, racemate, enantiomer or diastereomer thereof or the mixture thereof, or the pharmaceutically acceptable salt thereof according to claim 1, and one or more pharmaceutically acceptable carriers, diluents or excipients.

18. A method of treating cancer in a subject in need thereof, the method comprising administrating to the subject, an effective amount of the pharmaceutical composition according to claim 17.

19. A method for treating an estrogen receptor-mediated or -dependent disease or condition in a subject in need thereof, the method comprising administering to the subject an effective amount of the pharmaceutical composition according to claim 17, wherein the estrogen receptor-mediated or -dependent disease or condition is selected from the group consisting of cancer, central nervous system deficit, cardiovascular system deficit, blood system deficit, immune and inflammatory disease, susceptible infection, metabolic deficit, neurologic deficit, psychiatric deficit and reproductive deficit.

20. The method of claim 19, wherein the cancer is selected from the group consisting of breast cancer, endometrial cancer, uterine cancer, cervical cancer, skin cancer, prostate cancer, ovarian cancer, fallopian tube tumor, hemophilia and leukemia.

\* \* \* \* \*

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic Sequence_Y537S: F

<400> SEQUENCE: 1
aagaacgggg ccccccgacc gcgcggagag                                30

<210> SEQ ID NO 2
<211> LENGTH: 39
<212> TYPE: DNA
<213> ORGANISM: Artificial Sequence
<220> FEATURE:
<223> OTHER INFORMATION: Synthetic Sequence_Y537S: R

<400> SEQUENCE: 2
catctccagc agcaggtcag agaggggcac cacgttctt                      39
```